(12) United States Patent
Besson

(10) Patent No.: US 7,539,284 B2
(45) Date of Patent: May 26, 2009

(54) METHOD AND SYSTEM FOR DYNAMIC LOW DOSE X-RAY IMAGING

(76) Inventor: Guy M. Besson, 1672 Emerald St., Broomfield, CO (US) 80020

( * ) Notice: Subject to any disclaimer, the term of this patent is extended or adjusted under 35 U.S.C. 154(b) by 0 days.

(21) Appl. No.: 12/018,148

(22) Filed: Jan. 22, 2008

(65) Prior Publication Data

US 2008/0118023 A1      May 22, 2008

Related U.S. Application Data

(63) Continuation-in-part of application No. 11/351,909, filed on Feb. 10, 2006, now Pat. No. 7,340,032, and a continuation-in-part of application No. 11/351,446, filed on Feb. 10, 2006, now Pat. No. 7,342,993.

(60) Provisional application No. 60/931,614, filed on May 24, 2007, provisional application No. 60/881,356, filed on Jan. 19, 2007, provisional application No. 60/654,922, filed on Feb. 22, 2005, provisional application No. 60/652,127, filed on Feb. 11, 2005.

(51) Int. Cl.
*G01N 23/04* (2006.01)
(52) U.S. Cl. .......................... 378/62; 378/147; 378/160
(58) Field of Classification Search .................. 378/16, 378/19, 62, 145–153, 160
See application file for complete search history.

(56) References Cited

U.S. PATENT DOCUMENTS

| | | | |
|---|---|---|---|
| 4,228,357 A | 10/1980 | Annis | |
| 4,398,302 A | 8/1983 | Pfeiler | |
| 4,989,225 A | 1/1991 | Gupta et al. | |
| 5,724,403 A | 3/1998 | Siochi et al. | |
| 6,950,492 B2 | 9/2005 | Besson | |
| 7,016,457 B1 | 3/2006 | Senzig et al. | |
| 7,123,680 B2 * | 10/2006 | Katada et al. | 378/16 |
| 2001/0048732 A1 | 12/2001 | Wilson et al. | |
| 2003/0209662 A1 | 11/2003 | Nelson et al. | |
| 2005/0027194 A1 | 2/2005 | Adler et al. | |
| 2005/0055174 A1 | 3/2005 | David et al. | |
| 2006/0182224 A1 | 8/2006 | Besson | |
| 2006/0182225 A1 | 8/2006 | Besson | |

OTHER PUBLICATIONS

Besson, G. "CT Projections Estimation and applications to fast and local reconstruction"; SPIE vol. 3661; pp. pp. 1196-1207; Feb. 1999.

(Continued)

*Primary Examiner*—Courtney Thomas
(74) *Attorney, Agent, or Firm*—Lathrop & Gage LLP

(57) ABSTRACT

A method and system for performing fluoroscopic imaging of a subject has high temporal and spatial resolution in a center portion of the captured dynamic images. The system provides for reduced X-ray dose to the patient associated with that part of the X-ray beam associated with a peripheral portion of the captured images although temporal, and in some embodiments spatial, resolution is reduced in the peripheral portion of the image. The system uses a rotating collimator to produce an X-ray beam having narrow wing portions associated with the peripheral portions of the image, and a broader central region associated with the high resolution center portion of the images.

30 Claims, 36 Drawing Sheets

OTHER PUBLICATIONS

Schomberg, H. et al., "The Grinding Method For Image Reconstruction By Fournier Transformation"; IEEE Transactions on Medical Imaging; pp. 596-607; vol. 14 No. 3; Sep. 1995.

National Cancer Institute, Interventional Fluoroscopy, Reducing Radiation Risks for Patients and Staff. NIH Publication No. 05-5286, 2005.

U.S. Appl. No. 11/351,909; Office Action; Jul. 13, 2006.

U.S. Appl. No. 11/351,909; Response to Office Action of Jul. 13, 2006.

U.S. Appl. No. 11/351,909; Office Action; Apr. 10, 2007.

U.S. Appl. No. 11/351,909; Response to Office Action of Apr. 10, 2007.

U.S. Appl. No. 11/351,909; Summary of Telephone Interview and Intended Course of Action; Sep. 7, 2007.

U.S. Appl. No. 11/351,909; Summary of Telephone Interview and Submission of Terminal Disclaimer; Sep. 11, 2007.

U.S. Appl. No. 11/351,909; Notice of Allowance; Oct. 10, 2007.

U.S. Appl. No. 11/351,446; Office Action; Apr. 6, 2007.

U.S. Appl. No. 11/351,446; Response to Office Action of Apr. 6, 2007.

U.S. Appl. No. 11/351,446; Notice of Allowance; Oct. 11, 2007.

Rudin, S. and Bednarek, DR.; "Spatial shaping of the beam: collimation, grids, equalization filters, and region-of-interest fluoroscopy"; In: Balter S, Shope TB, Eds. Syllabus: a categorical course in physics—physical and technical aspects of angiography and interventional radiology; Oak Brook, Ill: Radiology Society of North America; pp. 75-85; 1995.

\* cited by examiner

METHOD AND SYSTEM FOR DYNAMIC LOW DOSE X-RAY IMAGING

CROSS-REFERENCE TO RELATED APPLICATIONS

This application claims the benefit of priority to U.S. Provisional Patent Application No. 60/881,356, filed Jan. 19, 2007, and U.S. Provisional Patent Application No. 60/931,614, filed May 24, 2007. This application is also a continuation-in-part of U.S. Ser. No. 11/351,909, filed Feb. 10, 2006 now U.S. Pat. No. 7,340,032, and a continuation-in-part of U.S. Ser. No. 11/351,446, filed Feb. 10, 2006 now U.S. Pat. No. 7,342,993, both of which claim the benefit of priority to U.S. Provisional Patent Application No. 60/652,127, filed Feb. 11, 2005, and U.S. Provisional Patent Application No. 60/654,922, filed Feb. 22, 2005. Each of the aforementioned patent applications is incorporated herein by reference in its entirety.

BACKGROUND

This disclosure relates to X-ray imaging, and more particularly to the dynamic low-dose imaging of an object or subject with a moving detector, as well as to the dynamic low-dose tomosynthesis and limited-angle tomographic imaging of a subject with a moving detector and a moving X-ray source. Exemplary applications are in the sub-fields of fluoroscopy, radiography, and cardiology. Other applications are in the fields of non-destructive testing, homeland security and animal imaging.

X-ray fluoroscopy was developed shortly after Roentgen discovered X-rays, using a fluorescent screen. Fluoroscopy developed rapidly to provide an essential investigative and interventional tool. Major advancements occurred in the 1940s-1950s with the development of the image intensifier, and in the mid 1970s when investigators began applying digital technology to fluoroscopic imaging. According to a publication of the National Cancer Institute (NCI) and The Society of Interventional Radiology, "Interventional fluoroscopy represents a tremendous advantage over invasive surgical procedures, because it requires only a very small incision, substantially reduces the risk of infection and allows for shorter recovery time compared to surgical procedures" (NCI. Interventional Fluoroscopy, Reducing Radiation Risks for Patients and Staff. NIH Publication No. 05-5286, 2005) As an example of this advantage, the number of cardiac procedures being performed through Percutaneous Transluminal Coronary Angioplasty (PTCA) continues to increase rapidly, see FIG. 17. About 657,000 such procedures were performed in 2002 in the USA; this procedure is now recommended whenever possible as first-line treatment for ST-Elevation Myocardial Infarction (STEMI) heart attacks.

The total number of minimally invasive image guided interventions (IGI) procedures, (ranging from cardiac electrophysiology to neurology and including treatment of liver cancers, vertebroplasty, abdominal aortic aneurysm treatments and urinary tract procedures) is expected to keep increasing, due to the development of new devices and procedures and the aging of the population. Fluoroscopy is commonly used for guidance and monitoring of IGI procedures. As applied to electrophysiology (EP) diagnosis and treatment, the number of hospitalizations for atrial fibrillation (either as primary or secondary diagnosis, with a predominant increase in the later) have increased 450% from 1983 to 2003 In addition to interventional procedures, Fluoroscopy is also commonly used for many diagnostic procedures such as diagnostic coronary angiography and endoscopic retrograde choleangiography (ERCP).

According to reports received by the FDA of skin injury from fluoroscopy, the two procedures with the largest number of injury reports are RF cardiac catheter ablation and coronary angioplasty. The treatment of coronary disease is also a field where reduced radiation exposure would be advantageous. Currently, treating Chronic Total Occlusions (CTOs) present significant challenges as visualization of occlusions, even with retrograde contrast injection, is difficult using current fluoroscopy systems due to the lack of occluded structure contrast in the images.

DESCRIPTION OF THE RELATED ART

Many interventional procedures utilize X-ray as the preferred imaging modality for intervention planning, guidance, monitoring and control. Although X-ray imaging systems for this purpose are widely available, prior-art systems and approaches are significantly limited. In particular, prior art interventional imaging poses the major impediments of high subject radiation dose and cumulative physician exposure to radiation. In certain procedures, the subject X-ray dose may be high enough to burn the subject's skin. Furthermore, a significant fraction of experienced radiologists and cardiologists are approaching or have reached their annual or life-time accumulated dose limit, and are therefore prevented from, or limited in, the practice of their skills. In a typical fluoroscopic procedure, an area detector is used to provide a fairly wide imaging field (typically 6 to 16 inches) at a high refresh rate (30 frames per second or higher). Over the years, image-intensifier technology has evolved to provide electronic amplification and viewing of images. In general, the X-ray image formed on an input phosphor screen is amplified in intensity by a very large factor by an image intensifier. The bright, but typically reduced-area output image is electronically recorded by a video system, and displayed to the physician in essentially real time. Recently, a number of vendors have introduced digital detectors with refresh rate and X-ray absorption efficiency comparable to that of phosphor screens with image intensifiers. However, these improvements have not resolved the issues of high subject and attendant dosage.

Current technologies are further limited, in part, due to use of large area detectors and large exposure area beams. While a number of systems currently offered provide adjustable field-of-view imaging, a large exposure field is desirable to allow the physician to track the progress of an intervention and to maintain view of specific anatomical landmarks during a procedure. Large exposed areas translate into high detector costs and the need to reject scattered X-rays at the detector. Typically, scattered X-rays are rejected by use of a scatter-rejecting Potter-Bucky grid (hereinafter, "Bucky grid")—essentially a moving collimator of lead strips that blocks off-axis photons. A Bucky grid absorbs about one-half of the radiation that has been transmitted through the patient and thus requires that the applied dose be increased by a factor of two. Use of a Bucky grid therefore adds to the aforementioned high subject and attendant dose; furthermore, large exposed areas result in relatively low refresh rates over the entire image. For example, read-out of an entire large area detector, or a large area of such a detector, limits the imaging refresh rate.

Cardiology and neurology interventions, which typically require the insertion of a catheter or similar interventional device in the subject's vasculature, can necessitate continuous or intermittent subject exposures for extended durations, resulting in high X-ray doses. For example, specific cardiology procedures using current, known technologies, such as in electro-physiology, can last for more than one hour, and accordingly necessitate very high subject doses. Interventional radiologists, cardiologists and other attending staff are also subject to significant X-ray exposure and dose, to such a degree that dose limitation regulations may prevent them from active work for a significant fraction of their available time, thus leading to underutilization of expensive resources.

Three-dimensional (3D) imaging currently requires complex and expensive systems. In addition, most currently available 3D imaging systems also deliver high subject doses, and often limit access to the subject due to use of a gantry, a large area detector or a combination of area detectors.

Limitations of Current Digital Fluoroscopy Systems

The major limitations of fluoroscopy as an image-guided interventional tool are X-ray dose, three-dimensional (3D) structure superposition in a projection image, and lack of structure contrast.

X-ray imaging systems are often designed to be X-ray noise limited. Therefore a trade-off exists between image quality and dose. Currently, no specific dose guidelines beyond "as low-as reasonably achievable" are provided to the user. In practice, most existing detectors exhibit lower detective quantum efficiency (DQE) at lower exposures, thereby setting another lower limit to the X-ray dose.

In projection imaging the detected signal is proportional to the dexel area. According to the Rose detection model, the dose necessary to detect a structure of size d (such as a small vessel of diameter d) is proportional to the fourth power of 1/d. As interventional tools become smaller and more easily navigable, increasingly complex interventions are planned on smaller structures. A patient might require treatment of a coronary artery 2 to 3 mm in diameter, and a stent structure correspondingly sized will test the limits of a digital system with a dexel size of 200-μm.

Object and structure visualization are often limited by both lack of inherent X-ray contrast and 3D structures superposition. Typically, contrast enhancing dyes are used to increase contrast but in some cases these have been shown to pose toxic risk especially to the kidneys.

SUMMARY

Slot-scanning for chest imaging has been demonstrated to reduce detected scattered photons by a factor of two to three. In turn this enables Bucky grid elimination and an associated radiation dose savings likely approaching a factor of two. An additional dose savings is obtained by projecting and rotating a slot beam in accordance with the geometry described herein below. Attendant dose savings is proportional to the patient's.

In practice, dose spreading includes varying beam incidence angle during a procedure. For a given angular range, the disclosed system reduces overlap between regions of high skin dose, because the high skin-dose regions are smaller.

The methods and system disclosed herein allow for low-dose X-ray examinations as well as dynamic multispectral X-ray imaging in both radiographic and fluoroscopic modes, by translating and rotating a narrow-aperture detector and shaping a beam of X-rays accordingly, or by sweeping or rotating a beam of specific shape across the face of an area detector.

In one embodiment, X-ray examination of a subject or object involves projecting a spinning fan beam of X-rays through a subject, the fan beam having a central section having a width two or more times wider than a width of wing portions of the beam. The beam is received by a detector and an image of the subject is reconstructed. The image has high spatial and temporal resolution in a portion corresponding to the central section of the beam, and degraded resolution in areas corresponding to those illuminated by the wing portions of the beam.

In one embodiment, a system for creating a rapid sequence of X-ray images of an subject has an X-ray source capable of emitting X-ray photons. A collimator collimates the X-ray photons from the X-ray source into a fan beam having a center portion and a wing portion, a measurement selected from a width and a diameter of the center portion being larger than a width of the wing portion. An apparatus rotates the collimator to spin the fan beam about an axis extending from the X-ray source to a detector, wherein the wing portion of the fan beam intermittently illuminates at least a portion of the subject disposed between the collimator and the detector. The detector is capable of receiving the fan beam and generating electronic information therefrom. An image processor constructs the rapid sequence of images of the subject from the electronic information.

In one embodiment, a method for creating a rapid sequence of X-ray images of a subject includes generating X-ray radiation in an X-ray source and passing the X-ray radiation through a collimator that rotates about an axis extending from the X-ray source to an X-ray detector, thereby forming a spinning fan beam centered on the axis, the fan beam having a center portion and a wing portion, a measurement selected from a width and a diameter of the center portion being larger than a width of the wing portion. At least a portion of the fan beam is passed through a portion of the subject, the fan beam is received in the X-ray detector and electronic information is generated therefrom. The rapid sequence of images of the subject is constructed from the electronic information.

In one embodiment, a method for performing a medical procedure on a patient includes generating X-ray radiation and passing the X-ray radiation through a rotating collimator, to form a spinning fan beam having an axis, a center portion, and a wing portion. At least a portion of the fan beam is passed through a region of interest in the patient, and the spinning fan beam is received in an X-ray detector; electronic information is generated therefrom. A rapid sequence of images of the region of interest in the patient is constructed from the electronic information, and a catheter is passed through a vessel of the patient into the region of interest in the patient. The rapid sequence of images is used to image the catheter and to guide placement of a tip of the catheter.

In one embodiment, a system for creating a rapid sequence of X-ray images of a subject has an X-ray source and a collimator for collimating the X-ray photons from the X-ray source into a fan beam having a center portion and a wing portion. A measurement selected from a width and a diameter of the center portion is larger than a width of the wing portion. An apparatus rotates the collimator to spin the fan beam about an axis extending from the X-ray source to a detector, the wing portion of the fan beam thereby intermittently illuminating at least a portion of the subject disposed between the collimator and the detector. An image processor constructs the rapid sequence of images of the subject from the electronic information.

In another embodiment, a system is provided for generating a fan beam of X-rays rotating about an axis, the axis extending from an X-ray source through a subject to a detector. T fan beam has a central section having a width two or more times wider than a width of wing portions of the beam.

The beam is received by the detector. The system has an image processor for reconstructing an image of at least part of the subject from information captured by the detector.

In some embodiments, the detector rotates synchronously with the fan beam, in other embodiments the detector is a stationary area detector and a virtual update window in the image processor is rotated synchronously with the fan beam.

Still further, the disclosed instrumentalities may be incorporated in multi-spectral imaging systems with or without computer assisted diagnosis (CAD). One example of this would be to retrofit the system that is shown and described in U.S. Pat. No. 6,950,492, which is hereby incorporated by reference to the same extent as though fully disclosed herein. This type of system, for example, may be provided with a rotating collimator assembly as described herein, as well as a rotating detector driven in synchronicity with the collimator assembly.

DETAILED DESCRIPTION

Figure 1A:
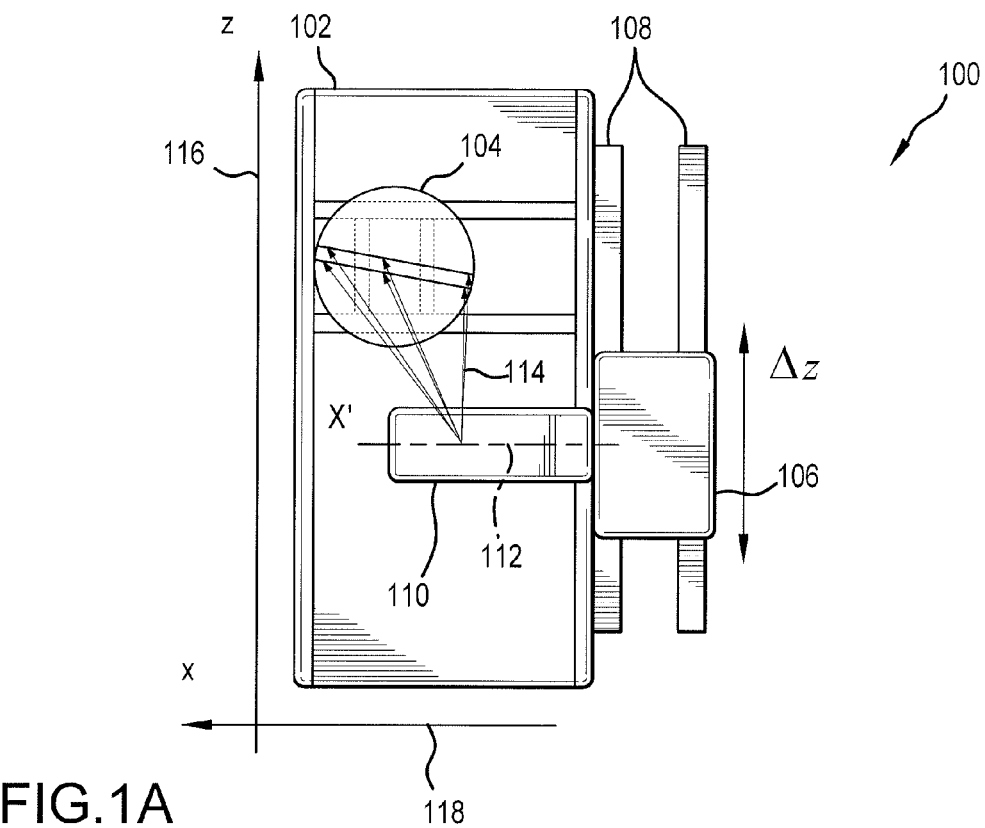
FIG. 1A is a top orthogonal view of a system for dynamic low dose X-ray imaging, including a moveable detector assembly.

It should be noted that the matter contained in the following description and/or shown in the accompanying drawings may be embodied in various forms, and should therefore be interpreted as illustrative, and not in a limiting sense. Elements shown in the drawings are not necessarily to scale and may be exaggerated, enlarged or simplified, to facilitate understanding of the invention. The system implementation according to the various shown embodiments is amenable to automated controls.

Figure 11:
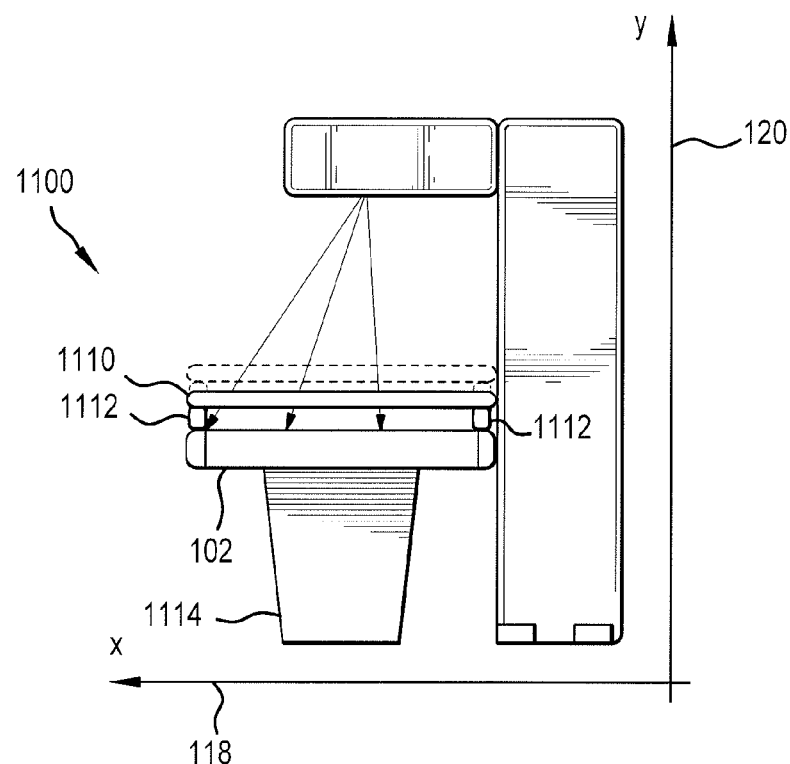
FIG. 11 illustrates a system for dynamic low dose X-ray imaging including a moveable subject table, in accordance with one embodiment.

Turning now to FIG. 1A, a system 100 for dynamic low dose X-ray imaging is shown in a top orthogonal view. System 100 for example allows a significant reduction in subject and physician dose while permitting effective performance of an interventional or diagnostic procedure. A frame structure (or cradle) 102, designed for placement beneath or within a subject table (see, e.g., table 1110; FIG. 11), permits relative motion of a detector assembly 104 (shown bounded by a circle) with respect to the table. An X-ray tube apparatus assembly, such as a column or X-ray source assembly having an X-ray tube and a collimator, may for example be set upon rails that allow motion of the assembly in a direction generally parallel to the subject table.

In one embodiment, a tube column assembly 106 is placed on one side of cradle 102 and the subject table, and may be dynamically rolled along rails 108 (or similar translation structure, such as a slide or roller assembly), which are for example parallel to the subject table, during the examination. In one embodiment, an X-ray tube 110 pivots with respect to a pivot axis (x') 112 that lies generally parallel to the subject table (alternatively, image plane x O z). The combination of independent detector motion (relative to a surface that is often chosen to be parallel to the plane of the subject table), tube column translation and tube rotation, together with an adjustable collimator assembly (e.g., assembly 1010, described herein below with respect to FIG. 10), allows projection of an X-ray beam 114 of specific shape towards any area on the subject table.

Figure 1B:
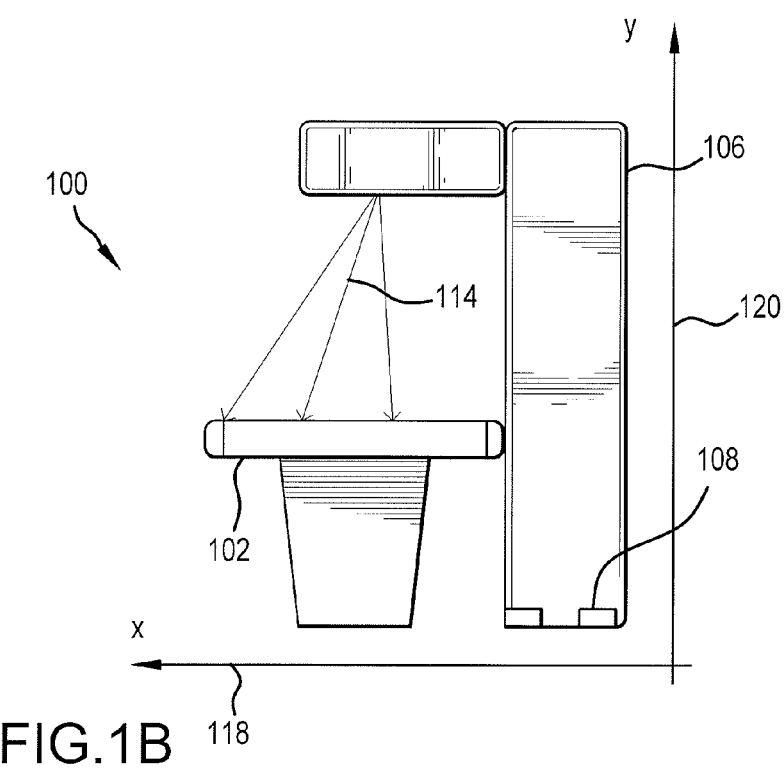
FIG. 1B is a front orthogonal view of the system of FIG. 1A.
Figure 1C:
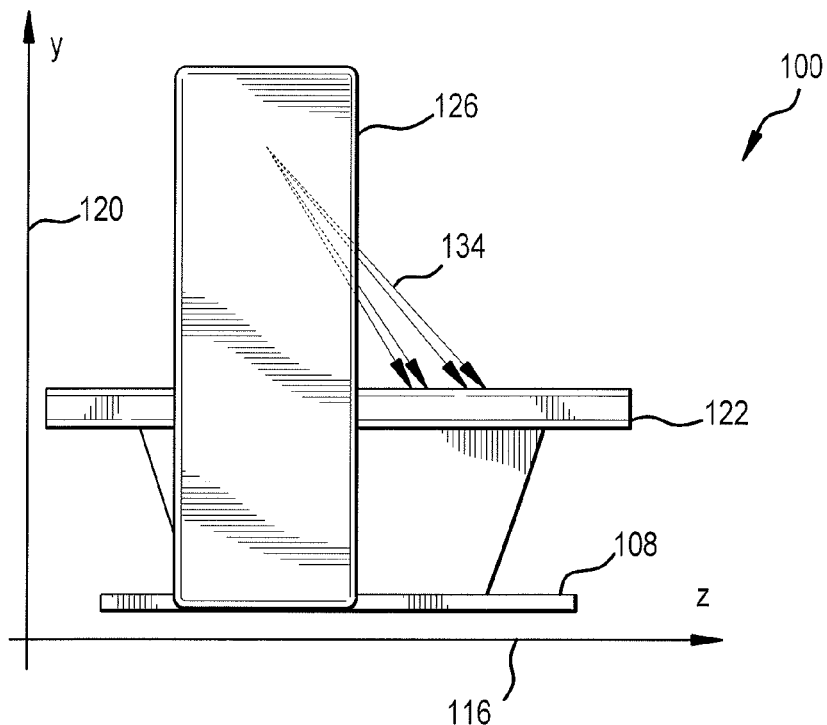
FIG. 1C is a side orthogonal view of the system of FIG. 1A.

FIG. 1B depicts a front view and FIG. 1C depicts a side view of system 100. Combined FIGS. 1A-1C show a longitudinal subject axis (z) 116, a lateral axis (x) 118 and a table-to-source axis (y) 120. Axis y' 122 (shown in FIG. 3) passes through the detector assembly 104 center of rotation and is orthogonal to a detector tray, e.g., rotatable tray 204, FIG. 2.

Figure 1D:
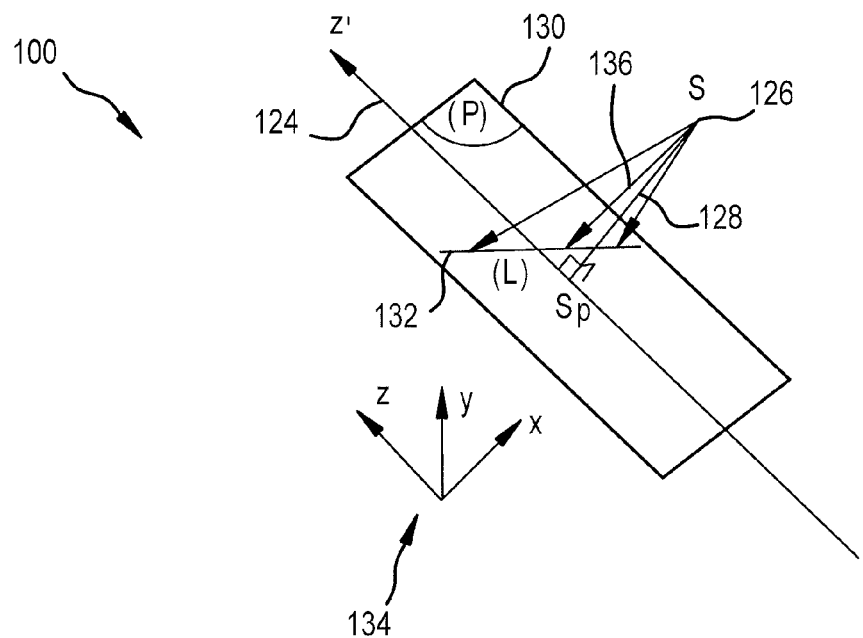
FIG. 1D is a geometric perspective view of the system of FIG. 1A.
Figure 10A:
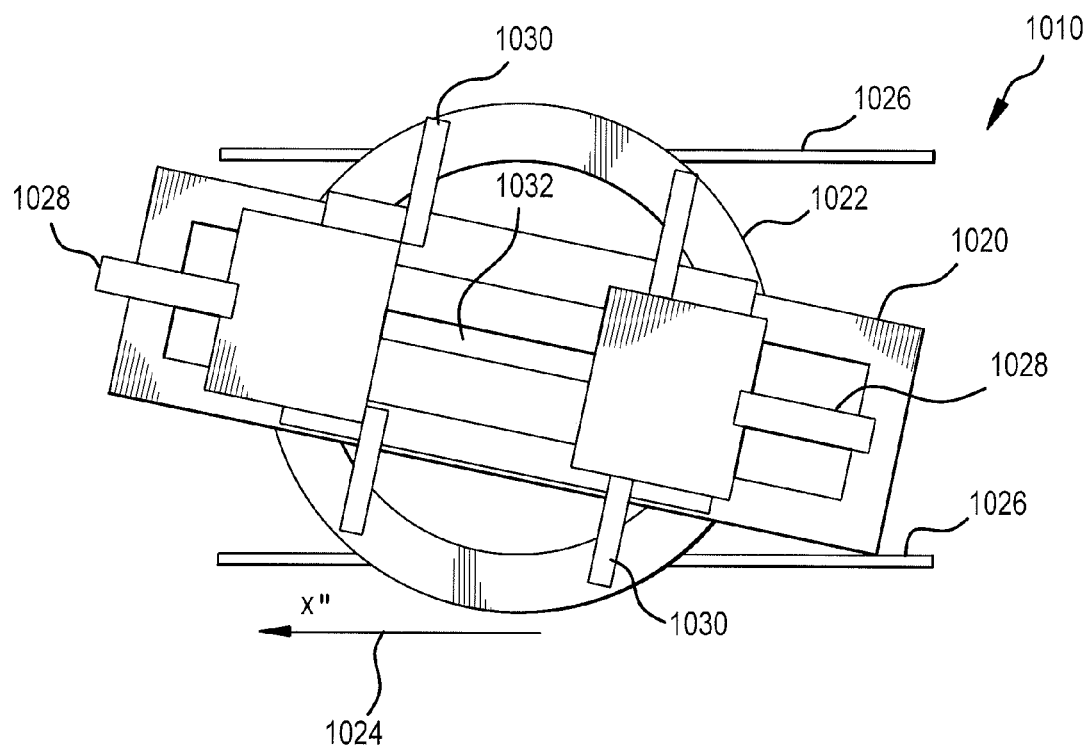
FIG. 10A provides a schematic view of a collimator assembly, in accordance with one embodiment.
Figure 10B:
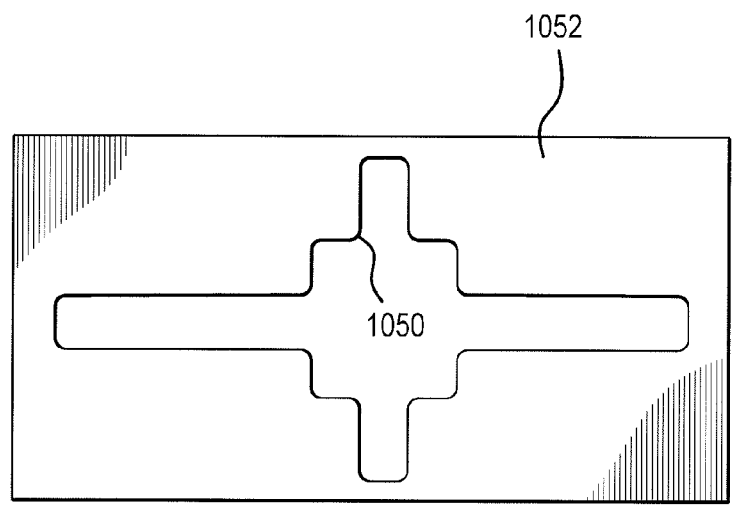
FIG. 10B illustrates adjustment of the shape of the collimator assembly of FIG. 10A, to reflect the arrangement of detector cells shown in FIG. 4B.

FIG. 1D is a perspective view illustrating exemplary geometry of system 100. An object or subject axis z' 124 is for example generally parallel to longitudinal axis 116, and passes through the object or subject's center of gravity. In the case of subject imaging, this axis 124 may be collinear with the subject's main axis of elongation. In the case of inanimate object imaging, the object axis is chosen by convention to be parallel to longitudinal axis 116 and passing through the object's center of gravity. The X-ray source, e.g., projection source (S) 126 is located at a point that does not belong to the chosen object axis, and is retained as defining the vertex of a geometric projection source. A projection direction 128 is then defined as the line passing by the projection source 126 and the object axis 124 and orthogonal to the object axis 124; projection plane 130 is then defined as the plane containing object axis 124 and orthogonal to the projection direction 128. Sp represents the orthogonal projection of source 126 upon plane 130. An X-ray beam as shaped and defined by a collimator assembly, described herein below with respect to FIG. 10, presents at least one defined main direction, corresponding to the most elongated beam dimension as projected onto the projection plane 130. The intersection of the elongate beam axis and projection plane 130 defines a line 132 on the projection plane 130. The aforementioned directions may be determined according to a fixed, or laboratory reference system 134. Further, an X-ray beam shaped and defined by a collimator assembly according to the principles laid out herein presents a beam central axis 136 passing through the source 126 and generally passing through the geometric center of the beam projection in plane 130 or in the plane of detector assembly 104. In practice, such a beam central axis may be chosen to correspond to the rotational axis of a rotating collimator assembly, for example as described herein below with respect to FIGS. 10A-10B and 14. The beam central axis may also be chosen to pass through the detector assembly 104 center of rotation. It is noted that, in general, the beam projection onto plane (P) does not include point $S_p$, nor does the X-ray beam necessarily include projection direction 128.

Figure 2:
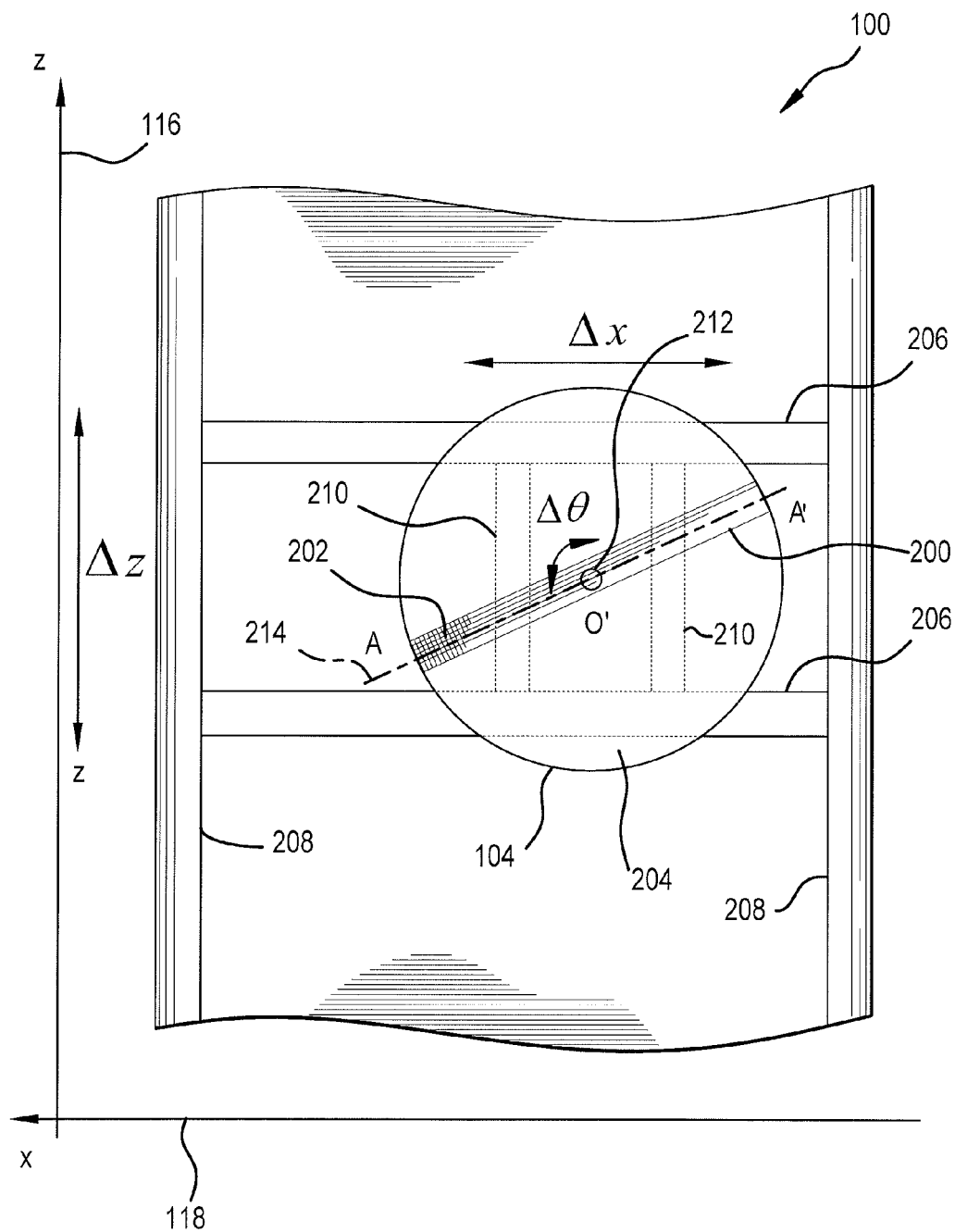
FIG. 2 schematically illustrates the moveable X-ray detector assembly shown in FIGS. 1A-1D.

As shown in FIG. 2, system 100 may provide a fast, full-frame sampling detector assembly, designed according to the principles disclosed herein. Detector assembly 104 for example includes a detector 200 having detector cells 202 arranged as a matrix, shown as having a rectangular shape. Detector 200 may mount on a moveable assembly, such as a detector tray 204, itself assembled on sets of rails 206 and 208 underneath or within a subject examination table (e.g., table 606, FIG. 6), which enable independent motion along two directions x and z. As shown in FIG. 2, detector tray 204 is circular; however, alternate shapes may be utilized in connection with detector 200.

Figure 3:
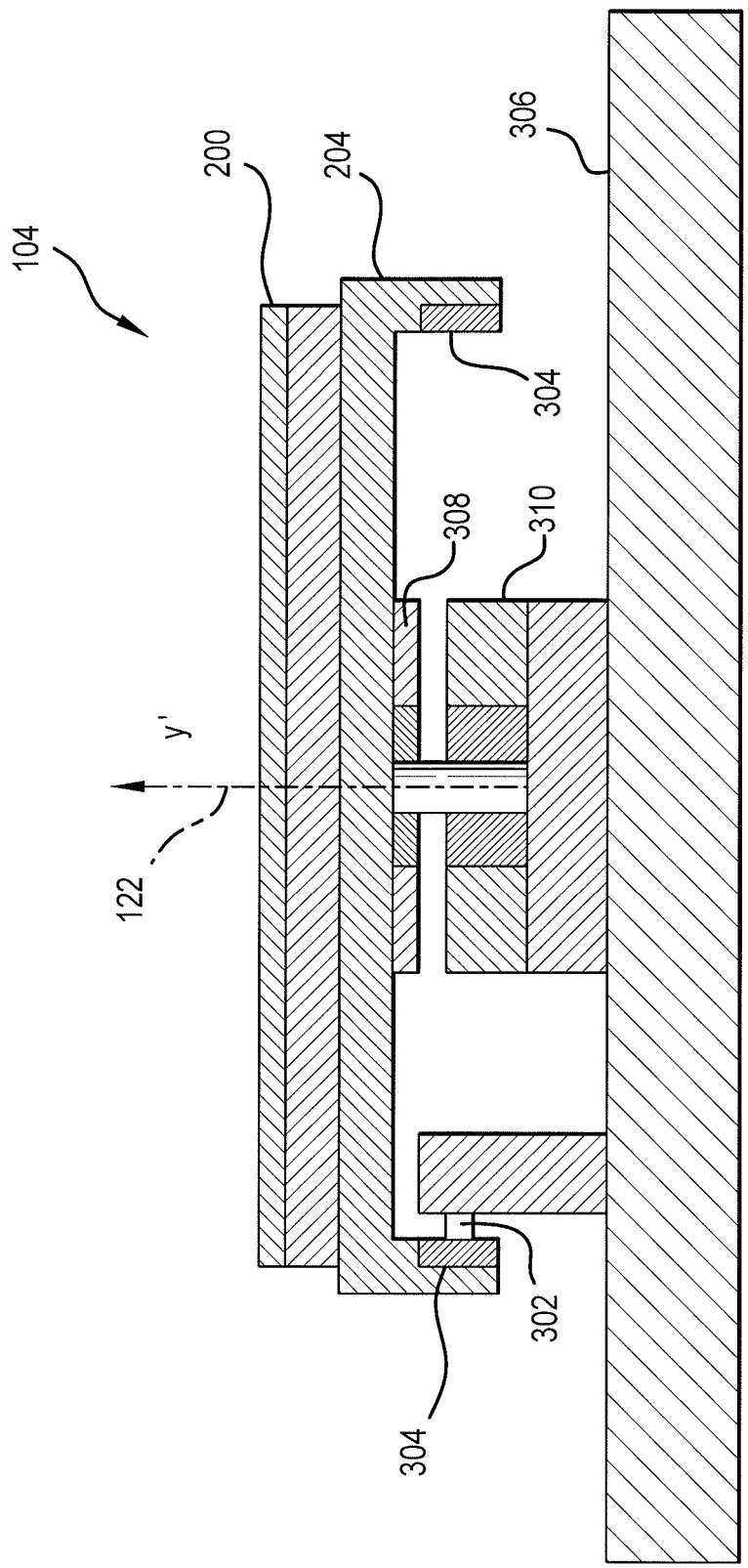
FIG. 3 is a cross-sectional view of a detector tray of the assembly of FIG. 2.

In the embodiment illustrated in FIG. 2, detector tray 204 has three degrees of freedom: (1) translation Δz along the longitudinal table/subject axis 116, (2) translation Δx along the orthogonal direction 118 in the plane of the subject table, and (3) rotation Δθ with respect to axis y' 122 (see FIG. 3), which is generally orthogonal to the plane of the subject table and generally in the direction of axis 120. These degrees of freedom may be activated independently, in combination, in turn or simultaneously. FIG. 2 illustrates part of the mechanical assembly that enables these motions. Detector tray 204 is mounted on an assembly (illustrated as two beams 210 parallel to axis 116). Beams 210 terminate at a system of wheels or similar translation structure, such as a slide or roller assembly (not shown) that allows motorized translation along rails 206, parallel to x axis 118. Rails 206 also terminate at a system of wheels or similar translation structure, such as a slide or roller assembly (not shown) that rolls on parallel rails 208, oriented parallel to z axis 116. Accordingly, the center or center of rotation O' 212 of detector tray 204 can be juxtaposed with any location within a plane (or upon a surface) that is generally parallel to the subject table, for example, image plane x O z, shown in FIG. 5 (subject to mechanical limitations on excursion ranges), by actuation of motors for translation along rails 206, 210 (motors not shown). Further, as shown in FIG. 3, detector tray 204 is mounted with a rotation axis y' 122 generally orthogonal to a plane that is locally tangent to the detector motion surface or plane (e.g., image plane x O z, FIG. 5). Detector tray 204 may freely rotate around axis 122.

FIG. 3 provides a cross-sectional view of detector assembly 104 along the line AA' 214 of FIG. 2. Line AA' passes through detector center 212 and is parallel to the elongate axis of detector 200, e.g., parallel to a plane including detector cells 202. Power is for example provided to detector 200 via a brush link 302 and a slip-ring 304 assembly, although it is understood that power provision may be accomplished using alternate components. Transmission of detector data between rotating tray 204 and a detector base 306 may be provided by a transmitter and receiver assembly, for example including transmit and receive elements 308, 310, which transmit detector data through radio-frequency (RF) signals. However, other known methods of data transfer, such as brush-link data transfer, may provide data transmission from rotating tray 204 to base 306 (and from base 306 to tray 204).

Detector base 306 is a non-rotating base, for example due to fixed mounting on a non-rotating portion of detector assembly 104. Transmit/receive elements 308, 310 may mount with rotating tray 204 and non-rotating detector base 306, respectively. The above-described combination of features facilitates unimpeded and unlimited rotation of detector tray 204 for any number of clockwise or counter-clockwise revolutions generally in the plane of the detector, and further enables transmission of power and data to and from detector assembly 104. Alternatively, and in other embodiments, detector motions may be restricted to two directions within a plane; or motion may be restricted to a single scan direction, either within a plane or along a curved path.

Figure 4A:
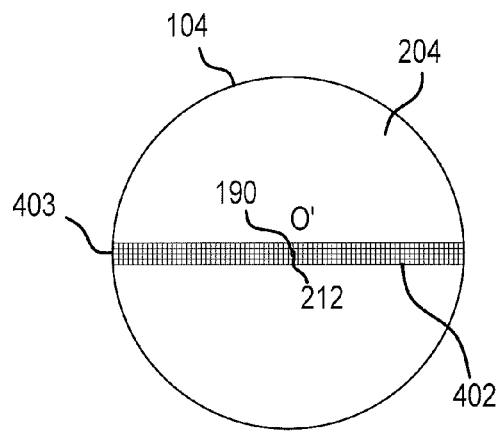
FIG. 4A illustrates a matrix of detector cells, in accordance with one embodiment.

FIGS. 4A-4D illustrate four of a number of possible detector cell arrangements upon detector tray 204. FIG. 4A shows a matrix of detector cells 402 arranged along a slot, as elongated rectangular matrix 403. In one embodiment, detector matrices are designed as a combination of square or rectangular detector modules that can be tiled along any dimension in a plane or surface. Current detector technologies allow design of such modules, possibly including backplane readout; with such an arrangement, the spacing or gap between adjacent detector modules can be reduced to a dimension less than or equal to that of the detector cell pitch.

Figure 4B:
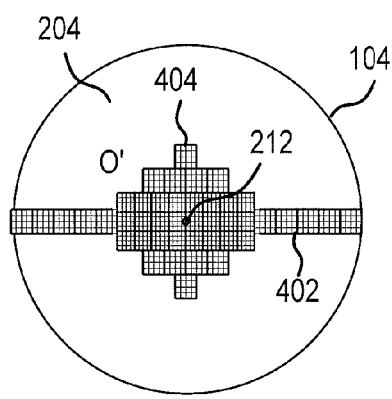
FIG. 4B shows the matrix of FIG. 4A, with an arrangement of detector modules.

FIG. 4A also shows the intersection 190 of an X-ray beam (not shown) central axis with the plane (e.g., image plane x O z, FIG. 5) of detector assembly 104. FIG. 4B shows rectangular matrix 403 of FIG. 4A with additional detector modules 404 provided near center of rotation 212. Such an arrangement, when properly matched by a source-collimator assembly, may provide effective trade-offs between the amount of area that is under continuous X-ray exposure and the areas more distal from center of rotation 212, which are exposed only twice for each full rotation of detector tray 104.

Figure 4C:
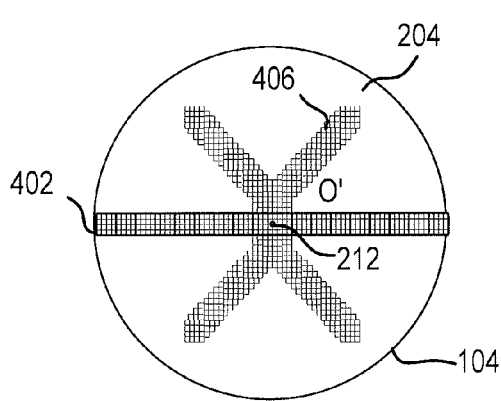
FIG. 4C shows the matrix of FIG. 4A, with a alternate arrangement of detector modules.
Figure 4D:
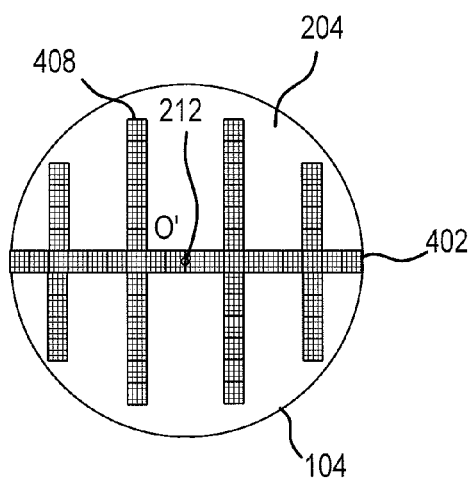
FIG. 4D illustrates the matrix of FIG. 4A, with another alternate arrangement of detector modules.

As shown in FIG. 4C, alternate (or additional) detector module arrays 406 may be provided. Arrays 406 for example have various widths, lengths and detector cell sizes, along with other variable design parameters, and may be generally arranged along a plurality of radial lines passing through center of rotation 212. FIG. 4D illustrates the use of four additional detector module arrays 408 arranged as lines that are for example matched to a multi-slot collimator assembly. Many other arrangements of module arrays 408, such as areas of varying widths, lengths and detector cell resolution, are possible and may be designed to optimize specific performance.

The fast, full-frame sampling detector allows refresh of the part of an image disk, such as a portion of the fixed image grid that is covered by tray 204, that is spatially coincident with a rotating detector at various rates. In one example of this, areas near rotation axis 122 may be refreshed at the intrinsic detector sample rate, while areas toward the periphery of the disk can be refreshed at a rate that is a function of detector sample rate, detector angular velocity, and detector cell arrangement. This flexibility facilitates relatively slow refresh of the outer part of an image, while faster refresh is provided at and near the image center, thus achieving an overall reduction in dose.

In an interventional procedure using a catheter, for example, the faster refresh at the image center allows a physician to focus clearly on and see movement of the catheter tip. The refresh rate at the image periphery is for example sufficient to provide landmark data for navigation, while still reducing overall dose to the patient, physician and any attending staff. Dose is reduced because at any given time, a much smaller total area is exposed to radiation as compared with conventional fluoroscopy procedures. Further, as a Bucky grid is not necessary when using a beam covering a reduced area, another two-fold dose reduction may be realized because the delivered dose does not have to be increased to compensate for Bucky grid absorption.

An X-ray source filter (not shown) can be shaped to provide proportionally increased flux towards the extremities of the detector matrix (e.g., detector matrix 403) so that upon continuous rotation, the X-ray dose to various areas of an image disk can be further modulated, by design. In such an embodiment, the filter, located on the tube side of the imaging chain, provides more X-ray attenuation at the image center, and gradually less attenuation towards the side ends of the X-ray beam. Alternatively, the filter may be made of materials with essentially uniform attenuation properties. In other embodiments, such as those employing a plurality of detector lines or areas, the filter can be designed to essentially match the detector shape. Furthermore, different filter properties may be used for each of the corresponding detector areas or lines, therefore providing for simultaneous multi-spectral imaging. In a simple example with a detector array comprising two orthogonal rectangular cell arrays, one of the rectangular detector areas could be illuminated by a high energy beam, while the second rectangular area would be imaged by a low energy beam.

Figure 5:
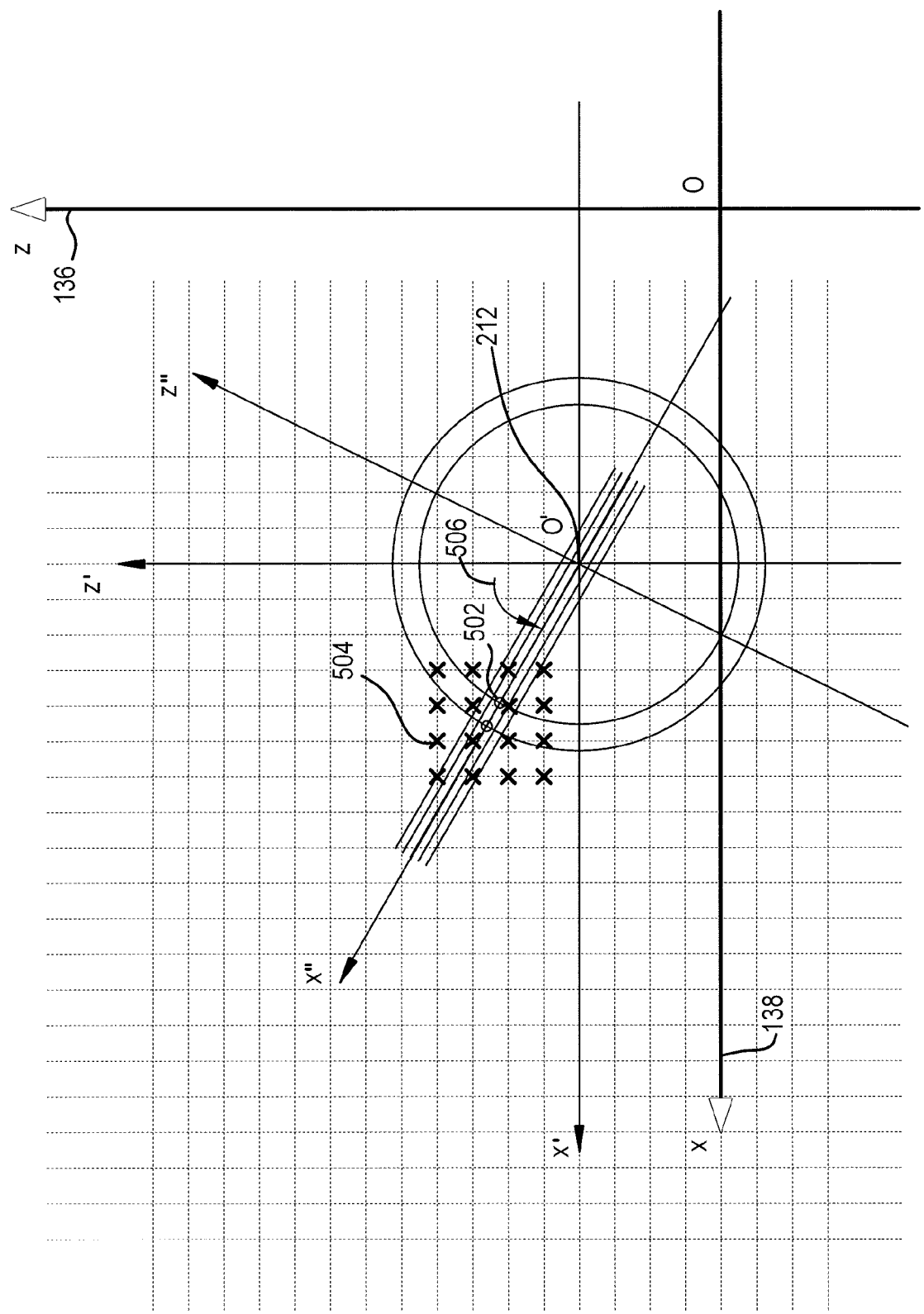
FIG. 5 is a grid illustrating the relationship between X-ray detector samples and image grid points, in accordance with one embodiment.

FIG. 5 illustrates the relationship between detector samples 502 and image grid points 504. In a general case, a given detector sample contributes to a number of image grid samples in a local neighborhood. A number of algorithms have been described, such as the "gridding" algorithm first used in astronomy, that allow efficient interpolation and distribution of the detector samples to the image grid samples. As is seen from FIG. 5, in a general case, center of rotation 212 corresponds to the origin of the referential (x" O z") associated with the moving detector. The origin may be on any point with respect to the table or image plane (x O z), and rotation angle θ 506 may take any value.

Figure 6:
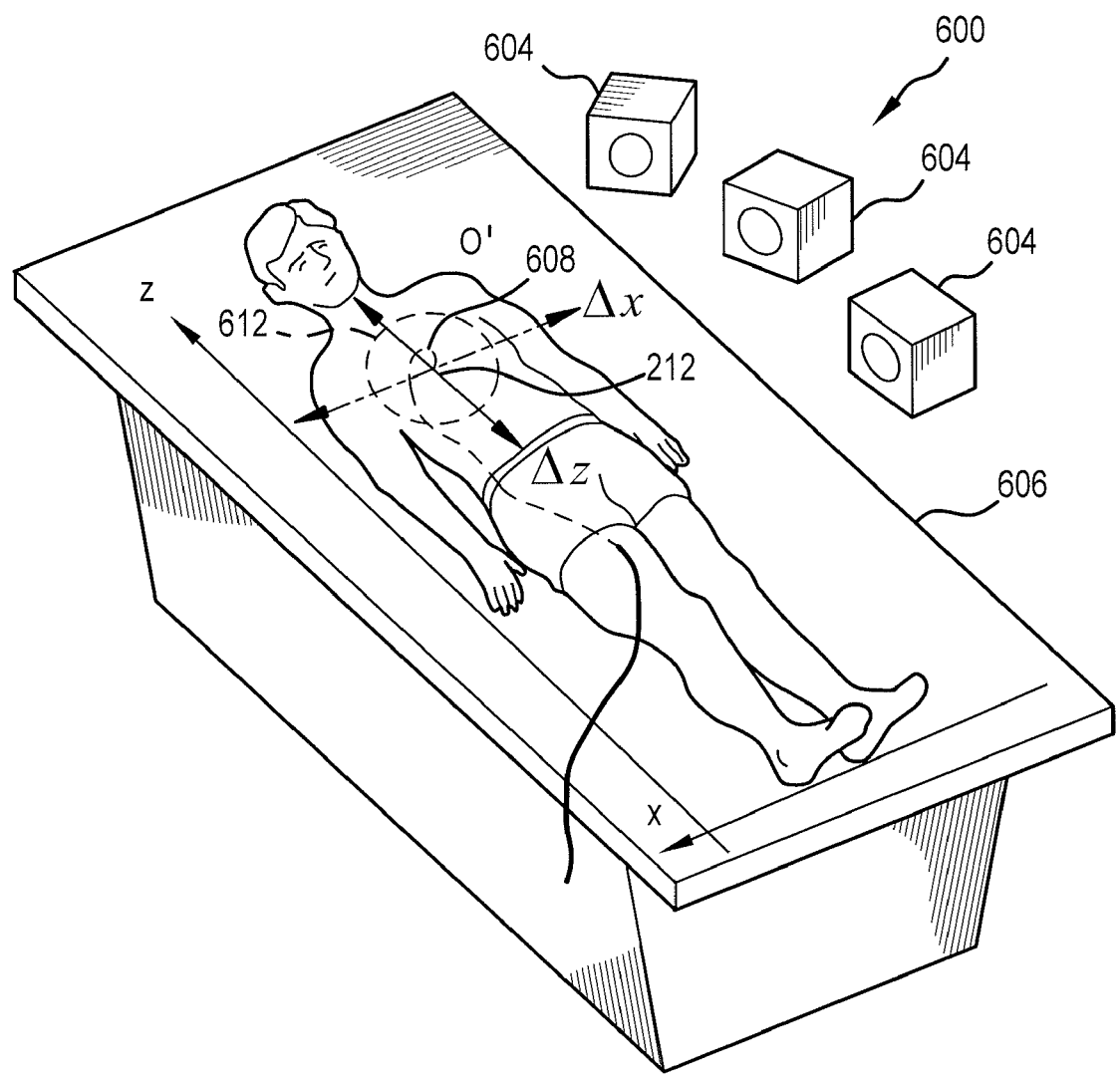
FIG. 6 illustrates the use of a dynamic, low-dose X-ray imaging system with real-time interventional device localization, in accordance with one embodiment.

FIG. 6 illustrates the use of a real-time interventional device localization system 600 together with the dynamic X-ray system described herein above. In one embodiment, three radio-frequency emitters/receivers 604 (not to scale) are placed adjacent a subject table 606 and in such an arrangement as to provide sufficient signal separation for accurate three-dimensional device tip localization. A small assembly 608, for example having three coils, is contained within a device tip (which is for example within region of interest 612, shown bounded by a dotted circle). Analysis of the signals thus received at one or a multiplicity of frequencies permits accurate, real-time localization of the device tip with respect to the table coordinate system, as known in the art. This localization information is fed-back in real-time to the dynamic X-ray imaging system (e.g., system 100), and adjustments are dynamically made to the detector tray position (e.g., tray 104 position), X-ray tube column position (e.g., column 106 position), X-ray tube angle (e.g., tube 110 angle), and X-ray collimator assembly position (e.g., assembly 1010 position), as necessary to track the progress of the device tip with the X-ray beam.

Further adjustments to detector raster mode, location and rotation may be made as necessary to enable dynamic tracking of the device tip. Scanning modes include translation of the detector along either the direction parallel to or the direction orthogonal to the short axis of the detector cell matrix (e.g., in directions z" or x" of FIG. 5); combinations of parallel and orthogonal translations; rotation of the detector with respect to center of rotation axis 122, and combinations of rotation and translation motions of the detector tray within the plane of the detector assembly.

In a specific imaging mode, and for illustration, it might be desirable to ensure that the center 212 of detector tray 204 is always positioned with respect to table 606 and the system X-ray tube (e.g., tube 110) in such a manner that the X-ray shadow of the device tip projects onto center 212. Tracking may rely on automatic device tip detection in the projection image, motion of the detector assembly and/or motions of the X-ray imaging chain. A dynamic fluoroscopic image is obtained by simultaneously rotating tray 204 with respect to its instantaneous center, rotating the collimator assembly in synchronicity with the rotating tray 204, and/or translating and/or rotating the collimator across the X-ray port and/or rotating the X-ray tube, for acquiring X-ray data. Synchronicity between the tray and the collimator may be provided mechanically, by design, or through a feedback loop and sensing of relative motion of the X-ray beam with respect to the detector, for example feedback from pixels radiated by the beam penumbra may indicate misalignment between the tray and collimator.

Other applications and modes of implementation are also possible. X-ray data acquisition may be performed in either a pulsed or a continuous mode. In addition, other device or object localization systems or instruments may be employed with system 100.

Figure 7:
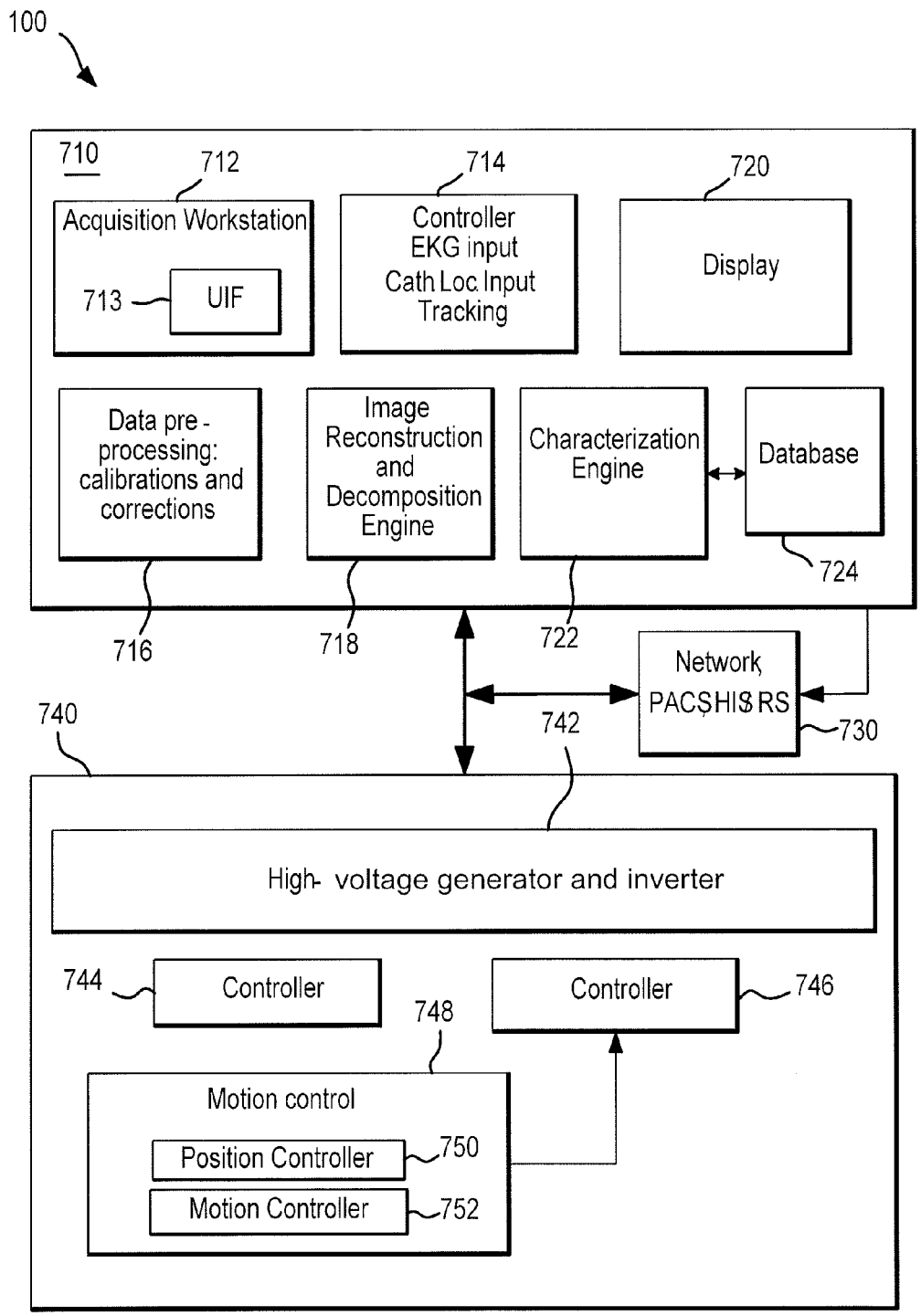
FIG. 7 is a block diagram showing one embodiment of a system for dynamic low dose X-ray imaging.

FIG. 7 presents a block diagram showing system components. The system comprises an image acquisition and review workstation 710, an interface to a hospital or imaging network 730, and a gantry 740. The image acquisition and review workstation 710 has an acquisition workstation 712 with a graphical user interface (UIF) 713; a controller 714 which receives inputs from external devices such as an EKG and/or a device localization system, and drives X-ray emission, acquisition, system motions, and tracking; a data-preprocessing computer architecture 716 for data calibrations and corrections; an image reconstruction and decomposition engine 718; an image display 720; and, for specific application, a feature detection and characterization engine 722 interfacing to a database 724.

The gantry 740 includes: a high-voltage generator and inverter 742 for the generation of time-varying kVp and mA waveforms; a controller 744 for the selection of an anode track and control of X-ray sources and X-ray focal spot parameters (the selection and control of which may vary as a function of time); a controller 746 for the activation of X-ray filters and collimation devices (such action also variable as a function of time); a motion control architecture 748 which itself comprises a controller 750 for the subject, detector cradle, and X-ray tube column positioning and a controller 752 for the motions of the detector assembly (e.g., along z, x axes 118, 116 and rotation $\Delta\theta$ about axis 122).

Figure 8:
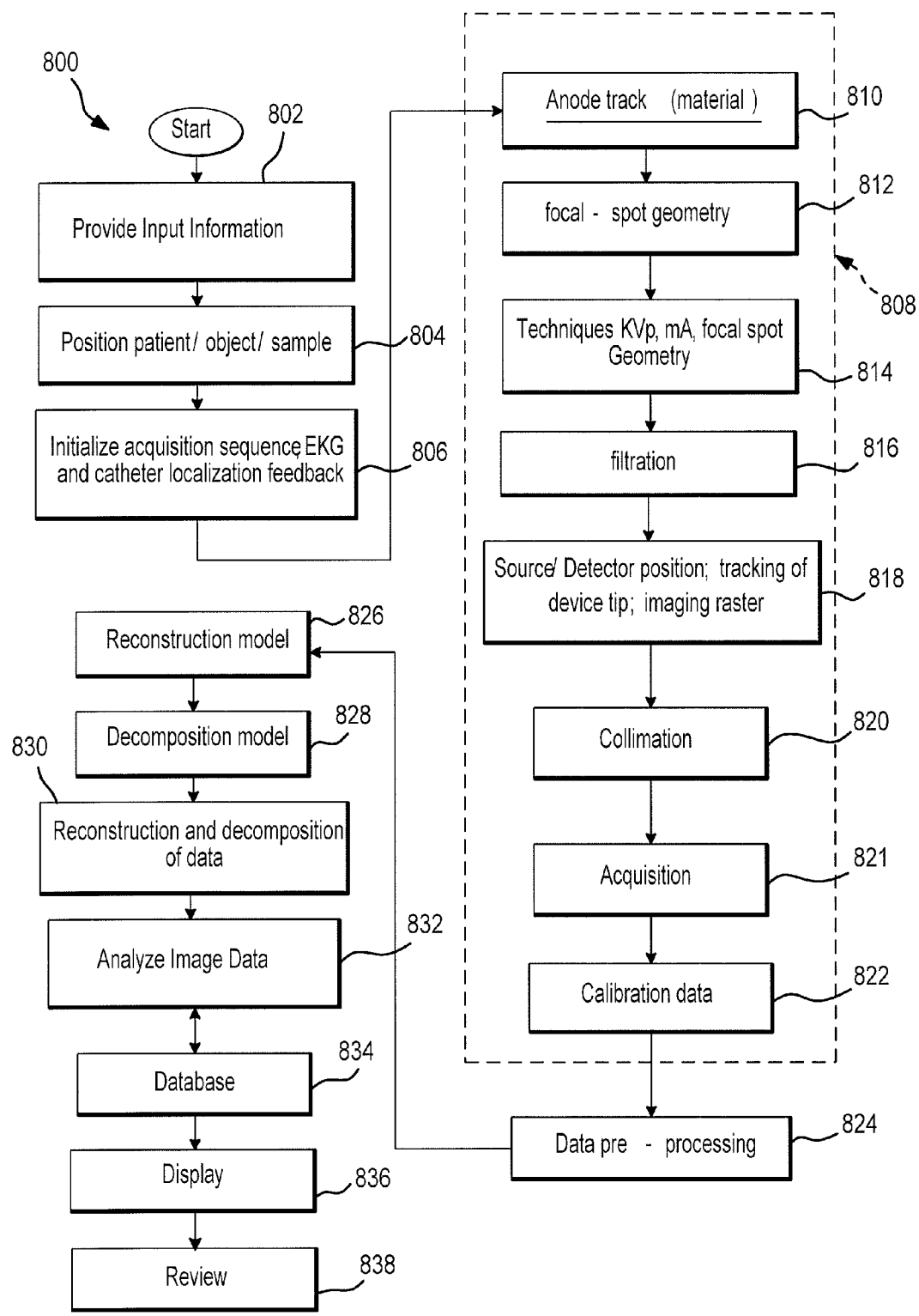
FIG. 8 is a flow chart illustrating data acquisition in a method for dynamic low dose X-ray imaging, in accordance with one embodiment.

FIG. 8 shows an exemplary data acquisition sequence 800. Following startup of the sequence, the user provides input information relating to the subject/object to be imaged, and type of data acquisition sequence to be performed, in step 802. Step 802 for example includes selection of acquisition parameters and input of body information at graphical UIF 713, of FIG. 7. The subject/object is then positioned, in step 804. The acquisition sequence and EKG and device localization feedback are initialized in step 806. Feedback from an EKG and/or feedback from device localization inputs may occur in essentially real time, or data acquisition may proceed according to a pre-determined imaging sequence.

The synchronized acquisition sequence (indicated by dotted box 808) controls selection of spectra, including selection of: an anode track, in step 810; a focal spot geometry, in step 812; X-ray techniques, for example selection of KVp or mA waveforms, in step 814, and filtration, in step 816. The X-ray source and detector assembly are set in motion, in step 818, for example to perform a specific series of image acquisition sequence, to generate a particular imaging raster, or to dynamically track an interventional device tip such as a catheter, sheath, guide wire or other interventional object such as a biopsy needle or a radiation seed implant, e.g., in brachytherapy applications. Collimator controls are activated to dynamically track the detector location and orientation or to perform a specified acquisition sequence, in step 820. Collimator controls are for example activated as a function of body position of a subject upon a subject table, and/or other acquisition parameters. Data is acquired, in step 821, and calibration data is gathered, in step 822. Acquired data (gathered in step 821) is pre-processed, using the calibration data, in step 824. Calibrations and pre-processing is for example performed by computer architecture 716.

An image reconstruction model is generated, in step 826, and an image decomposition model is generated, in step 828. Image reconstruction and decomposition is performed using the reconstruction and decomposition models of steps 826, 828, for example by image reconstruction and decomposition engine 718, in step 830. As may be desirable, the image data are automatically analyzed by a CAD engine, in step 832. The CAD engine, e.g., characterization engine 722, for example provides automatic detection, characterization, and classification of features by data processing and/or by accessing a database, in step 834. Acquired images are then displayed, in step 836, and reviewed, in step 838. A user for example provides inputs via UIF 713 as necessary, for image review.

Figure 9:
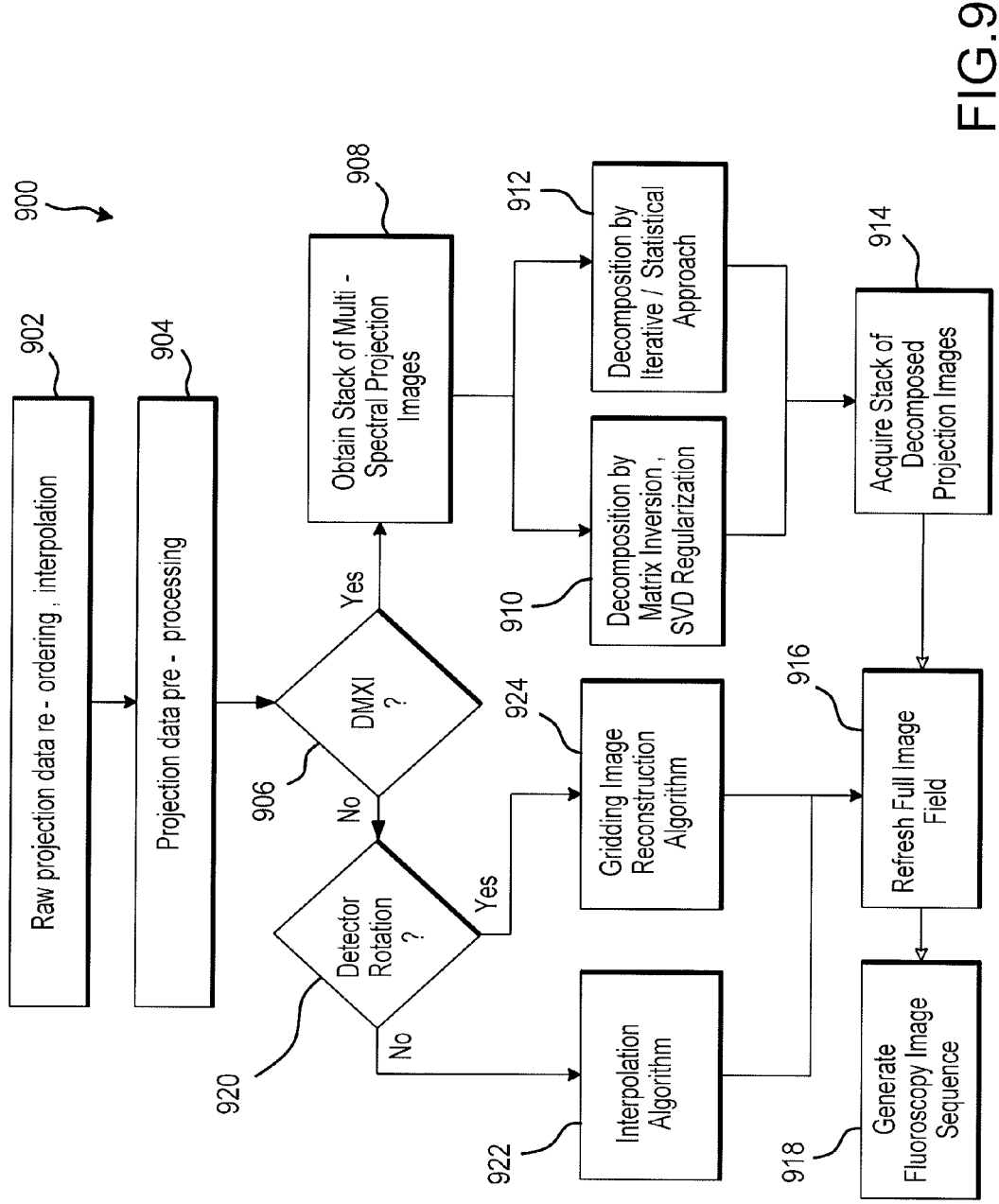
FIG. 9 is a flow chart illustrating image processing and reconstruction in a method for dynamic low dose X-ray imaging, in accordance with one embodiment.

FIG. 9 details a method 900 for image reconstruction using an image reconstruction algorithm, e.g., as performed by engine 718, FIG. 7. Raw projection data are re-ordered and interpolated (if necessary depending on the specifics of the data acquisition sequence), in step 902. Following pre-processing of projection data, in step 904, the algorithm proceeds to image generation. Image generation commences with a determination of whether or not Dynamic Multispectral X-ray Imaging (DMXI) is used, decision 906. In the case of a DMXI image acquisition sequence, a stack of multispectral projection images is obtained, in step 908. These images are decomposed using either a matrix inversion approach, step 910, or an iterative approach, step 912. A stack of decomposed projection images is acquired (via step 910 or 912), in step 914. The acquired images are then used to refresh the full field image, in step 916, thus providing a fluoroscopy or radiography image sequence, step 918.

Alternatively, when DMXI is not used according to decision 906, a further case differentiation is made depending upon rotation of the detector tray, in decision 920. If the detector tray is not rotating, but translating (with the detector tray in an arbitrary angle), various simpler interpolation algorithms may be employed to dynamically build and refresh the full field image, e.g., by interpolating the detector raster to image grid, in step 922. The full field image is refreshed, step 916, and the fluoroscopic or radiographic image sequence generated, in step 918. Alternately, if the detector tray is rotating, decision 920, a more complex interpolation algorithm, such as a gridding algorithm, is employed, in step 924, for image field refresh, step 916, and generation of a fluoroscopic or radiographic image sequence, step 918. The choice of X-ray techniques as well as image frame rate contributes to the distinction between fluoroscopic and radiographic sequences.

FIG. 10A schematically shows one embodiment of a collimator assembly 1010. A collimator 1020 is mounted on a rotatable ring 1022. Such ring can also be translated along an axis x" 1024, by rolling along two rails 1026 parallel to x". A system of collimator blades such as independently adjustable sets of blades 1028 and 1030 mount with the rotatable part of the collimator. Collimator blades 1028 and 1030 open or close along their respective axes, for example to effect an aperture 1032 and an aperture 1032 location that allow a narrow X-ray beam to be generated and to project onto a detector (e.g., detector assembly 104) for any position and/or orientation of the detector. A beam of specific shape, such as a beam including a number of fans (with or without a central wide area), may also be defined by blades 1028 and 1030 as subjected to suitable modifications (not shown). The shaped beam is then translated or rotated across the face of a large area detector or in synchronicity with the motion of a detector of specific shape.

In one embodiment, the shape of the X-ray beam is adjusted to reflect a specific arrangement of detector cells. FIG. 10B shows an aperture 1050 shaped to match the arrangement of cells 402, 404 in FIG. 4B. Aperture 1050 is defined for example by an aperture plate 1052; however, aperture 1050 may also be defined by combining plate 1052 with blades 1028, 1030. Aperture 1050 size and shape may thus be controlled by any one of blades 1028, blades 1030 and aperture plate 1052, or by any combination of blades 1028, 1030 and plate 1052.

To allow a continuous rotation mode, power is provided to the rotatable part of collimator assembly 1010, for example through a slip-ring and brush design (see, e.g., brush link 302 and a slip-ring 304 assembly, FIG. 3). Collimator assembly 1010 includes a filter (not shown), which may include filter materials of various attenuation and X-ray energy filtration properties. In one embodiment, filter attenuation varies from the center to the sides of collimator 1020; in another embodiment, different filters may be provided for each of the different areas of the collimator aperture 1050. Simplified collimator embodiments are also provided by use of an aperture plate 1052, providing for beam formation in a shape matching that of the detector cells such that variations in the projection imaging geometry during an imaging sequence are accounted for. For example, plate 1052 may ensure that a maximum beam width remains less than the width of the associated active detector array. The combination of X-ray aperture, collimator and filter shapes the X-ray beam both spatially and spectrally, as is known in the art. Shaping may also be accomplished using only an aperture and a filter, a collimator and a filter, or a lone collimator.

Dynamically adjustable blades 1028, 1030 may provide a beam of specific width that in typical operation always projects onto the X-ray detector. Further, the width and position of the X-ray beam with respect to the detector matrix may be dynamically adjusted during the image acquisition sequence. This width adjustment, in particular, provides further control of the X-ray dose and noise properties of the image. Analysis of the full-frame data enables tracking of the beam umbra and penumbra onto the active detector. The location and orientation of the beam with respect to the detector as a function of time, for example, allows computerized, automatic prediction of necessary imaging chain (X-ray tube, collimator, and detector) adjustments to either track the detector for a given imaging sequence, and/or to track a moving point such as the tip of an interventional device.

Accordingly, detector motion may be tracked in real time based on detected X-ray profile information and/or instantaneous detector coordinate information. Tracking is for example achieved by a combination of the following motions: relative advance of the subject table with respect to the X-ray column, either by table motion or X-ray column motion; X-ray tube pivoting; collimator translations, for example along pivot axis 112, FIG. 1A and/or along an axis generally orthogonal to axis 112 (not shown); collimator rotation, and collimator blades adjustment (both with respect to the width and length of the collimator-defined aperture). In one embodiment, a specific raster and rotation sequence is programmed into both the detector tray controls and into the X-ray tube and collimator assembly controls.

By these instrumentalities, the X-ray beam is spatially shaped to match at least part of the moving detector, in the sense that part of the active detector is illuminated by the beam umbra (largest intensity), and the beam penumbra (or area of drop in intensity) is also imaged by the active detector. For a detector of given shape, the collimator may be adjusted such that the X-ray beam illuminates only part of the detector, For example, if a detector has an elongated array with additional cells along a second, generally elongated array, the collimator may be adjusted such that the X-ray beam illuminates only one of the two elongated arrays. Many other geometries are possible for both the detector and the collimator, as guided by the choice of X-ray imaging sequence and application type.

FIG. 11 illustrates one embodiment of a system 1100 for dynamic, low-dose X-ray imaging utilizing an additional degree of freedom. A subject-supporting table 1110 is adjustable via mechanical actuators 1112, allowing positioning of table 1110 with respect to detector cradle 102. This feature provides for variable geometry and variable magnification of a subject onto a detector plane. Both cradle 102 and subject table 1110 elevation along axis 120 can be adjusted via a cradle support 1114 and corresponding actuators (not shown).

Figure 12:
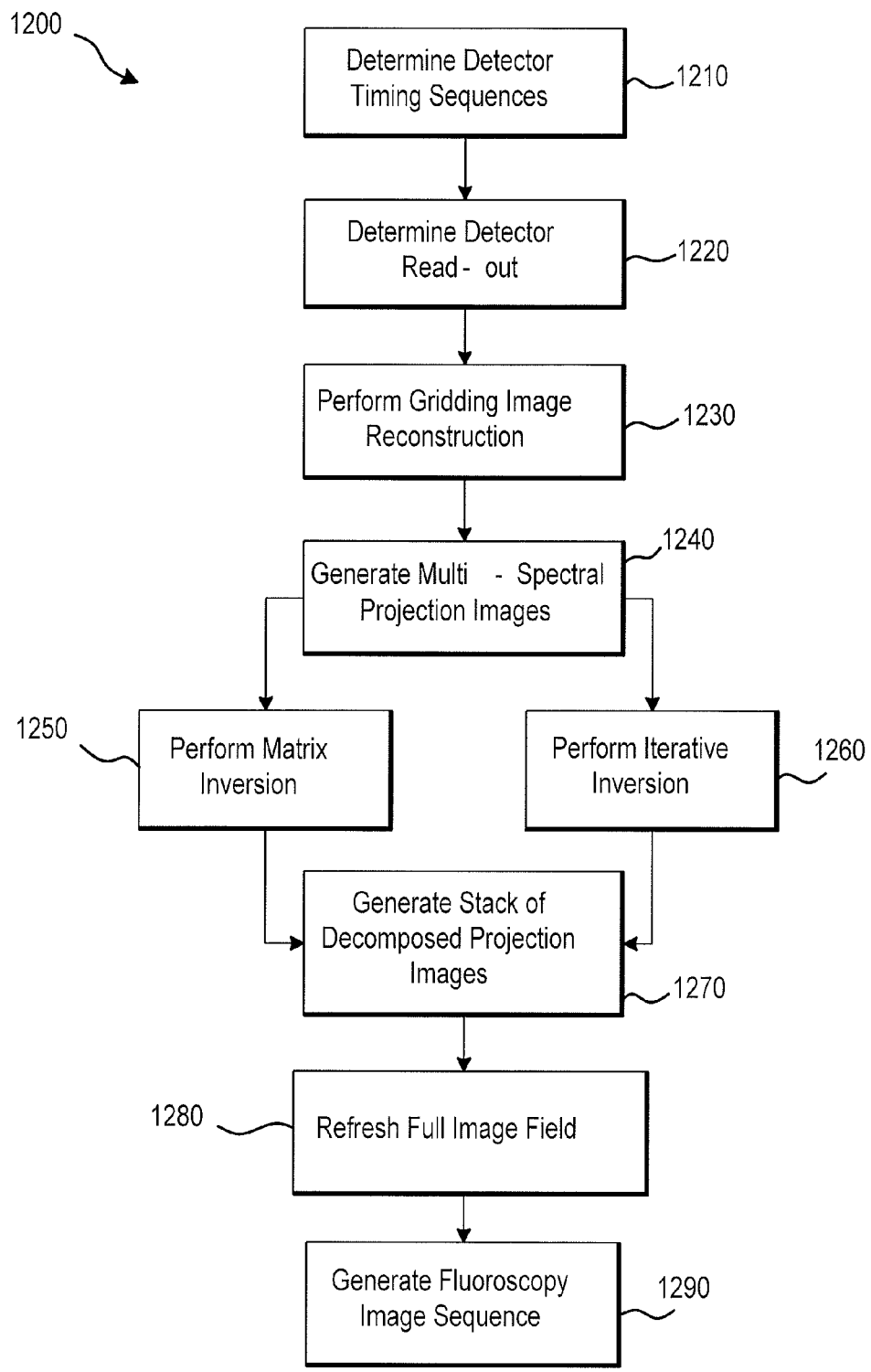
FIG. 12 is a flow chart illustrating an image acquisition sequence of a method for dynamic low dose X-ray imaging, in accordance with one embodiment.

In one embodied image acquisition mode, both dynamic multi-spectral X-ray imaging (DMXI) acquisition and detector tray rotation occur simultaneously. FIG. 12 illustrates a corresponding method for image acquisition. Method 1200 is for example governed by an image acquisition algorithm. Each array or array cell may be subject to variable timing, depending on the specifics of a given acquisition sequence as well as location within the detector. Such variable timing may include both offsets and sample times. Thus, detector timing sequences are determined, in step 1210. Data read-out for each column of the utilized detector array is independently determined, based on image acquisition sequence parameters and detector rotation, in step 1220. Gridding image reconstruction (or similar interpolation method) is performed for the acquired frames, in step 1230. A stack of multispectral projection images is generated, in step 1240. These projection images are input to a decomposition algorithm that performs either a matrix inversion or similar analytical decomposition (e.g., SVD regularization), in step 1250, or an iterative inversion, in step 1260. Accordingly, a stack of decomposed projection images is generated, in step 1270. The acquired decomposed images are then used to refresh the full field image, in step 1280, and to generate a fluoroscopy or radiography image sequence, in step 1290.

Figure 13:
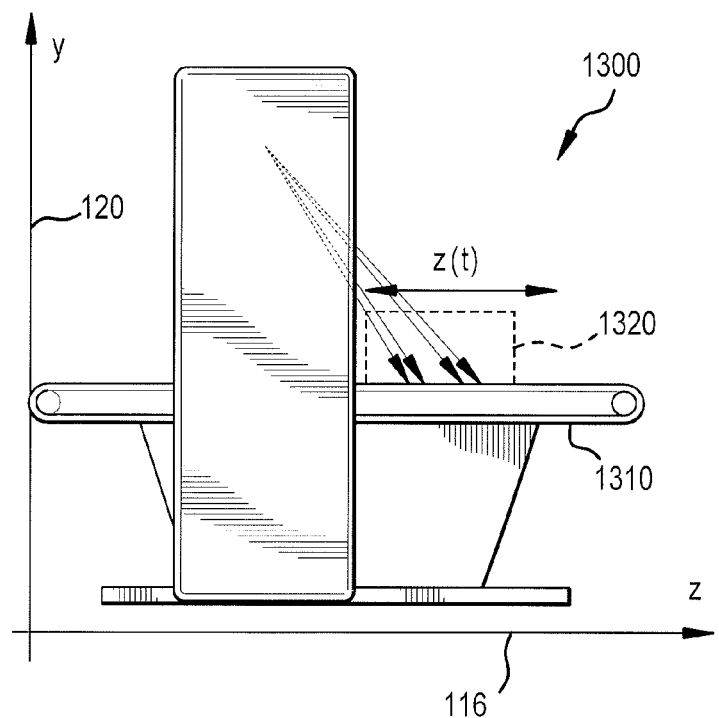
FIG. 13 illustrates parcel or container imaging with a system for dynamic low dose X-ray imaging.

FIG. 13 illustrates use of a system for dynamic, low-dose X-ray imaging for imaging of parcels, inspection of parts, imaging of containers and the like. In one embodiment, system 1300 includes a conveyor belt 1310 for transporting a parcel 1320 to be imaged. Acquisition of a multiplicity of projections of the same object may be facilitated by simultaneous translation of the X-ray tube column along, for example, z axis 116.

Figure 14A:
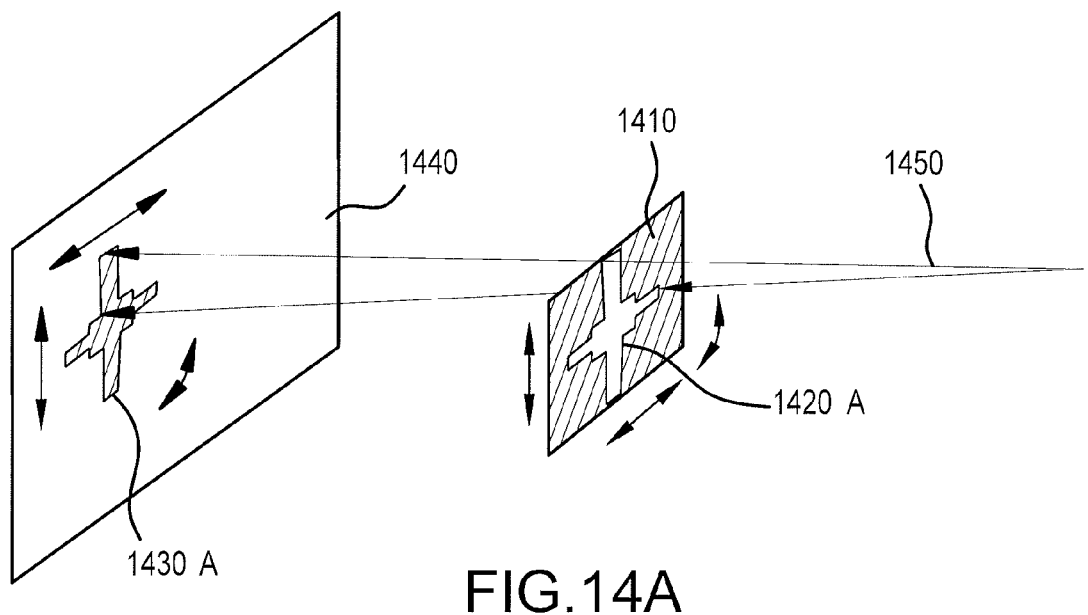
FIG. 14A shows a collimator aperture for use in projecting an X-ray beam of a specific shape onto an X-ray detector, in accordance with one embodiment.
Figure 14B:
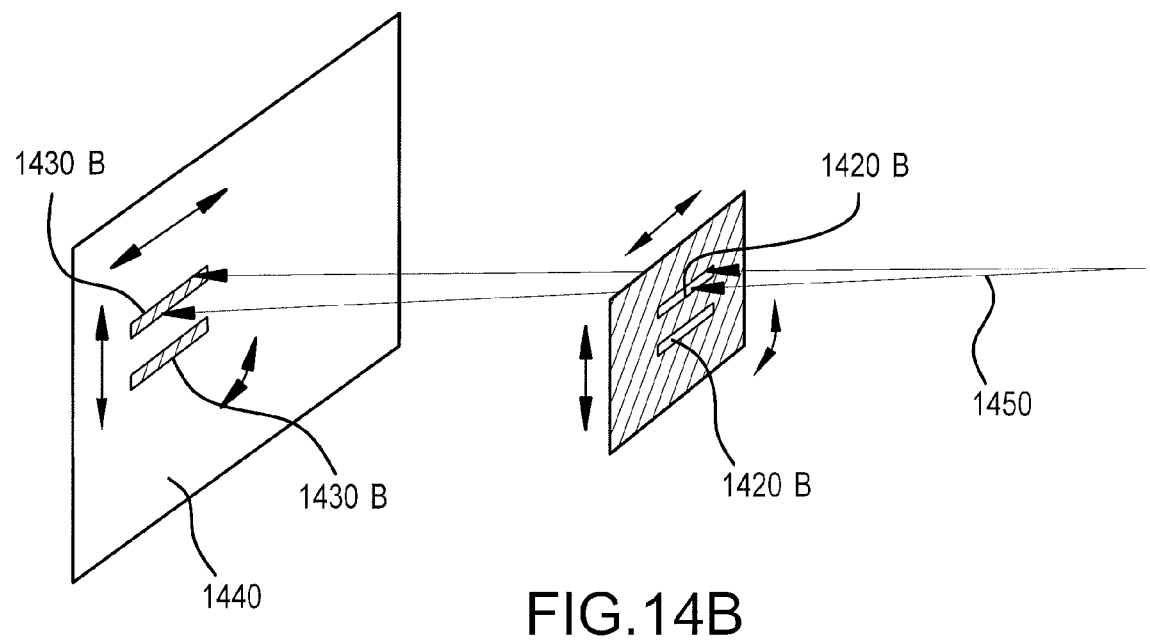
FIG. 14B shows a collimator aperture for use in projecting an X-ray beam of another specific shape onto an X-ray detector, in accordance with one embodiment.

FIGS. 14A-14B depict a collimator assembly 1410 with collimator apertures 1420A, 1420B and collimator blades (not shown), shapes a beam to a specific shape 1430A, 1430B as projected onto a detector 1440. The beam 1450 is scanned and/or rotated across the face of detector 1430, which is for example a two-dimensional detector. Data is read out of detector 1440 either in a raster fashion or, as possible with newer technologies such as CMOS design, read-out of predetermined areas in a specific sequence. FIGS. 14A and 14B present two embodiments for two specific X-ray beam shapes.

Figure 15A:
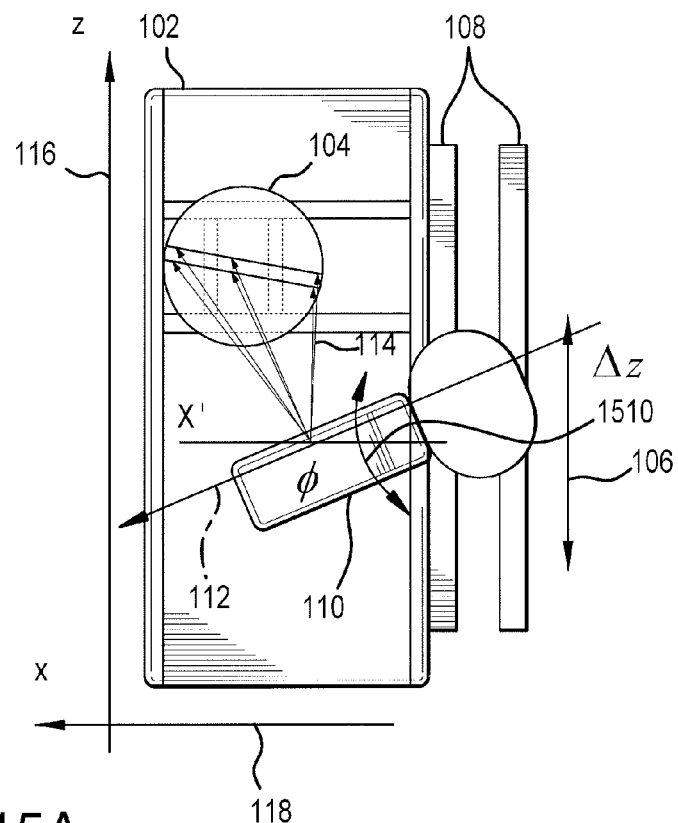
FIG. 15A illustrates rotation of an X-ray column with respect to a rotation axis, in accordance with one embodiment.
Figure 15B:
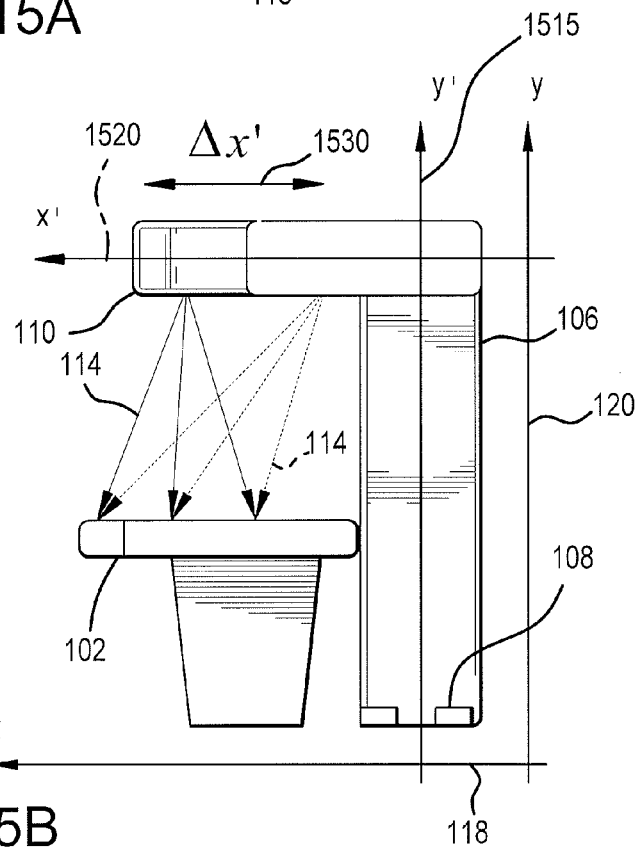
FIG. 15B illustrates motion of an X-ray beam along an axis parallel to a long axis of an X-ray tube, in accordance with one embodiment.
Figure 15C:
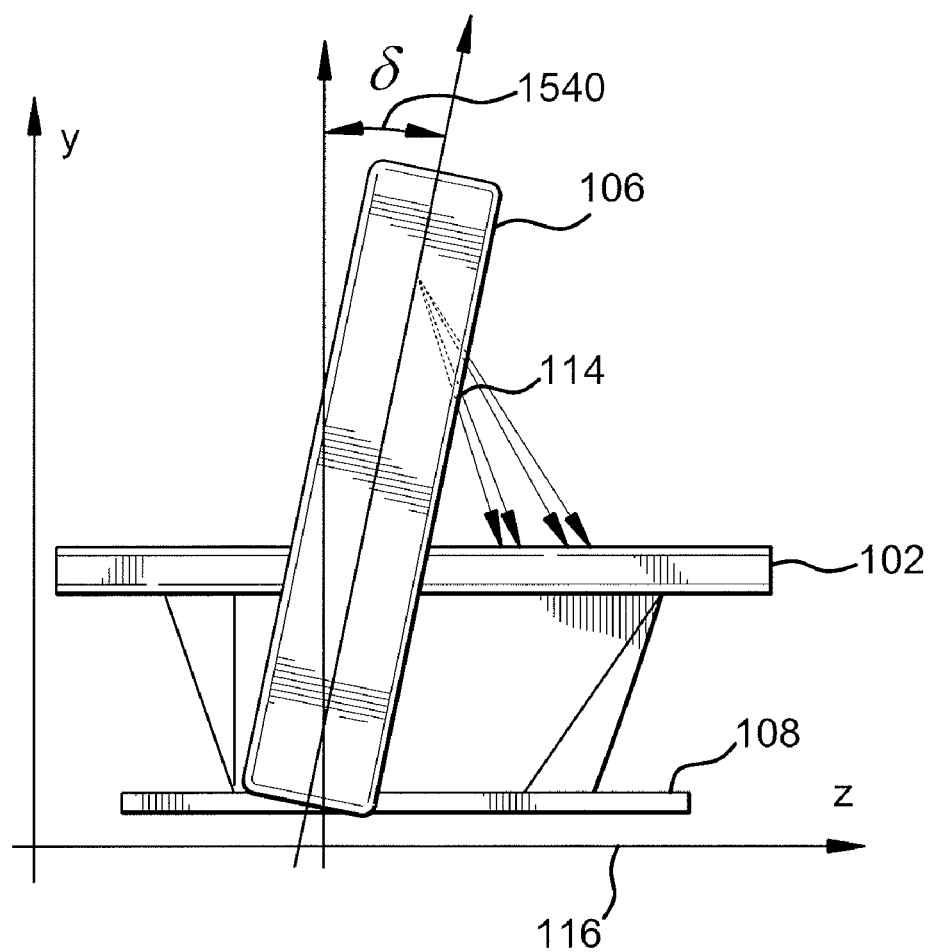
FIG. 15C shows rotation of an angle δ of an X-ray column, in accordance with one embodiment.

FIGS. 15A-15C schematically present a set of detector motions with respect to a number of axes. Tomosynthesis or limited-angle tomographic imaging may be enabled by moving a detector of specific shape along motion axes of FIGS. 15A-15C, while simultaneously moving the X-ray source along motion axes of FIGS. 15A-15C and shaping an X-ray beam to track the location and motion of the detector. Alternately, one or both of the X-ray source and detector may remain stationary during all or part of the imaging sequence. Where both the source and detector are stationary, an object to be imaged may move through an X-ray beam emitting from source to detector. For example, an object such as a suitcase moving along a conveyor belt may pass through the beam generated by stationary column assembly 106. Such an embodiment may find particular use in security screening applications, such as airport security or customs inspections.

In particular, FIG. 15A illustrates rotation of X-ray tube column assembly 106 by an angle φ 1510 with respect to rotation axis y' 1515 shown in FIG. 15B. FIG. 15B in turn presents motion of tube column assembly 106 along axis x' 1520 essentially including the X-ray tube 110 long axis. A displacement Δx' 1530 enables acquisition of a multiplicity of projections at various angles. Column assembly 106 (or X-ray tube 110) may rotate to track motion of an associated detector, e.g., detector 200. Alternately, column assembly 106 may remain stationary while detector 200 rotates, for example upon tray 204. In another embodiment, for example as described above with respect to airport security, above, both column assembly 106 and detector 200 center 212 remain stationary while a subject or object to be imaged moves through a rotating X-ray beam.

FIG. 15C illustrates rotation of angle δ 1540 of column assembly 106. This motion may also enable acquisition of a multiplicity of projections at various view angles; a similar effect may be enabled by translating X-ray tube 110 along z axis 116, as might be possible through rolling of the entire column 106 in this direction.

Operation

In one embodied mode of operation, the detector performs an initial "scout" scan of either the entire table or of a sub-area as prescribed by the user. Based on this initial scout image, the user or the system computer prescribes an area to be imaged. A number of imaging modes are possible, including linear raster scan of the area (possibly including a multiplicity of raster scan lines), or a combination of translation of the detector tray rotation axis O' together with continuous rotation of the detector around rotation axis y'.

In a second embodied mode of operation, the system is set to track the progress of an interventional tool, such as the tip of a catheter or other interventional device. The system automatically selects the detector tray center O' position so that the projection of the device tip is superimposed with the detector center O'. These automatic motions may be achieved either with or without simultaneous X-ray column translation along the subject table and associated X-ray tube pivoting with respect to axis x', depending on the imaging mode selected. Once the device tip has reached the theatre of operation (such as the coronary arteries in a cardiology procedure), the detector continues rotation around O', while minor adjustments to the O' location are dynamically made to maintain the device tip at image or detector tray center. The point O' may also be held at a given position, while fluoroscopic image refresh occurs through the continuous acquisition of data by the rotating detector. Alternatively, the detector trajectory may not include rotation, but be limited to a sequence of scans along specific raster lines, with the detector main axis either orthogonal or at a non-90-degrees angle with respect to the scan direction.

In another embodied mode of operation, adjustment of various system parameters, including relative position of the X-ray tube apparatus with respect to the object and detector, allow dynamically acquisition of several images of the same object for various projection angles and projection geometries. The projections may be chosen dynamically by the user, or the system may automatically loop through a predetermined sequence of projections.

Dynamic operation of the system may also enable acquisition of image data at different levels of image noise, spatial resolution or spectral composition. In particular, the system may first be operated at a first level of resolution, noise, spectral composition or other imaging parameter, and then be switched to a higher resolution or reduced noise mode or different spectral composition, for example upon user or automatic detection of an abnormality or threat. Imaging acquisition may also take place at various levels of resolution, either dynamically in time or spatially; such various resolution and noise levels being for instance achieved through variable binning of the native resolution detector pixels. The various detector lines or arrays may have variable native pixel resolution as a function of the line or as a function of distance from detector iso-center.

The present instrumentalities may be applied to the operation of flat-panels area detectors, either specifically designed or operated as follows: A beam of specific shape and spectral characteristics is swept across the active surface of the detector. In one embodiment, a fan-beam is scanned linearly and/or rotated using a collimator assembly and methods according to the principles described herein. In another embodiment, a beam of more complex shape (such as may be formed by a collimator plate as described above) and/or containing several fans and a central area, is scanned linearly and/or rotated. The flat-panel data are read out to allow image formation and image refresh at rates depending on the spatial location of a given image pixel.

The present instrumentalities further apply to the operation of computed tomography (CT) systems, either specifically designed or operated as follows: A beam of specific shape and spectral characteristics is swept across the active surface of the detector, as described in the paragraph above. The beam sweeping may occur independently or simultaneously with gantry rotation.

In embodiments where the detected X-ray beam is under-collimated with respect to the active detector, detector cells that are not exposed by the primary beam or by the beam penumbra detect scattered radiation. These measurements may be leveraged to perform scatter correction and or further object analysis and characterization.

Full-frame sampling of the active detector allows closed-loop dynamic adjustments to the X-ray beam parameters, including peak kilo-voltage, tube current, tube target location and selection, and filtration, to adapt X-ray imaging parameters to the composition of the object or anatomy being imaged.

In a tomosynthesis or limited-angle tomographic imaging mode, the X-ray source is set in motion along at least one of axes z 116 (column rolling), x' 1520 (tube translation along tube main axis), rotation of angle φ 1510 with respect to y' 122, or rotation of angle δ, 1540, or any motion that similarly contributes to the acquisition of a multiplicity of views (or projections) of the object to be imaged. Given the dynamics of the X-ray tube and the dynamics of the detector, the tracking algorithm orients tube angle (rotation with respect to the axis x') and/or collimator position and orientation, such that an X-ray beam of the appropriate shape projects onto the active part of the detector. This sequence of data acquisition results in the obtaining of a multiplicity of projection data that are then input to the 3D image reconstruction algorithm. A 3D image sequence can then be refreshed with the newly reconstructed information. Thus the system is designed for a fourth-dimensional data acquisition (time varying 3D data sets).

Embodiments with Enlarged Beam Center Portion

Figure 16A:
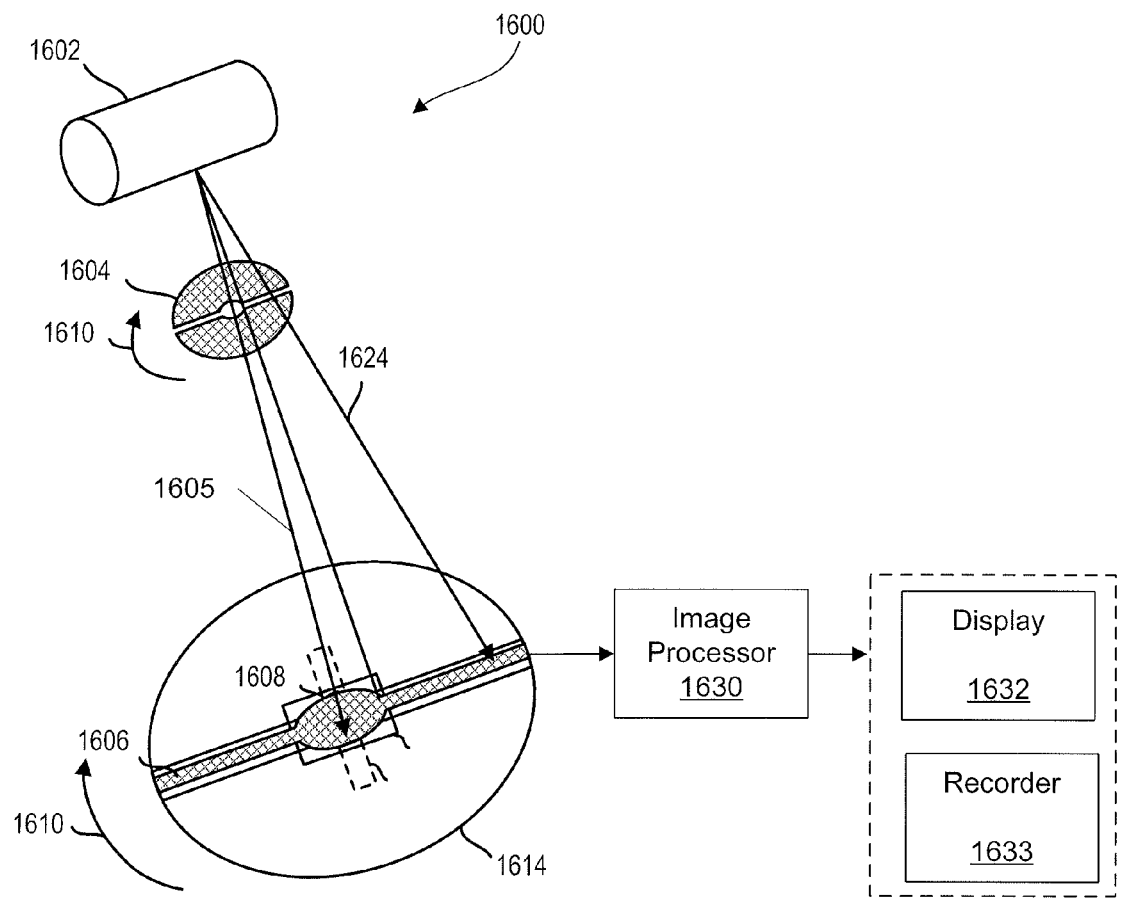
FIG. 16A is a perspective view of image chain components in a system for dynamic low dose X-ray imaging and tomosynthesis, in accordance with one embodiment.

In an embodiment, illustrated in FIG. 16A, a factor of from four to twelve reduction in patient radiation dose is achieved relative to prior fluoroscopy systems by taking advantage of the following:

(1) High resolution and high image refresh rates are necessary only over a small field of view in the immediate neighborhood of the catheter distal end;

(2) A larger imaging field of view is required for landmark navigation and viewing catheter movement in major vessels, but lower temporal and spatial resolution are acceptable outside a small field of view around the catheter tip;

(3) Imaging with a narrow X-ray fan-beam allows dispensing at least in part with the use of a scatter-rejecting Bucky grid.

As illustrated in FIG. 16A, a system 1600 for dynamic, low-dose X-ray imaging and tomosynthesis features an imaging chain having an X-ray source 1602, such as an X-ray tube 1602, a rotating collimator 1604 shaped to match the shape of an elongated slot detector 1606 mounted on a rotating tray 1614; the detector 1606 also has a center region-of-interest (ROI) area 1608. The collimator and detector rotation, indicated by arrows 1610, are synchronized such that any fan beam 1624 of X-rays emitted by X-ray tube 1602 and shaped by rotating collimator 1604 lands on detector 1606. The collimator rotates about an axis 1605 extending from the X-ray tube 1602 to the detector 1606. Image data acquired via detector 1606 (e.g., as described below, under the subheading "Image Generation") may be interpolated onto a fixed Cartesian grid by a processor 1630, stored in memory, displayed on a display device 1632 and/or recorded by a digital recording device 1633.

Figure 16B:
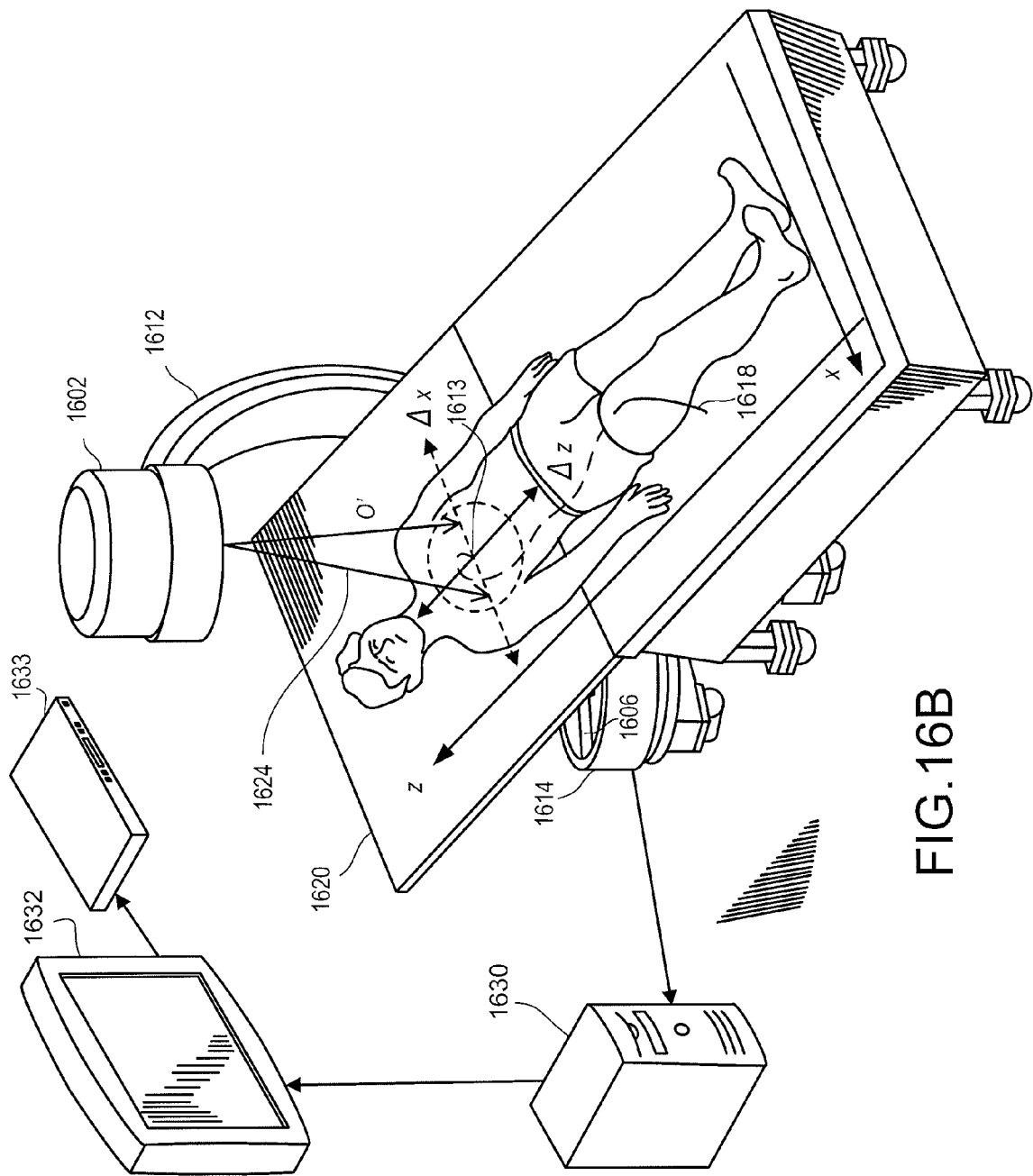
FIG. 16B is a perspective view of a system for dynamic low dose X-ray imaging and tomosynthesis as applied to an image guided intervention, in accordance with one embodiment.
Figure 17:
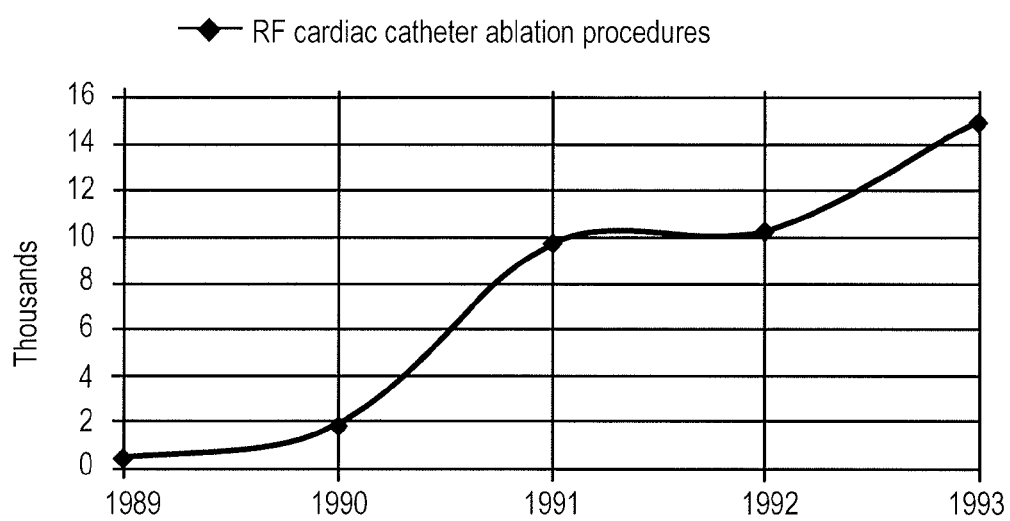
FIG. 17 is a graph showing number of RF cardiac catheter ablation procedures from 1989 to 1993 as estimated from a survey of 157 electrophysiology laboratories.

FIG. 16B shows the imaging chain described above integrated within an IGI system. The imaging chain is mounted on a C-arm assembly 1612 on a moveable base (e.g., base 2302, FIG. 23), enabling tracking of a catheter tip 1613 and acquisition of multiple projections through a patient 1618 on a radiolucent table 1620.

Figure 18A:
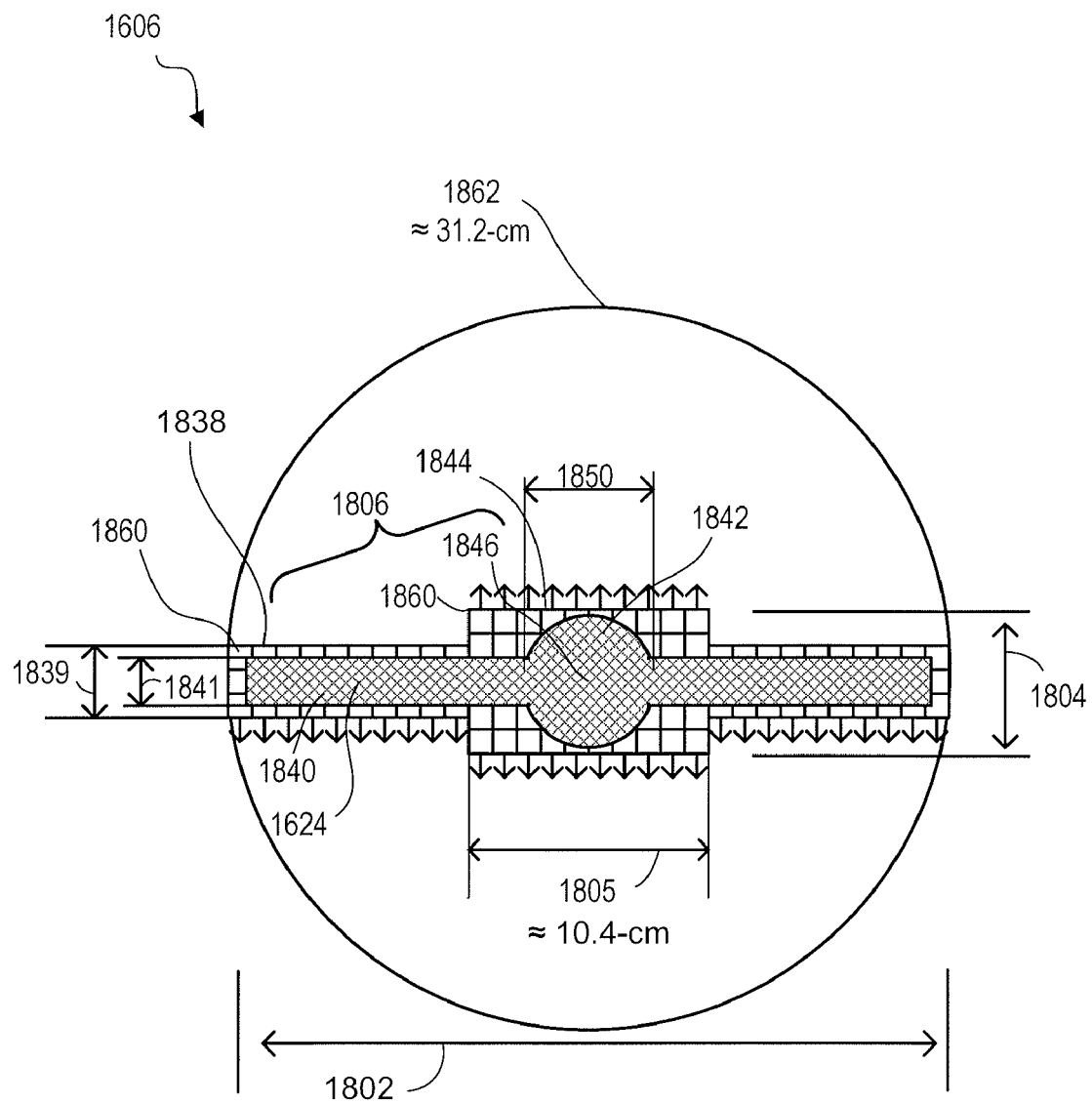
FIG. 18A is a simplified top view of a shaped detector, according to an embodiment.

As illustrated in FIG. 18A, detector 1606 includes a digital array detector 1806 with a side-to-side span 1802 of about 31 cm. The detector array 1806 has a center portion 1844 having width 1804 of about 6 cm and span 1805 of about 10 cm. The detector 1606 is rotatably mounted on a rotating tray 1614 or bearing plate mounted at the end of the rotatable C-arm assembly opposite X-ray tube 1602 such that it rotates about axis 1846.

In a preferred embodiment, a width 1841 of the wing portions 1840 of the fan beam 1624 at the detector is less than half the width 1804 of the center portion 1842 of the fan beam 1624 at the detector. The detector similarly has a center portion 1844 with width greater than a width 1839 of the wing portions 1838 of the detector. In an embodiment, the center portion 1842 of fan beam 1624 projection is roughly discoidal. A diameter 1850 of the center portion 1842 of fan beam 1624 at the detector is for example between 1 cm and 20 cm, and wing portions 1840 have for example width 1841 between 0.1 mm to 20 mm.

Figure 24A:
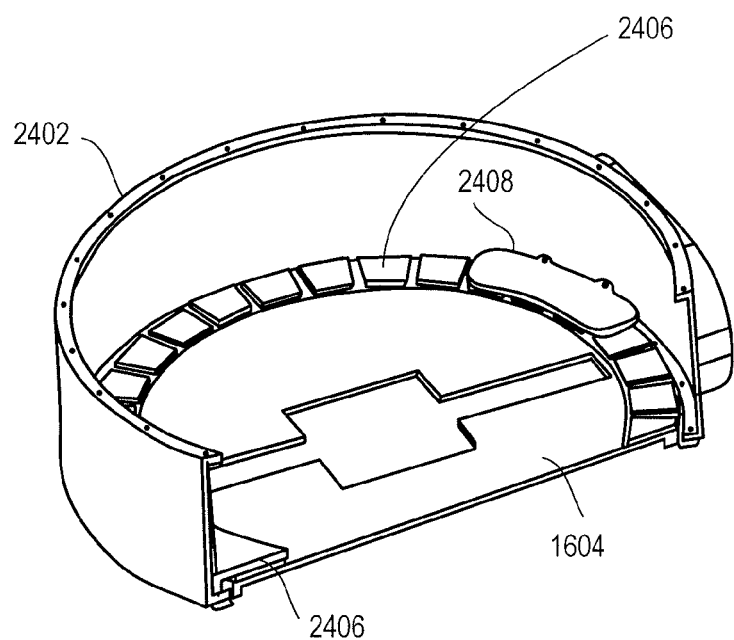
FIG. 24A is a top perspective view showing details of the rotating collimator of FIG. 23.

With reference to FIG. 24A, collimator 1604, of selectable aperture, is mounted on a rotatable assembly in a housing 2402 proximate to X-ray tube 1602 (see, e.g., FIGS. 16A-16B) to form a rotating fan beam 1624 that is projected through a patient, e.g., patient 1618. Apparatus, which may incorporate an electric motor and gearing, or permanent magnets 2406 attached to collimator 1604 and coils 2408 attached to housing 2402, is provided to rotate the collimator 1604. Bearings 2412 are provided so that the collimator 1604 rotates smoothly in housing 2402.

Rotation of digital array detector 1606 is synchronized with collimator 1604 rotation, such that the dexel array of the detector remains aligned with rotating fan beam 1624. The rotation rate of collimator 1604 and detector 1606 (not C-arm 1612) is adjustable from one half up to five rotations per second.

In alternative embodiments having more than two wings in the fan beam, the rotation rate is preferably at least $$\frac{1}{\text{(Wings)}}$$

revolutions per second, where Wings is the number of wings in the fan beam. In operation with a continuous X-ray source, as the fan beam rotates, the central portion of the beam continuously radiates any part of the subject exposed to it. Similarly, the wing portions of the fan beam intermittently irradiate non-moving portions of the subject that they intersect at a rate equal to the rotation rate times the number of wings.

X-ray tube 1602 and detector 1614 are mounted on a mount typical of C-arm systems; the Source-to-Image-Detector (SID) distance adjustable in the range 90 to 130 mm.

It is expected that the system 1600 of FIG. 16A will provide at least a factor of four in dose savings for equivalent center image signal-to-noise ratio (SNR) versus conventional fluoroscopic systems. The dose savings is obtained primarily from the system geometry and the absence of a Potter-Bucky grid on the detector wings.

Figure 19:
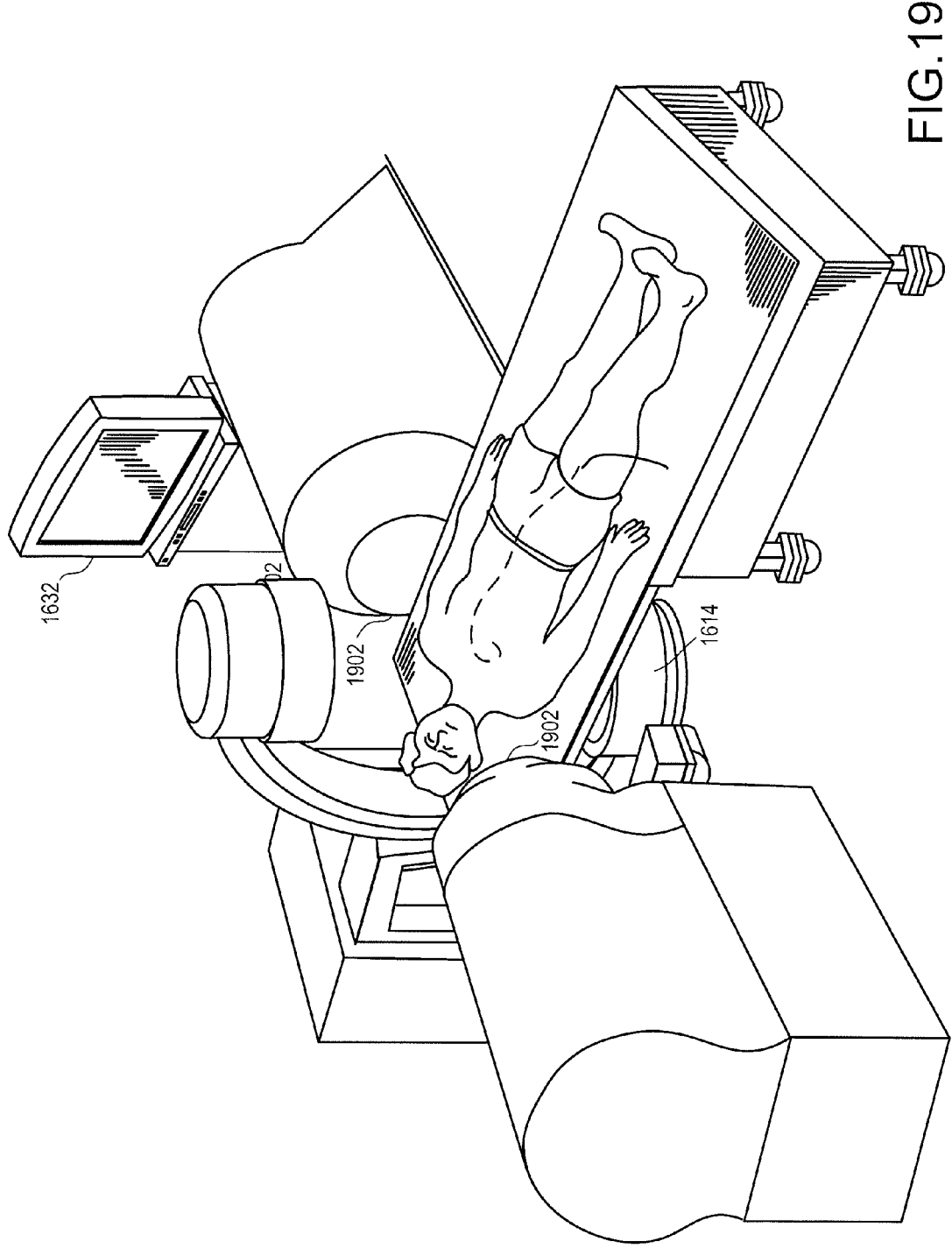
FIG. 19 is a perspective view showing a system for dynamic low dose X-ray imaging and tomosynthesis used with a magnetic navigation system for the performance of minimally invasive electrophysiology interventions, according to an embodiment.
Figure 23:
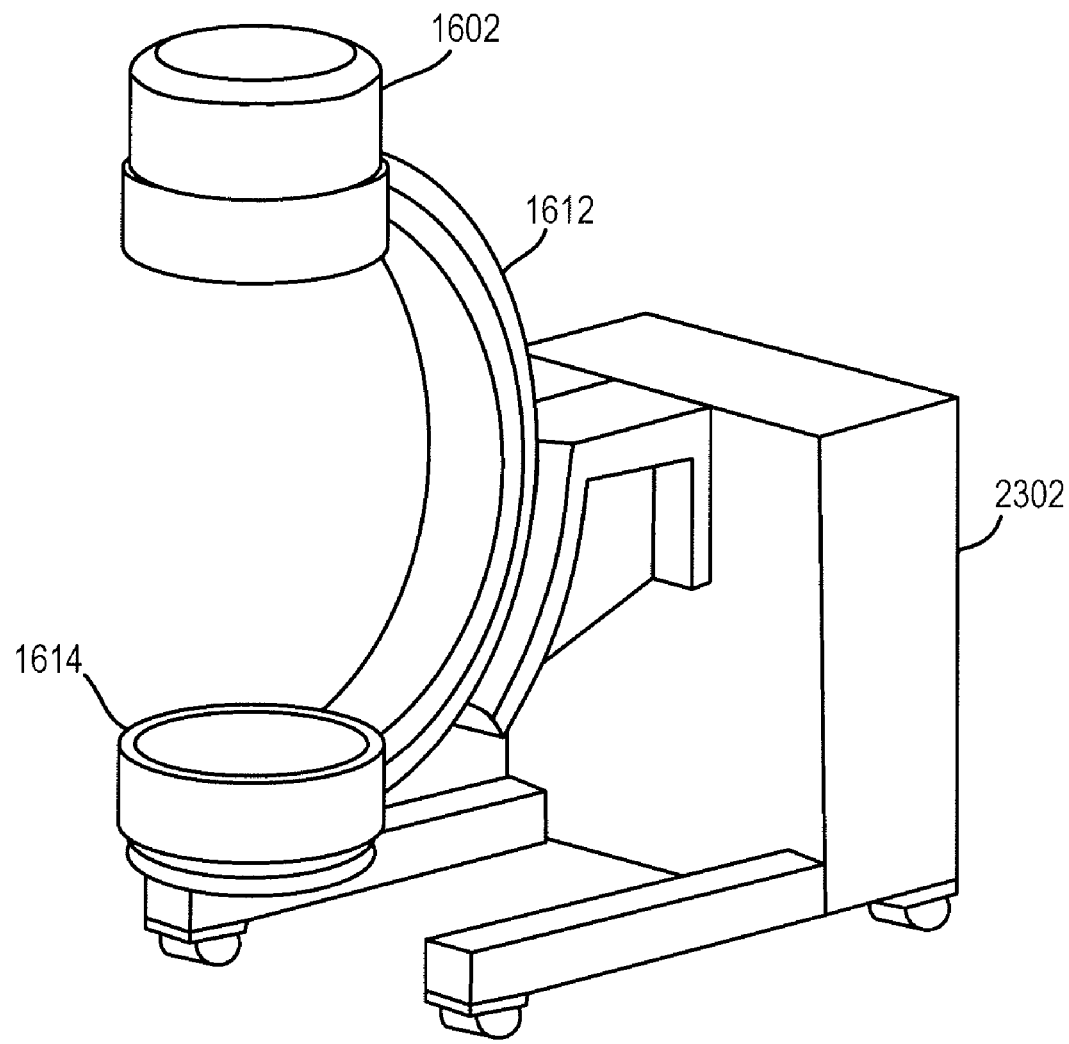
FIG. 23 is a schematic perspective view of a system for dynamic low dose X-ray imaging and tomosynthesis, with an X-ray source, rotating collimator and rotating detector mounted as part of a C-arm assembly, according to an embodiment.

In an embodiment, the system 1600 illustrated in FIGS. 16B, 23, and 18A is used for dynamic fluoroscopy integrated with a Stereotaxis IGI Niobe system, as illustrated in FIG. 19, to perform cardiac catheterization. This embodiment of the system adds an electromagnet having a pole pieces 1902 for manipulation of a magnetic catheter tip (e.g., tip 1613) to the system illustrated in FIGS. 16B, 23, and 18A

As illustrated in FIG. 16A, rotating collimator 1604 is matched (pre-patient) to a rotating digital detector array 1606, to under-collimate X-ray beam 1624 onto detector 1606. Detector 1606 has an elongated shape with a larger central area 1608. A variety of collimator 1604 shapes provide effective imaging trade offs between dose and temporal resolution for different applications.

Detector 1606 is assembled by tiling detector modules with read-out 1807 at up to 1,000 frames per second ("fps"). The detector modules of detector 1606 support 1,000 fps in native dexel size of 120 microns square, or may bin dexels 2×2 and sample at 500 fps or 1,000 fps. The detector 1606 is assembled from four modules tileable on three sides, each module having readout on one long side, each module about 10 by 3 centimeters in size. Other module configurations are possible. About 16% of the approximately 31.2 cm disk area is occupied by active detector in FIG. 18A.

Figure 18B:
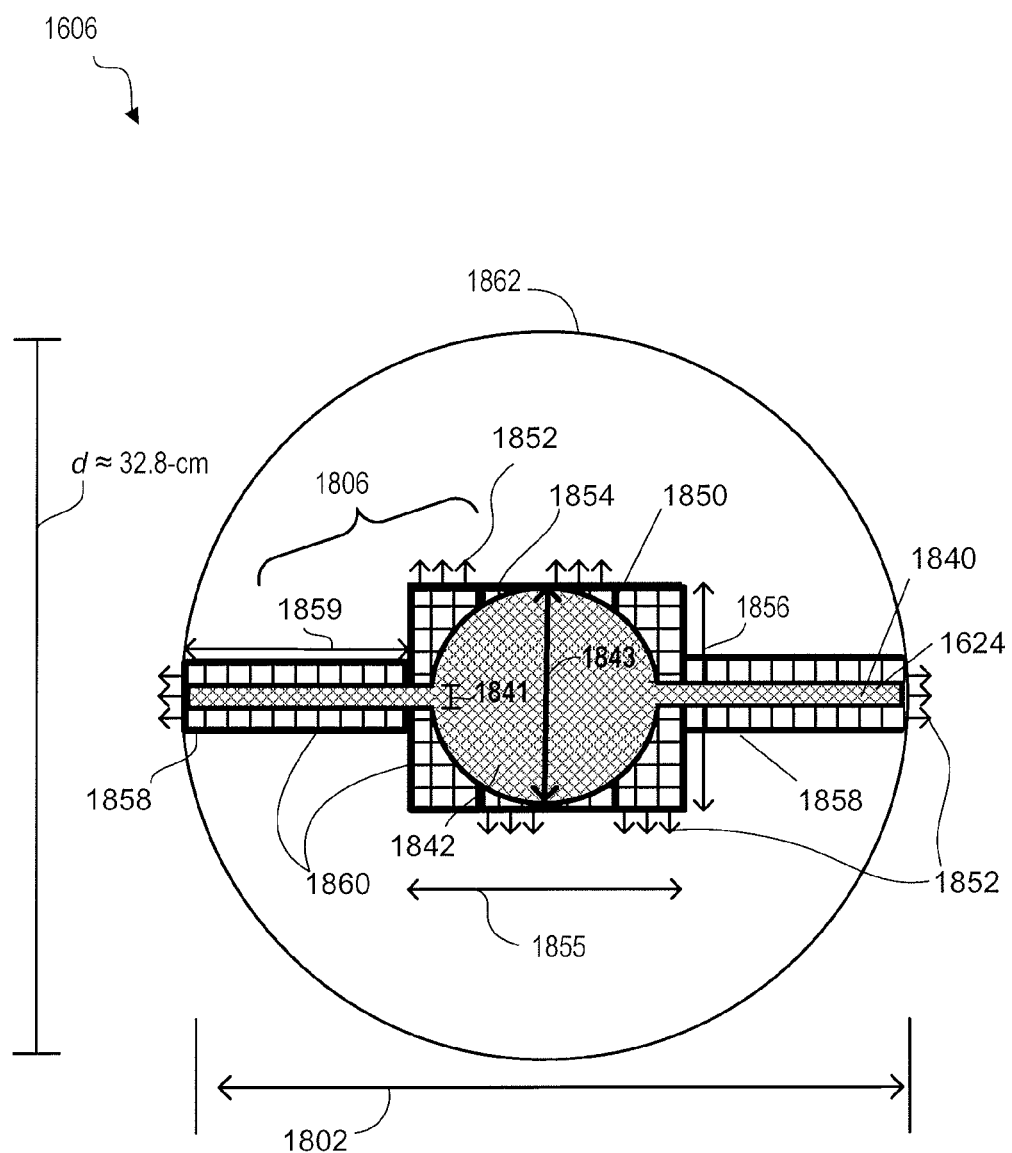
FIG. 18B is a simplified top view of an alternately shaped detector, having a larger central zone, according to an embodiment.

The design of FIG. 18B may provide increased operation flexibility by supporting a larger center area 1842 of the fan beam 1624, with diameter 1843 up to 10 cm. Detector 1806 with a side-to-side span 1802 of about 31 cm is assembled from multiple modules 1860. Detector modules 1860 having readout 1852 on their narrow sides are used. Four modules 1860 are abutted along their long sides to define a center area 1854 having a length 1855 of about 12.0 cm by a width of 1856 of about 10.4 cm. Two additional modules are arranged as detector "wings" 1858. Wings 1848 for example have a length 1859 of about 10.4 cm. Width 1841 of wing portion 1840 of fan beam 1642 is for example about 1 cm. Accordingly, about 22% of the area of 32.8 cm diameter (d) disk 1862 area is occupied by the active detector. A detector of this larger size may also be used with a collimator having the smaller center area of the embodiment of FIG. 18A.

Such geometries naturally define a center area 1842 of fan beam 1624, continuously exposed to X-ray, and an outside area is intermittently exposed to the X-ray beam at a rate related to rotation rate, wing count, and wing geometry.

Image Generation

Image data acquired on a rotating sampling grid as defined by the dexel array of each detector module and the rotation angle of the detector at the moment of data capture; this data is essentially described in polar coordinates. This data is interpolated onto a fixed Cartesian grid by processor 1630 (FIGS. 16A, 16B), in a manner akin to "gridding" familiar to astronomers and CT image reconstruction developers. In an alternative embodiment acquired data is first defined from the various detector rows to generate a few radial samples, such radial samples then being interpolated onto the Cartesian image grid using gridding or a faster method. Once remapped, the image, or image sequence, is stored in memory, displayed on a display device 1632, and recorded for future diagnostic use by a digital recording device 1633.

As the captured image is remapped from polar to Cartesian coordinates, some portions of the Cartesian gridded image stored in memory do not correspond to illuminated portions of the detector 1606 during a given readout of the detectors. These portions of the reconstructed image, including those portions that correspond to areas of the disk 1862 not covered by detectors 1606, 1806, are left unaltered in memory during that readout, but are updated during other readouts at other points during collimator rotation when they do correspond to illuminated portions of the detector. In this way, as the two wing portions 1840 of fan beam 1624 rotate, the image in memory is updated twice per revolution of beam 1624, collimator 1604 and detector 1606

RTR CMOS-HgI2 Detector Technology and Detector Specifications

Real-Time Radiography LTD (RTR), an Israeli company, has developed a CMOS-$HgI_2$ detector technology appropriate for fluoroscopy suitable for the needs of this system 1600. This technology uses state-of-the art CMOS integrated circuit sensor chips, each 2.984 cm×10.368 cm, with a dexel pitch of 120 μm (232×864 dexels). The chips or modules are three-side abuttable and in the current configuration provide for full matrix sampling with read-out on the narrow side. A version of these will provide a 1,000 fps read out rate (200.44 M samples per s). Other sizes and dimensions of sensors may also be used. With the read-out electronics required to achieve this fast sampling rate, read-out noise of less than 1,000 electrons per sample is expected.

The detector 1606, 1806 has four or six tiled chips, covering a total area of 123.8 or 185.6 $cm^2$. A photoconductor layer within the modules of 300 to 500-microns. $H_gI_2$ optimizes DQE for the pixel size considered. RTR uses a radiation-resistant CMOS technology that ensures radiation hardness well beyond the expected doses (as measured behind the photoconductor layer) and into the 200 Gray range. The radiation resistance ensues from a combination of 0.35 μm process and guard ring design. The design provides for CMOS radiation tolerance both from exposure-to-exposure as well as over the device lifetime (13 years). The chip provides synchronous operation through integrated, on-chip sample and hold operation.

A version of this detector circuit has been realized in a 0.35 μm CMOS process. Test chips have been characterized and found to be within 20% of the predicted noise performance. Design target is to achieve an SNR of 1 at 0.1 μR exposure, which is almost one order of magnitude better than available CsI/TFT flat panel technology.

Scatter

Slot-scanning, as used in this system 1600, is a practical and efficient method of controlling X-ray scatter. Imaging has been done with a 10 mm beam width without need for a Bucky grid, as known in the art.

Image Guided Interventions—Stereotaxis' Magnetic Navigation System

The Stereotaxis Magnetic Navigation System, see FIG. 19, is designed to allow physicians to more effectively navigate catheters, guide wires and other magnetic interventional devices through the blood vessels and chambers of the heart to treatment sites. This is achieved using computer-controlled magnetic fields that govern motion of the internal working tip of the catheter, guide wire or other interventional devices. Two opposing poles of a large magnet 1902 are orientable to create in the patient a magnetic field of about 0.1 Tesla of any desired orientation. Catheters used with this system have a small tip magnet that is oriented by the magnetic field in any desired direction during catheterization, according to navigation needs. In FIG. 19, the Stereotaxis Magnetic Navigation System is integrated with an X-ray fluoroscopy system (e.g., system 1600) as heretofore described with reference to FIGS. 16A, 16B, 18A and 23, and a 3D RF-based localization system (such as BioSense Webster) is provided for tracking catheter position within the patient.

Dose Efficiency

Figure 21:
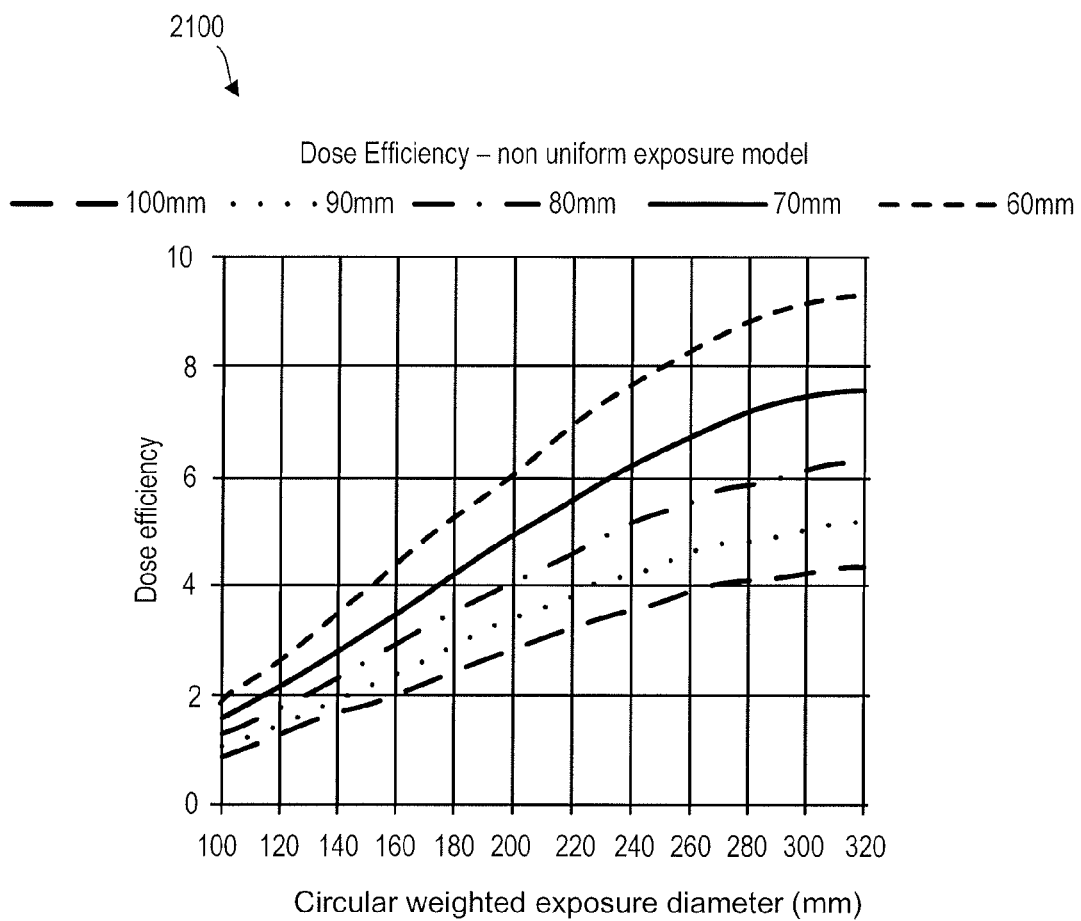
FIG. 21 is a graph showing dose efficiency gains achievable with the system of FIGS. 16A and 16B as compared to a fluoroscopy imaging system that uses a non-uniform X-ray exposure across a circularly-shaped exposure area.
Figure 22:
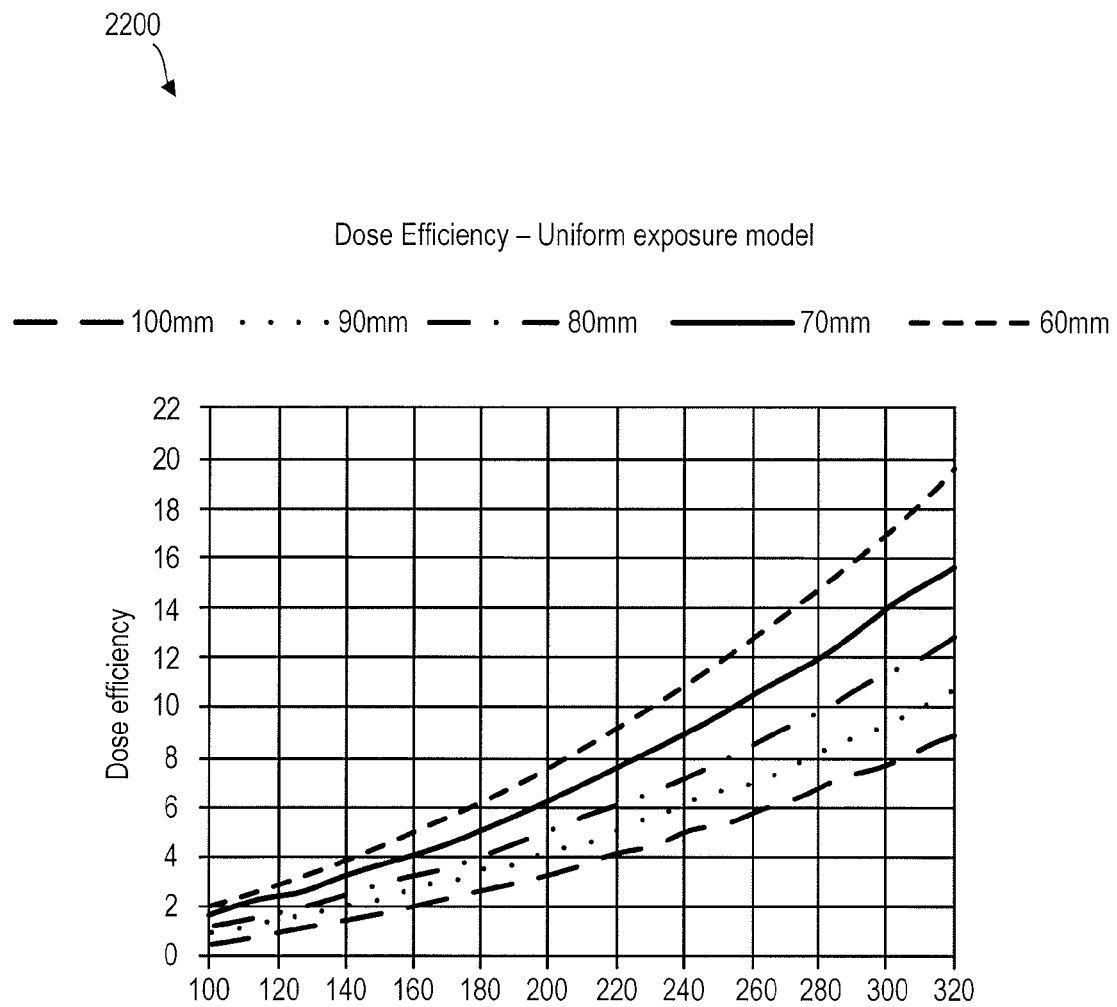
FIG. 22 is a graph illustrating dose efficiency gains of the system of FIGS. 16A and 16B as compared to a fluoroscopy imaging system that uses a uniform X-ray exposure across a circularly-shaped exposure area.

FIG. 21 and FIG. 22 are graphs 2100, 2200 showing results of a dose-efficiency computer model study comparing a model of system 1600 having fixed 32 cm exposure coverage and with differing diameters of the center portion of the beam to models of conventional mode (CVM) C-arm machines of uniform exposure and center-weighted exposure types. For purposes of this computer model, system 1600 is an embodiment having a fan beam 1624 center portion disk area 1842 with diameter varying between 60 mm and 100 mm. System 1600 is further assumed to have a Bucky grid over the center disk portion 1842 of the detector, and two elongated detector wings for receiving wings of the fan beam that lack a Bucky grid.

Figure 20:
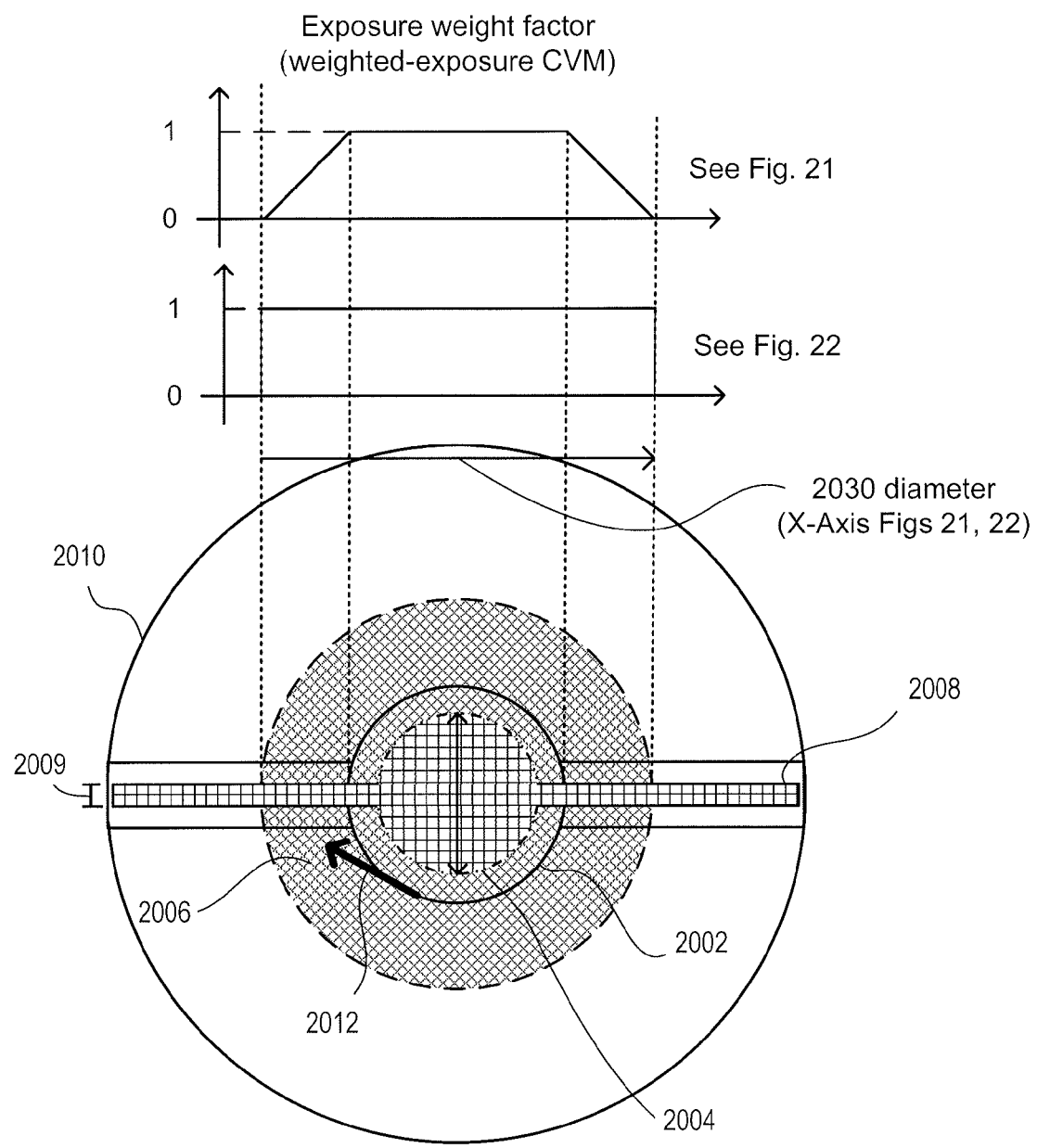
FIG. 20 is a simplified top view of a shaped detector, illustrating parameters for comparative dose studies.

The CVM model, for comparison has a circular area exposure with diameter 2030 (FIG. 20) varied from 100 mm to 320 mm as indicated by the X axis of relative dose-efficiency graphs 2100, 2200. The areas of exposure for this calculation are illustrated in FIG. 20. An upper diameter limit for diameter 2030 matches the 32 centimeters diameter of the LDM and a lower limit 2002 of diameter 2030 is assumed to be 100 mm for the CVM. In the computer models there is an assumed exposed center area 2004 in low-dose mode and a larger central exposed area 2006 in conventional mode. In the computer model, LDM fan beam wings 2008 are assumed to be 1 cm wide 2009 with no Bucky grid; and overall detector area 2010 in low dose mode is 32.5 cm in diameter.

In calculating the dose curves of graph 2200, the CVM detector area is uniformly exposed, as with many C-arm machines on the market. In graph 2100, FIG. 21, a weighted-exposure CVM machine is modeled wherein the peripheral area is assumed to be covered by an attenuation filter varying from no attenuation over a central 10 cm disk to infinite attenuation at the outer diameter 2030, as indicated on the X-axis, this model follows the region-of-interest approach of Rudin et al, (Rudin S and Bednarek DR. "Spatial shaping of the beam: collimation, grids, equalization filters, and region-of-interest fluoroscopy." In: Balter S, Shope T B, Eds. Syllabus: a categorical course in physics—physical and technical aspects of angiography and interventional radiology. Oak Brook, Ill.: Radiology Society of North America, 75-85, 1995). The results shown in graphs 2100 and 2200 support a potential dose savings factor of four to twelve using system 1600 as compared to these other machines.

Dexel Size and Data Acquisition Rates

A spreadsheet model was adapted to represent system 1600 geometry. The SID retained for the investigation was 100 cm. The American Association of Physicists in Medicine (AAPM) chest phantom was modeled and X-ray technique chosen to be 120 kVp (low dose kVp), 2 mA, and 2 mm Al filtration. The mean number of photons collected at the detector, number of module dexels (for a fixed area), data rate, and velocity of a point at the center disk edge, see 2012 in FIG. 20 were calculated as a function of dexel size and are listed in the table below:

TABLE 1

| Tube: | kVp range | mA range | Exposure | kVp switch | | |
|---|---|---|---|---|---|---|
| | 50-140 | 0-100 | | <2 ms | | |
| Detector: | Material | Read out | Noise | QE | Pixel size | Matrix |
| | 400 μm HgI$_2$ | >=1 ms | <1000 e at 1000 fps | >60% at 120 kVp | 120 μm native | c.f. FIG. 2 |
| System: | Beam width | Beam length | Scan speed | Scan time | | |
| Filter: | Wing ≦10 mm Low kVp: Al | 312 or 328 mm High kVp: Al + Cu | 1-5 rotation/s | >1 hour | Algorithm $0^{th}$ or $1^{st}$ order interpolation Offset and gain corrections | |

Table 1 data represents a 1 ms sample interval at 1 rotation per second. Digital summation, dependent on the desired image display frame rate, may contribute to improving the image signal-to-noise ratio (SNR). As an example, and with a 50 fps image display rate, a factor of 20 summation will improve the SNR by about a factor 4.5. In $H_gI_2$ (Mercury iodide) the signal generated per X-ray event is in the range of 1,000 to 2,000 electrons, depending on energy; with a conservative upper bound on the electronic noise of 1,000 e, the system will be X-ray noise limited. An alternative mode of operation is to sample the center modules at 500 fps, with a 2×2 wing dexel binning. In that case, at 240 μm (center size), the data rates decreases to 226 Mbytes/second and the edge velocity is 2.6 dexels/sample. It is noted that this type of motion blurring also occurs in CT. For a source to iso-center distance of 500 mm, and an iso-center to detector distance of 500 mm, 2 rotations per seconds and 1000 projections per rotation, the source and detector travel π mm per sampling interval while on the detector the channel-to-channel distance is typically less than 1 mm (π channels/sample). Displacement blurring varies with the distance from the rotation axis and no blurring occurs at the center; the rotation rate is chosen as a trade-off between spatial blurring and temporal resolution, one rotation per second supporting a refresh rate of 2 frames per second in the outside area. Faster outer image frame refresh rates can also be obtained by adding two or more "winglets," as shown in FIG. 16A. Although even at 120-μm the system is expected to be noise limited, use of pulsing at higher techniques could increase the number of photons per signal sample while maintaining the overall dose delivered.

TABLE 2

| Dexel Size (μm) | Mean photons per dexel | Dexels per module | Data Rate (Mbytes/s) | Velocity at center edge (dexels/sample) |
|---|---|---|---|---|
| 60 | 2.4 | 859,392 | 7,216 | 5.2 |
| 80 | 4.3 | 483,408 | 4,059 | 3.9 |
| 100 | 6.7 | 309,382 | 2,598 | 3.1 |
| 120 | 9.6 | 214,848 | 1,804 | 2.6 |
| 140 | 13.1 | 157,848 | 1,325 | 2.2 |
| 160 | 17.1 | 120,852 | 1,015 | 2.0 |
| 180 | 21.6 | 95,488 | 802 | 1.7 |
| 200 | 26.7 | 77,346 | 649 | 1.6 |
| 220 | 32.3 | 63,922 | 537 | 1.4 |
| 240 | 38.4 | 53,712 | 451 | 1.3 |

Table 2 shows signal modeling, data rates, and velocity as a function of dexel size above numbers are for 1,000 fps sampling throughout the detector; 2×2 wing dexel binning and 1 rotation per second. The native dexel size of the Phase I detectors is 120 microns square. Two modes are available on the sensors used in a particular embodiment: imaging at 120-microns square and imaging at 240-microns square.

A spatial resolution of 240-microns compares with the nominal spatial resolution of a 15 cm diameter image intensifier coupled to a 1,024×1,024 CCD.

Figure 24B:
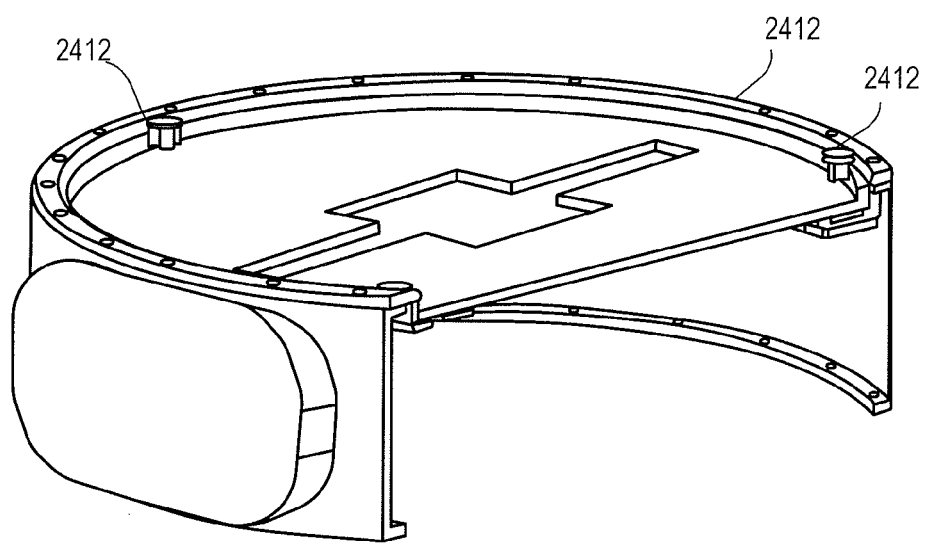
FIG. 24B is a bottom perspective view showing details of the rotating collimator of FIG. 23.

The collimator design is outlined in FIGS. 24A and 24B. An angular resolver or step counter allows tracking the collimator rotation to within $4 \times 10^{-5}$ radians: a precision encoder such as the Gerley Precision Instruments model 9220, providing 144,000 counts per revolution, is attached directly to the rotating assembly and enable sub-pixel rotational position accuracy ($\tan^{-1}(0.24/160) \approx 0.0013$).

The rotatable mount for the detector resembles that previously discussed with reference to FIG. 3. As is known from CT technology, a slip ring brings power to the rotating detector tray from the C-arm assembly and an optical slip ring permits data transfer. Optical slip-rings are commercially available with a capacity of 1.32 Gb/s to 5 Gb/s per optical channel and can accommodate several optical channels (Moog Components Group). In an embodiment, sampling all detector modules occurs at 1000 fps and binning the outer modules dexels 2×2 on-chip. With 4 modules each having an array of 232 (module rows) by 864 (module columns) of dexels ×2 (byte depth) at a rate of 1000 fps and 2 modules binned 2×2 and sampled at a maximum rate of 1000 fps the maximum data rate to transfer from the rotating detector tray to the imaging system is about 1.8 Gbytes per second, which is within the bandwidth of optical slip-ring data transfer devices. With the same wing modules parameters but a center area binned 2×2 and sampled at 500 fps the data rate is 269 Mbytes/s.

A rotation control element enables accurate tracking of the detector rotation to within 4×10−5 radians and ensures that the collimator and detector are synchronized so that the X-ray beam always projects onto the detector active area.

The detector 1606, 1806 is magnetically shielded, using mu-metal if necessary, to ensure detector electronics operation free of spurious signal perturbations in magnetic fields of the order of 0.2 Tesla. The X-Ray tube 1602 is also shielded Such an arrangement enables a power transfer to, and data transfer from, the rotating detector 1606, 1806 at rates up to 1250 Mbytes/s using two Moog slip-ring optical channels at 5 Gbit/s each).

Image Generation

At a fluoroscopic display frame rate, such as 50 fps, data corresponding to 10 to 20 detector frames acquisitions is accumulated in an image frame buffer and normalized prior to display. With 2×2 dexel binning the entire image frame will be less than 1328 pixels×1328 pixels. Data pre-preprocessing, including offset and gain correction, is performed on the image grid data. Current state-of-the-art DSP approaches (Texas Instrument C6000 series), or field-gate-programmable-arrays (FPGA) approaches (Xilinx Virtex-5), support interpolation of data from a radial, rotating, detector sampling grid to a non-rotating, Cartesian image grid at a rate of sufficient to support an image rate of up to 50 frames per second.

Measurements of scatter to primary ratio (SPR) at the center and periphery of the detector. SPR measurements of the proposed and conventional detector systems determine the contrast degradation factor (CDF) due to scatter acceptance as: $CDF = C_0(1+1/SPR)^{-1}$. Measurements with and without a grid for the conventional detector can determine the signal to noise ratio (SNR) improvement factor according to techniques described by Neitzel.

Entrance skin air kerma (ESAK) rate in mGy/minute is determined from free-in-air ionization chamber measurements between the X-ray source and attenuating object as a function of kVp, mA, tube filtration, and frame rate in the center (higher rate) and periphery (lower rate regions) over the FOV with a calibrated, small volume chamber and dosimeter system using inverse square law corrections to the object entrance plane. Acquisition geometry will be standardized for all measurements in terms of source to detector, source to object, and object to detector distance. Fixed exposure times provide an integral air kerma measurement in mGy for the purpose of comparison to variations in X-ray acquisition technique as well as comparison to conventional system air kerma measurements.

During fluoroscopic operation, the air kerma rate (a measure of radiation dose) of the peripheral area of the proposed detector is significantly lower and temporally distinct from the central area. This is verified with a calibrated Dose Area Product (DAP) chamber positioned at the exit of the collimator to fully capture the projected X-ray fluence from the rotating collimator. This provides a dose-area integral measurement in mGy cm². Effective dose, is estimated from the DAP values using empirically determined mean DAP to effective dose conversion factors ranging from 0.073 mSv $Gy^{-1}cm^{-2}$ to 0.315 mSv $Gy^{-1}cm^{-2}$.

Embodiments with Scintillation Crystal or Fluorescent Screen

In an alternative embodiment, a detector sub-system made of either an image intensifier associated with an optical camera via a coupling lens, as known in the art, or a fluorescent X-ray screen followed by a mirror associated to a lens and a fast-frame digital optical camera. A system geometry using a fluorescent screen is schematically illustrated in FIG. 25.

As with the embodiment of FIGS. 16A & 16B, an X-ray source 2502 is positioned to radiate through a rotating collimator 2504. The rotating collimator 2504 may include a central area, and a number of "wings" extending from the projected center of rotation substantially to the edge of the desired X-ray field-of-view (FOV), as illustrated in FIGS. 16A, 18A, 18B. The central area may be of circular, rectangular, or other shape as determined by collimator 2504. A resultant fan beam 2506 passes through an object of interest 2508 (such as a patient or inanimate object) before impacting a fluorescent screen 2510.

Light 2512 emitted when X-ray photons impact the fluorescent screen 2510 are reflected by a mirror 2514 through a lens 2516 into an electronic optical camera 2518. Such geometry allows locating the optical camera away from the X-ray primary field, and also allows shielding of the camera from stray radiation. The frame rate of 1,000 fps is typical of a fluoroscopy application according to the disclosed embodiments; higher frame rates in the range 1,000 to 5,000 fps may be desirable in specific implementations. Camera frames are windowed, accumulated and averaged, actual display frame rates are in the fifteen to sixty frames per second range.

Figure 25:
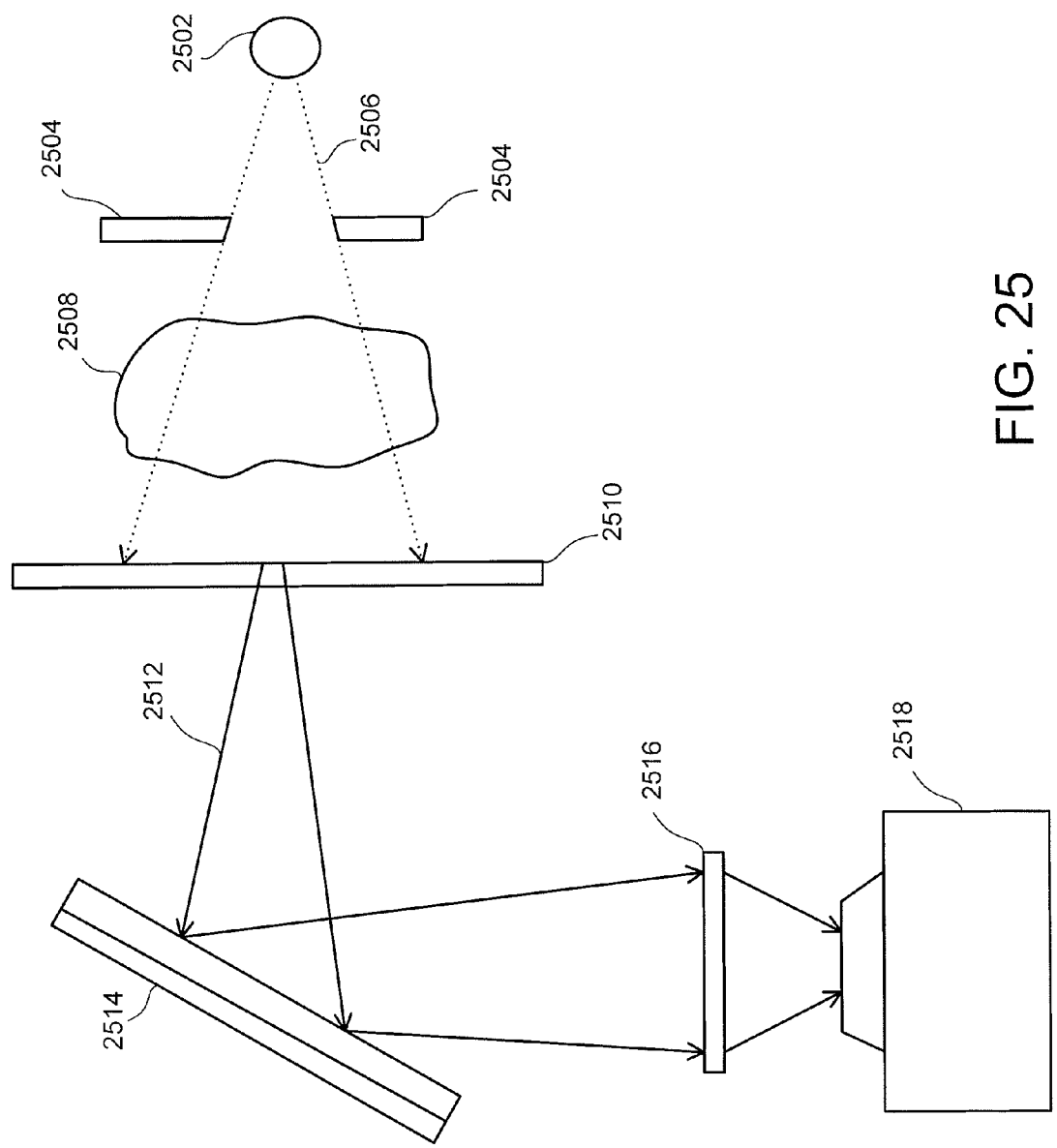
FIG. 25 is a schematic diagram of a system for dynamic low dose X-ray imaging and tomosynthesis using a large area fluorescent screen coupled to a high-frame digital optical detector through a mirror and optical lens combination, in accordance with an embodiment.

In FIG. 25, the entire assembly of fluorescent screen 2510, mirror 2514, lens 2516, and camera 2518 is rotated synchronously with rotating collimator 2504 and fan beam 2506. The resulting captured image is processed as heretofore discussed.

Dual Energy Acquisition

Figure 26:
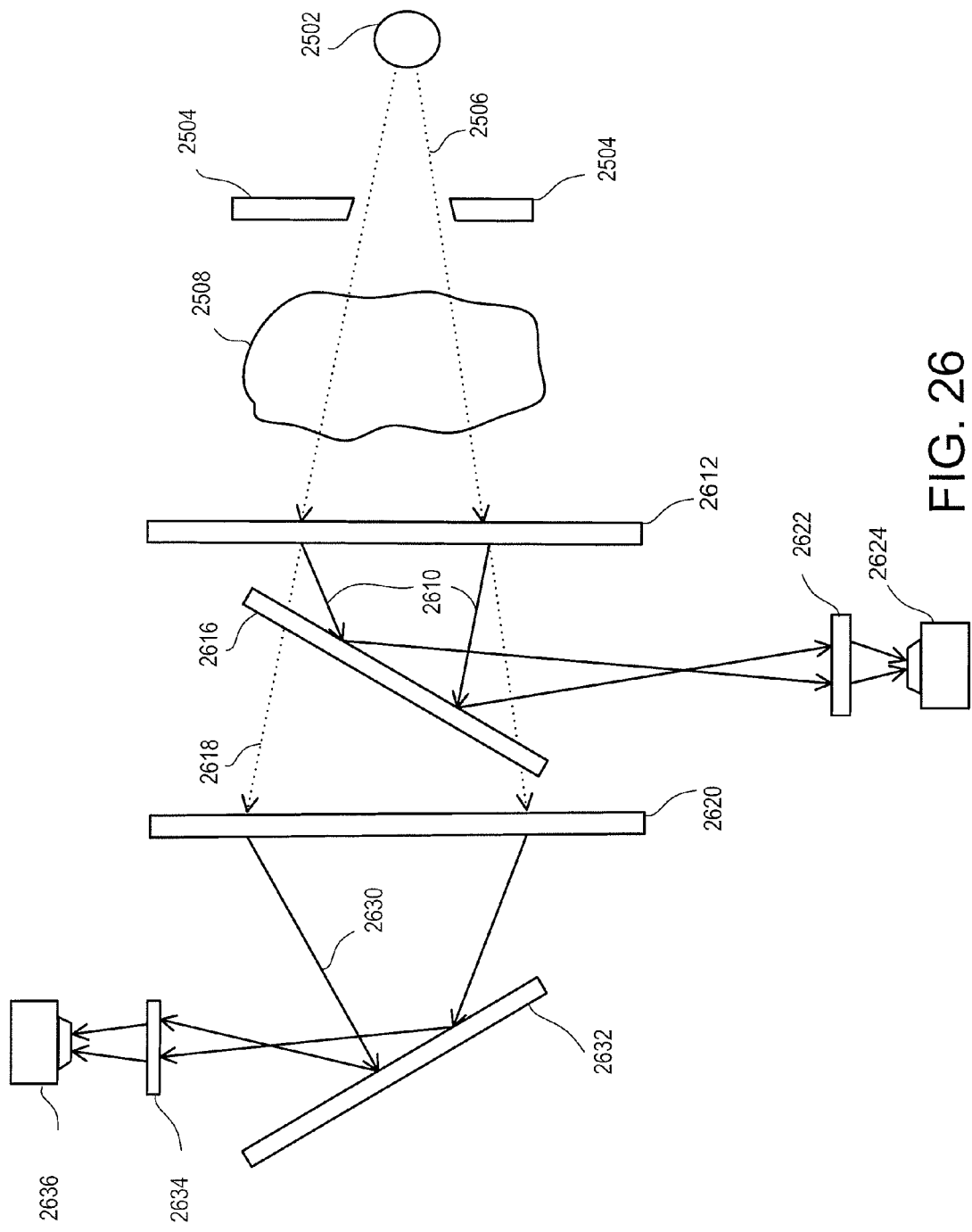
FIG. 26 is a schematic diagram of the system of FIG. 25, incorporating a second fluorescent screen coupled to a second digital optical detector, through a second mirror and lens combination.

A dual-energy implementation of the low-dose fluoroscope according to the principles of this invention is shown in FIG. 26. Here, a first X-ray fluorescent screen 2612 is made thinner than screen 2512 of FIG. 25, such that at least part 2618 of the impinging X-ray radiation penetrates the screen without interaction and continues past a first mirror 2616 (relatively X-ray transparent) onto a second X-ray fluorescent screen 2620. Such radiation represents "harder" X-rays than those absorbed by the first screen, in that low-energy X-ray photons are preferentially absorbed by the first screen 2612, and as a result the average beam energy impinging the second screen 2620 is higher. As known in the art, such a dual-screen approach may be optimized for dual-energy X-ray imaging, thereby increasing the ability to resolve tissue types.

Light 2610 from first screen 2612 is reflected by first mirror 2616 to a first lens 2622 and first camera 2624. Similarly, light 2630 from second screen 2620 is reflected by a second mirror 2632 to a second lens 2634 and camera 2636. Images from both cameras 2624, 2634 are translated into Cartesian coordinates by processor 1630 (FIGS. 16A, 16B) and the intensity of image from first camera 2624 is compared to that of second camera 2634. Differences in intensity between the first 2624 and second 2634 cameras are used to apply a "false color" to the image, permitting a radiologist or cardiologist to more easily differentiate tissue types.

Acquisition Techniques; Source Pulsing and Camera Gating

Figure 27:
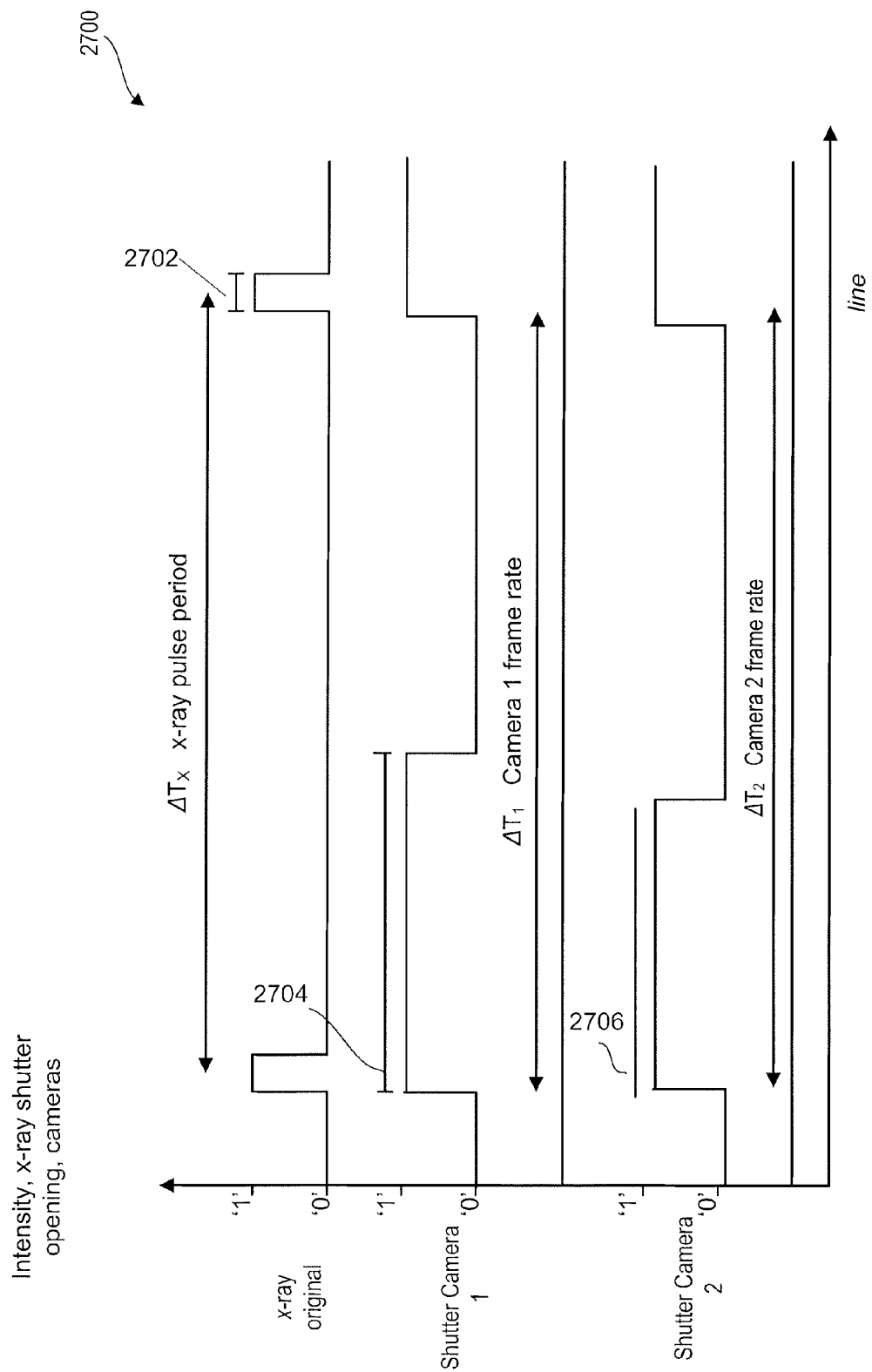
FIG. 27 is a timing diagram illustrating timing of X-ray and camera shutters to minimize motion artifact in image frames, according to the system of claim 26.

It is known that fluorescent screens have "lag" or afterglow properties: even though light emission in response to X-ray stimulation starts instantaneously, light emission from the screen continues briefly after the X-ray stimulation has stopped. Accordingly, in an embodiment, the X-ray tube is operated in "pulse mode;" the X-ray being "on" (state "1") for a fraction of the total frame time. For example, for a fluoroscopy application at 1,000 fps, it might be desirable to have a pulse of X-ray of 100 micro-seconds (100 μs) for each 1 ms frame. Such a mode is shown and described with respect to FIG. 27 in the context of a dual-energy implementation as illustrated in FIG. 26. Cameras 2518 (FIG. 25), 2624 and 2634 are provided with shutters (not shown) capable of operating at a high speed and high frame rate, as is common in imaging. The shutters for both digital cameras 2624, 2634 open at times 2704, 2706 in synchrony with the X-ray pulses, having on-time 2702, 2704, and close when most afterglow of their respective screens has ended. Once the shutter has closed, the camera image sensor circuits are read and the camera is prepared to receive a following frame. Further, the phosphors of the screens are chosen such that almost all afterglow has ended before the following pulse so that the resulting data captured in the respective frames correspond only to the "primary" light emission during the X-ray pulse; the remaining of the light emission, or "afterglow," is not recorded in following frames in as much as afterglow has become negligible by the time of the next X-ray pulse. As illustrated in diagram 2700 of FIG. 27, the X-ray pulse widths, shutter camera opening and closing times, are controllable in a preferred embodiment of the present invention.

Figure 28:
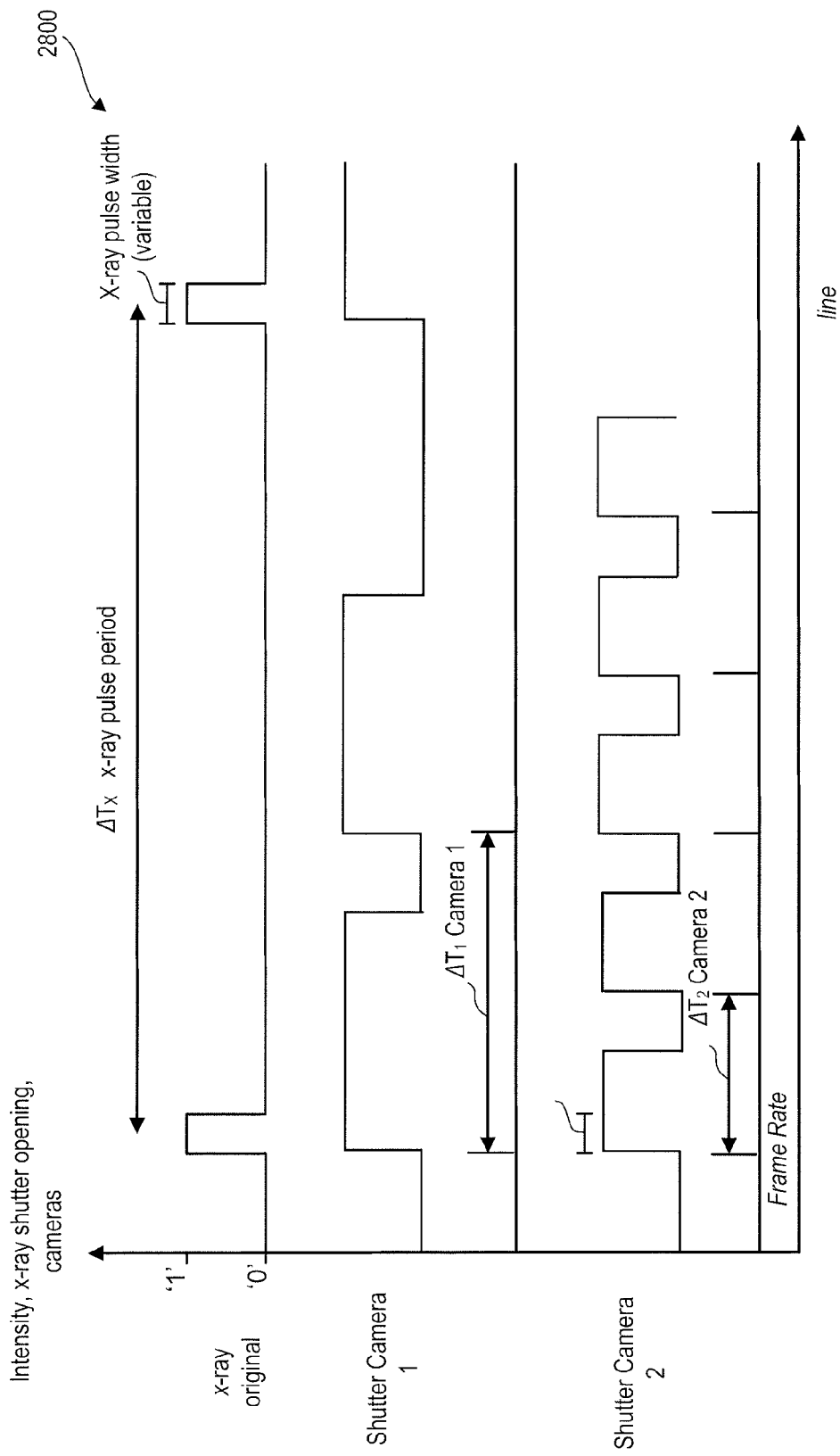
FIG. 28 is a timing diagram illustrating a dual-energy image acquisition sequence using multiple image frame for each X-ray pulse emitted, in the system of claim 26.

As illustrated in diagram 2800 of FIG. 28, the camera(s) frame rate(s) are also independently adjustable, such that a digital camera can acquire several frames for each X-ray pulse period. Depending on the physics of afterglow for a given fluorescent screen composition, as known in the art, this flexibility allows capture of "dark frames," possibly for each X-ray pulse period, enabling accurate dark-current electronic correction as known in the art.

Real-Time Residual Lag and Afterglow Correction

Figure 29:
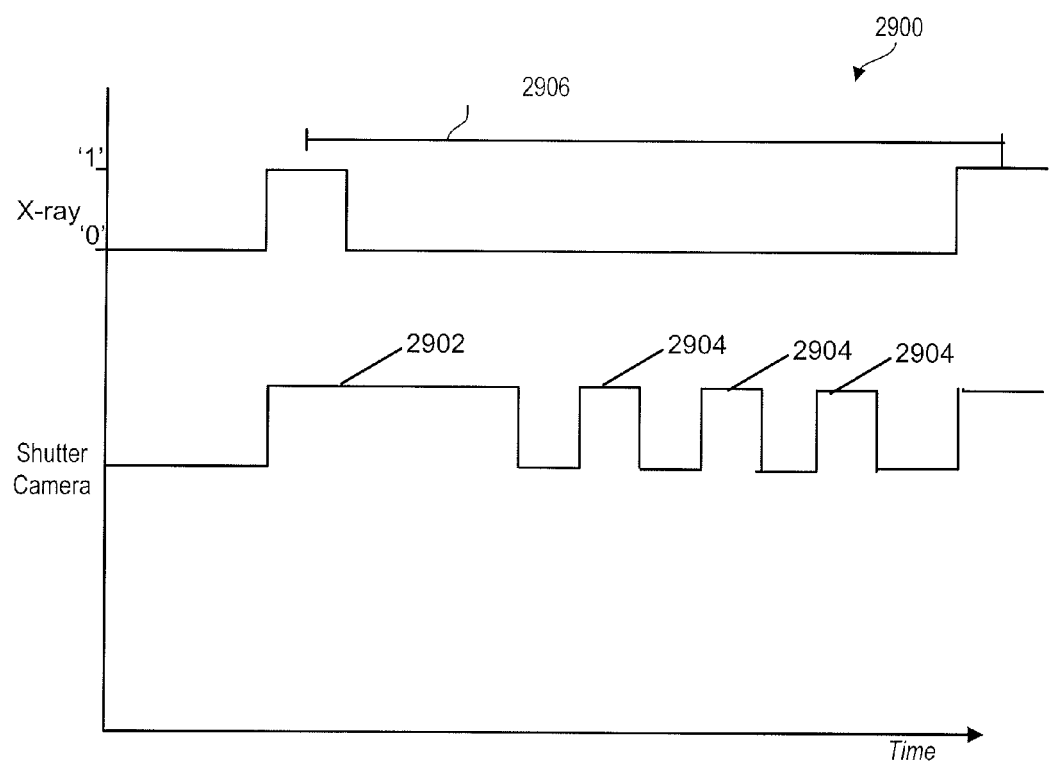
FIG. 29 is a timing diagram illustrating acquisition of multiple frames per X-ray pulse to enable pre-processing of acquired data to compensate for detector effects such as afterglow by modeling afterglow of fluorescent screens, in the system of FIG. 26.

This flexibility provided by digital imaging and advanced camera and shutter technologies enables real-time observation of the afterglow data, through capture of one or more "afterglow frames." Such observation(s) enable correction for the residual afterglow data that may be captured as part of the next X-ray pulse frame, should the phosphor have a long afterglow and the X-ray pulse period be too short for afterglow effects to be negligible in that next X-ray pulse frame. Correction can proceed by modeling the afterglow decay from the measured data. Such an embodiment is illustrated schematically in diagram 2900 of FIG. 29, showing the acquisition of three "afterglow" or "decay" frames 2904 following acquisition of a "primary" frame 2902 during each X-ray pulse period 2906.

Figure 30:
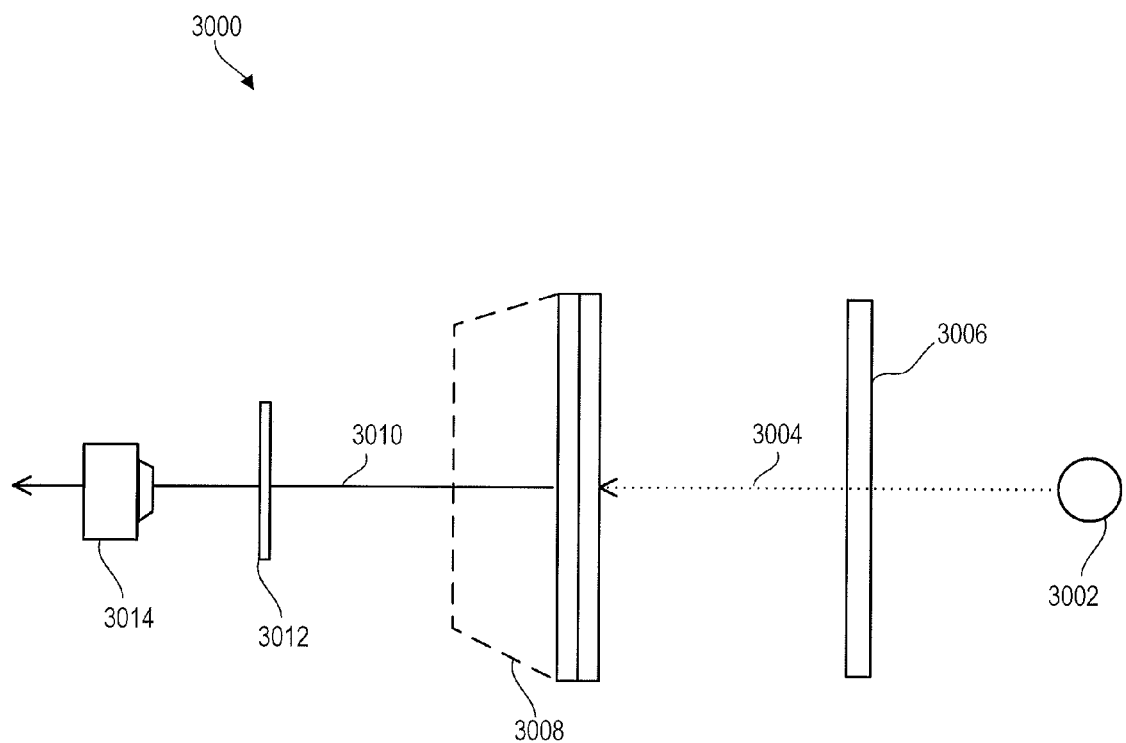
FIG. 30 is a simplified side view showing in-line geometry of a system for dynamic low dose X-ray imaging and tomosynthesis, according to an embodiment.

Recent developments, including developments in CMOS technologies, have lead to the introduction of X-ray resistant devices. Such devices enable "in-line" geometries as illustrated in FIG. 30. In geometry 3000, an image-intensifier device may be substituted for a fluorescent screen, as know in the art and shown in FIG. 30. Such geometries are generally preferable in terms of light collection efficiency and design volume considerations.

X-ray source 3002 emits a fan beam 3004 through rotating collimator 3006 to impact rotating screen and/or image intensifier 3008. Light 3010 is then electronically imaged by lens 3012 and camera 3014. Once captured, images are processed as heretofore described.

Nonrotating Detector Embodiment

In an alternative embodiment, X-ray tube 1602/2502 and rotating collimator 1604/2504 are mounted on one end of a C-arm, as previously described. At the opposite end of the C-arm is mounted at least one fluorescent screen (e.g., screen) 2510 or image intensifier (e.g., image intensifier 3008), detector and associated camera (e.g., 2518, 3014), essentially as described with reference to FIG. 25, 26 or 30; except that the detector and camera do not rotate. In this embodiment, translation of dexel coordinates to Cartesian is not needed during processing, and afterglow is less significant than in rotating detector embodiments because the patient moves much less rapidly than the beam periphery.

In the nonrotating detector embodiment, digital signal processor 1630 simulates a rotating window synchronous with, and aligned with, rotation of wing portions of the fan beam 1624, 2506. The virtual rotating window is shaped to match the fan beam. This virtual rotating window is "AND"ed with each captured frame from the camera, pixels outside the virtual rotating window are ignored because radiation detected by them is due to scatter. Pixels inside the rotating window are updated in the reconstructed image in memory. Pixels in the central portion are updated continuously.

Residual Scatter Correction

Availability of the full-frame data allows scatter correction, as the scatter field is directly measured outside the projected primary beam. The forward scatter field at medical X-ray imaging energies is weakly forward-peaked and hence varies relatively slowly spatially in the image; this fact enables estimation of the residual scatter field collected with the primary, and subsequent correction (by subtraction of the estimate).

A desirable property enabled by the present invention is that of dynamic variable collimation. A collimator of the present invention may be constructed with beam adjustment blades 1028 (FIG. 10), it is possible to change the beam width by moving blades 1028 in and out to shorten the beam wings, similar to the embodiment shown in FIG. 10A and FIG. 10B.

Figure 33:
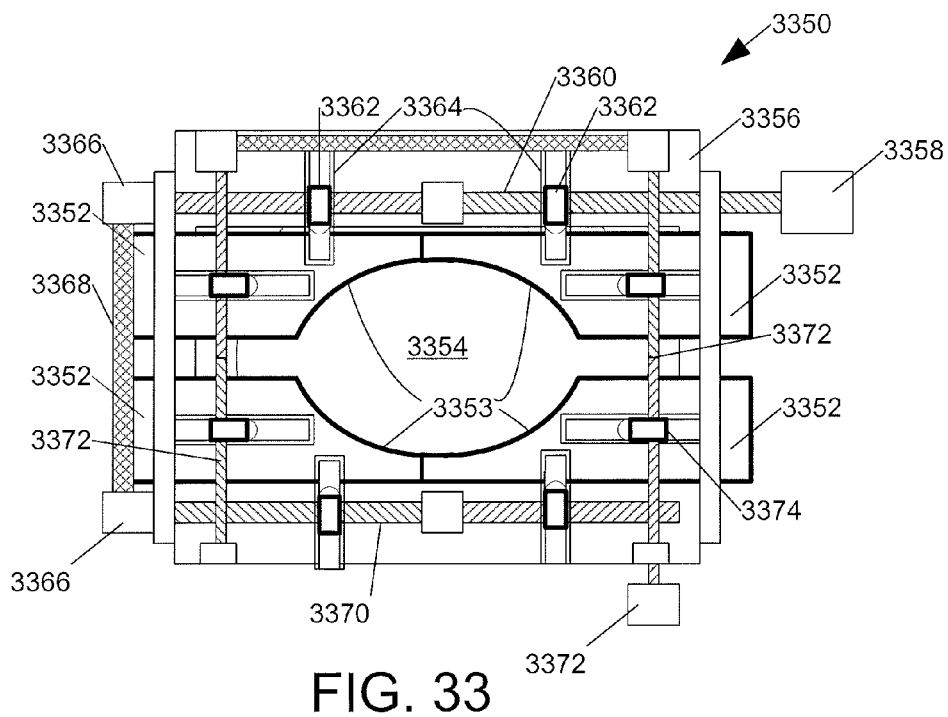
FIG. 33 illustrates an adjustable collimator for providing a fan beam having a central portion significantly wider than a wing portion.
Figure 33A:
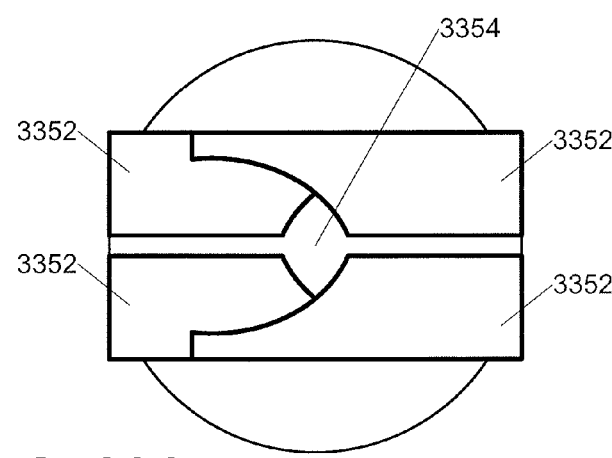
FIG. 33A illustrates a narrow setting of the blades of the collimator of FIG. 33.

Collimator blades may also include a circular or partially circular opening FIGS. 33, 33A, the motion of which resulting in a variable diameter of the central region of the fan beam. The collimator 3350 of FIG. 33 has four collimator blades 3352 having arcuate edges 3353, shown in a retracted position providing a wide central opening 3354. These blades are shown without mounting or adjustment mechanism in an advanced position providing a narrow central opening in FIG. 33A.

In an embodiment, illustrated in FIG. 33, blades 3352 are slideably mounted in a frame 3356. Adjustment of center opening, and thereby fan beam center portion effective diameter, is performed by rotating knob 3358, which rotates shaft 3360. Shaft 3360 is threaded with a left-hand thread on one half, and a right hand thread on the remaining half, such that rotation of shaft 3360 draws nuts 3362 equally towards or away from the center of the shaft along an X axis. Nuts 3362 are slideably engaged with ears 3364 attached to a first pair of blades 3352 such that blades 3352 are free to move in a Y axis perpendicular to the X axis. Bevel gears 3366 and cross-shaft 3368 are provided such that shaft 3370 on the opposing side synchronously moves a second pair of blades 3352. Similarly, a second adjustment knob 3372 adjusts blade position in the Y axis to set width of the fan beam wings through rotating shafts 3372 each having a left-hand thread on one half, and a right hand thread on the remainder, engaged with nuts 3374, the nuts 3374 slideably engaged with a track on blades 3352.

The variable-center collimator of FIG. 33 may be combined with the adjustable wings as illustrated in FIG. 10, and the adjustable wing blades may be made screw-adjustable in a manner similar to that of the X axis adjustment of FIG. 33.

Figure 31:
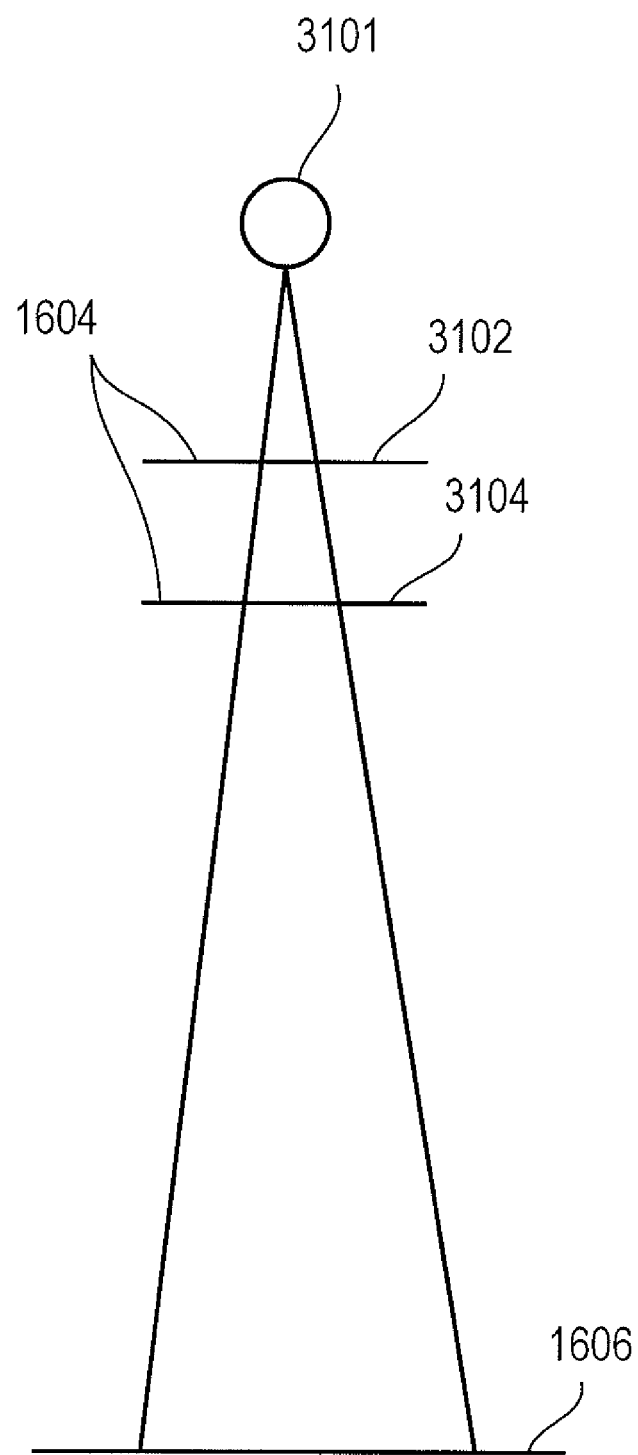
FIG. 31 schematically illustrates use of geometric magnification to achieve variable collimation, in a system for dynamic low dose X-ray imaging and tomosynthesis.

Another alternative means of obtaining variable collimation, which may be used with the approach of FIG. 10 or FIG. 33, relies on geometric magnification, as presented schematically in FIG. 31. By moving the collimator 1604, or a part thereof, closer to or further away from the X-ray tube 3101, as from position 3102 (large beam) to 3104 (narrow beam); or the tube and detector combination closer to or further away from the detector or screen, the projected aperture size on the screen varies in size; the length of the wings can be maintained constant, or adjusted, by adjusting the position of a pair of collimator blades as shown in FIG. 10A. Other mechanical implementations are possible that will also achieve this particular object of the present invention.

Yet another option, not illustrated in drawings, for achieving variable collimation is to perform collimation using a removable lead plate having a hole cut to allow X-ray emission. A selection of lead plates can be provided, the radiologist substituting a plate suitable for each type of procedure into the system 1600.

Slot-Scanning Modes and Multi-Spectral Imaging

Figure 32:
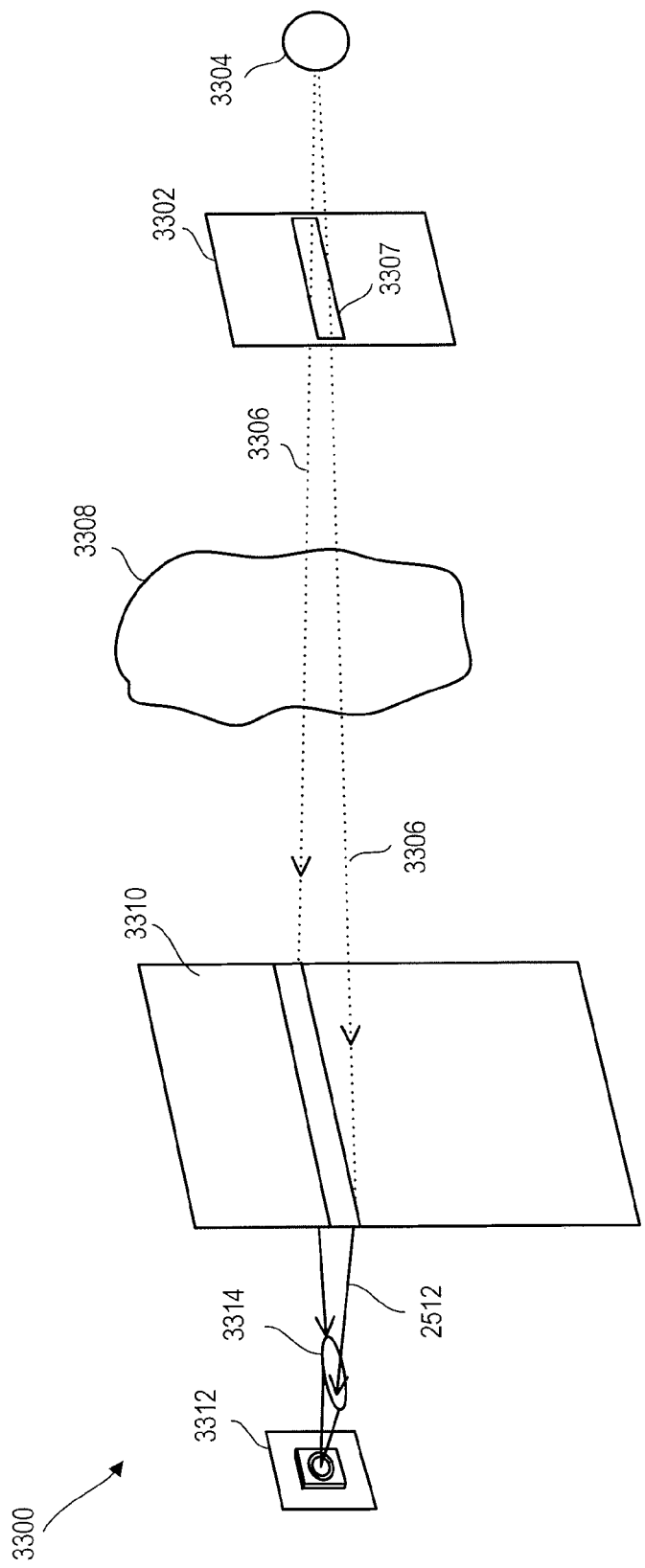
FIG. 32 schematically illustrates the use of slot-scanning with, in a system for dynamic low dose X-ray imaging and tomosynthesis, according to an embodiment.

FIG. 32 shows a diagram 3300 illustrating another embodiment of the present invention with application to slot-scanning. A slit/slot collimator 3302 is made to translate in front of a fixed (or pivoting) X-ray source 3304 so that a fan-beam 3306 of X-rays passes through a slit/slot 3307 and an object 3308 to project onto a large fluorescent screen 3310, the screen being optically coupled to a high frame-rate digital camera 3312 as in previous embodiments (for example, via a lens 3314. Such an application enables digital multi-spectral imaging in a single scan, as described in U.S. Pat. No. 6,950, 492 issued to the present inventor. Alternate embodiments include a mechanical arrangement in which source 3304 and collimator assembly is made to translate or otherwise move with respect to the fluorescent screen or image intensifier. In yet a further embodiment, both the detector (screen or image intensifier 3310) and X-ray source 3304 are fixed, and the object or subject is made to translate or otherwise move through an imaging apparatus comprising the X-ray source and detector. Additional embodiments are possible to attain this object of the present invention.

Performing a Medical Procedure

The above-described instrumentalities have utility in performing diagnostic and interventional procedures. When a diagnostic coronary catheterization is performed, as illustrated in FIG. 16B, the C-arm apparatus herein described is positioned to image a patient's chest, with the image center located over the root of the aorta. An incision is made into one of the femoral arteries of a patient's groin. A catheter 1618 is then threaded through the femoral and iliac arteries, then through the aorta to the root of the aorta near the aortic valve. This point is also the origin of the coronary arteries. A sequence of images is taken as the catheter is threaded to the aortic root to verify the catheter does not enter other arteries instead. The catheter is then teased into the left or right coronary artery while the apparatus herein described is operated in a continuous fluoroscopic mode to monitor placement. Once the catheter is correctly positioned, the image center may be repositioned to better cover the expected distribution of blood flow in the coronary arteries. A radio-opaque dye is injected through the catheter while the system 1600 is used to record a continuous rapid sequence of fluoroscopic images showing dynamic dye flow through the selected coronary artery. Typically, the apparatus is repositioned, more dye injected, and further images recorded from a different angle. Then the catheter is teased into the other coronary artery and dynamic dye flow in that artery is imaged.

When a PTCA is performed, the C-arm apparatus herein described is positioned to image a patient's chest. As with coronary angiography, an incision is made into one of the femoral arteries of a patient's groin. An angioplasty catheter, which may have a stent attached, is threaded to the root of the aorta. A sequence of images is taken with the apparatus as the catheter is threaded to the aortic root to verify the catheter does not enter other arteries instead. The catheter is then teased into the coronary artery needing treatment. The apparatus herein described is operated in a real-time, continuous, fluoroscopic mode (typically with a frame rate of 15 to 30 frames per second) in bursts, with the image center positioned over the patient's heart, to monitor catheter placement as the catheter is threaded through the coronary artery in the beating heart to the obstruction being treated. Dye is injected through a lumen of the catheter to permit visualization of the artery to ensure correct catheter placement. When the catheter is correctly positioned, a balloon near the catheter tip is inflated to open the artery and deploy the stent. The catheter may then be withdrawn slightly and more dye injected to verify correct stent placement and observe flow of blood and dye through the artery. The catheter is then removed from the patient and the femoral artery wound is closed.

What is claimed is:

1. A system for creating a rapid sequence of X-ray images of a subject, comprising:
   an X-ray source;
   a collimator for collimating X-ray photons from the X-ray source into a fan beam having a center portion and a wing portion, a measurement selected from a width and a diameter of the center portion being larger than a width of the wing portion;
   apparatus for rotating the collimator to spin the fan beam about an axis extending from the X-ray source to a detector, wherein the wing portion of the fan beam intermittently illuminates at least a portion of the subject disposed between the collimator and the detector;
   the detector being capable of receiving the fan beam and for generating electronic information therefrom; and
   an image processor for constructing a rapid sequence of images of the subject from the electronic information.

2. The system of claim 1 wherein the measurement of the center portion of the fan beam is at least twice the width of the wing portion of the fan beam.

3. The system of claim 2 wherein the detector has a center portion centered on the axis and at least one wing portion, and wherein the detector is rotated about the axis synchronously with rotation of the collimator.

4. The system of claim 2 wherein the detector is an area detector that is not rotated synchronously to rotation of the collimator.

5. The system of claim 4 wherein the image processor maintains a virtual window aligned with the fan beam and rotated synchronously with rotation of the collimator.

6. The system of claim 2, further comprising apparatus for automatically sensing a location of a catheter tip within the subject, and apparatus for automatically adjusting positions of the detector and collimator such that the axis intersects the catheter tip.

7. The system of claim 2, wherein the shape of the fan beam is adjustable through positioning blades within the collimator.

8. The system of claim 6 wherein the collimator is rotated at a rate in revolutions per second of at least one divided by a count of wing portions in the fan beam.

9. The system of claim 2 wherein the width of the wing portion of the beam is less than two centimeters.

10. The system of claim 8 wherein no potter-bucky grid is provided on at least that portion of the detector that receives wing portions of the fan beam.

11. The system of claim 1 wherein the detector is capable of determining photon energy.

12. The system of claim 1 wherein the detector comprises a first fluorescent screen and a second fluorescent screen, the first fluorescent screen positioned to receive the fan beam as attenuated by the subject, and the second fluorescent screen positioned to receive X-rays that penetrate the first fluorescent screen.

13. The system of claim 1 wherein the detector comprises a first fluorescent screen and an electronic camera.

14. The system of claim 1 wherein the detector is a semiconductor detector.

15. A method for creating a rapid sequence of X-ray images of a subject, comprising:
   generating X-ray radiation in an X-ray source;
   passing the X-ray radiation through a collimator that rotates about an axis extending from the X-ray source to an X-ray detector, thereby forming a spinning fan beam centered on the axis, the fan beam having a center portion and a wing portion, a measurement selected from a width and a diameter of the center portion being larger than a width of the wing portion;
   passing at least a portion of the fan beam through a portion of the subject;
   receiving the fan beam in the X-ray detector and generating electronic information therefrom; and
   constructing a rapid sequence of images of the subject from the electronic information.

16. The method of claim 15 wherein the measurement of the center portion of the beam is at least twice a width of the wing portion of the beam.

17. The method of claim 15 wherein the detector has a center portion centered on the axis and a wing portion, and wherein the detector is rotated about the axis synchronously with rotation of the collimator.

18. The method of claim 15 wherein the detector is not rotated synchronously to rotation of the collimator, and wherein the image processor maintains a virtual window aligned with the fan beam, the virtual window is rotated synchronously with rotation of the collimator, and the virtual window is used to determine portions of an image to update.

19. The method of claim 15, further comprising automatically sensing a location of a catheter tip within a human patient, and automatically adjusting positions of the detector and collimator such that the axis intersects a region of interest of the subject near the catheter tip.

20. The method of claim 15, further comprising adjusting the shape of the fan beam through repositioning blades within the collimator.

21. The method of claim 15 wherein the collimator is rotated at a rate of at least one revolution per second.

22. The method of claim 15 wherein the width of the wing portion of the beam is less than two centimeters.

23. The method of claim 15, further comprising determining an energy distribution of X-ray photons of the beam as received at the detector.

24. A method for performing a medical procedure on a patient comprising:
   generating X-ray radiation;
   passing the X-ray radiation through a rotating collimator to form a spinning fan beam having an axis, a center portion, and a wing portion;
   passing at least a portion of the fan beam through a region of interest of the patient;
   receiving the spinning fan beam in an X-ray detector and generating electronic information therefrom;

constructing a rapid sequence of images of the region of interest in the patient from the electronic information;
passing a catheter through a vessel of the patient into the region of interest in the patient; and
using the rapid sequence of images to image the catheter and to guide placement of a tip of the catheter.

25. The method of claim 24, further comprising passing a radio-opaque dye through the catheter and obtaining a further rapid sequence of images to observe flow of the radio-opaque dye through vessels of the patient.

26. A system for creating a rapid sequence of X-ray images of an subject, comprising:
an X-ray source capable of emitting X-ray photons;
a collimator for collimating the X-ray photons from the X-ray source into a fan beam having a center portion and a wing portion, a measurement selected from a width and a diameter of the center portion being larger than a width of the wing portion;
apparatus for rotating the collimator to spin the fan beam about an axis extending from the X-ray source to a detector, the wing portion of the fan beam thereby intermittently illuminating at least a portion of the subject disposed between the collimator and the detector; and
an image processor for constructing the rapid sequence of images of the subject from the electronic information.

27. The system of claim 26 wherein X-ray source emits the X-ray photons in pulses, and wherein the detector captures a sequence of images associated with each pulse of X-ray photons, and wherein the sequence of images associated with each pulse of X-ray photons is used to compensate for afterglow of the detector.

28. The system of claim 26 wherein the detector is a solid-state detector.

29. The system of claim 26 wherein the detector comprises at least a first fluorescent screen for receiving X-ray photons of the fan beam and an optical imaging device for generating electronic information therefrom.

30. The system of claim 29 wherein the detector further comprises a second fluorescent screen for receiving X-ray photons of the fan beam that penetrate the first fluorescent screen.

* * * * *